US010556883B2

United States Patent
Ouvry et al.

(10) Patent No.: US 10,556,883 B2
(45) Date of Patent: Feb. 11, 2020

(54) BENZENESULFONAMIDE COMPOUNDS, METHOD FOR SYNTHESIZING SAME, AND USE THEREOF IN MEDICINE AND COSMETICS

(71) Applicant: GALDERMA RESEARCH & DEVELOPMENT, Biot (FR)

(72) Inventors: Gilles Ouvry, Biot (FR); Craig Steven Harris, Biot (FR); Yushma Bhurruth-Alcor, Antibes (FR)

(73) Assignee: GALDERMA RESEARCH & DEVELOPMENT, Biot (FR)

(*) Notice: Subject to any disclaimer, the term of this patent is extended or adjusted under 35 U.S.C. 154(b) by 0 days.

(21) Appl. No.: 15/421,963

(22) Filed: Feb. 1, 2017

(65) Prior Publication Data

US 2017/0247353 A1    Aug. 31, 2017

(30) Foreign Application Priority Data

Feb. 1, 2016    (EP) .................................... 16153702

(51) Int. Cl.
  *C07D 401/12*    (2006.01)
  *C07D 405/14*    (2006.01)
  *C07D 401/14*    (2006.01)
  *C07D 413/14*    (2006.01)

(52) U.S. Cl.
  CPC ......... *C07D 401/12* (2013.01); *C07D 401/14* (2013.01); *C07D 405/14* (2013.01); *C07D 413/14* (2013.01)

(58) Field of Classification Search
  None
  See application file for complete search history.

(56) References Cited

U.S. PATENT DOCUMENTS

2002/0013341 A1*  1/2002  Duan ................... C07D 211/34
                                                    514/312

FOREIGN PATENT DOCUMENTS

| WO | 96/00214 A1 | 1/1996 |
|---|---|---|
| WO | 97/18194 A1 | 5/1997 |
| WO | 97/22587 A1 | 6/1997 |
| WO | 98/16503 A2 | 4/1998 |
| WO | 98/16506 A1 | 4/1998 |
| WO | 98/16514 A1 | 4/1998 |
| WO | 98/16520 A1 | 4/1998 |
| WO | 98/33768 A1 | 8/1998 |
| WO | 00/44709 A2 | 8/2000 |
| WO | 2008/045671 A1 | 4/2008 |
| WO | 2011/001088 A1 | 1/2011 |
| WO | 2011/001089 A1 | 1/2011 |
| WO | 2011/033009 A1 | 3/2011 |
| WO | 2011/033010 A1 | 3/2011 |

OTHER PUBLICATIONS

Silverman, RB. The Organic Chemistry of Drug Design and Drug Action 2nd Ed. El Sevier. 2004, p. 29-30.*
Wajant, H. et al. Tumor necrosis factor signaling. Nature, 2003, p. 45.*
Yost, J. et al. The Role of TNF inhibitors. Medicine Reports, 2009, p. 1.*
O'Shea, JJ. et al. In search of magic bullets: the golden age of immunotherapeutics. Cell, 2014, p. 227.*
Moss, M.L. et al., "Cloning of a disintegrin metalloproteinase that processes precursor tumour-necrosis factor-alpha," Nature 1997, vol. 385, pp. 733-736.
Schlondorff, J. et al., "Intracellular maturation and localization of the tumour necrosis factor alpha convertase (TACE)," Biochem. J. 2000, vol. 347, pp. 131-138.
Lohmander, L.S., "The Structure of Aggrecan Fragments in Human Synovial Fluid," Arthritis Rheum, 1993, vol. 36, pp. 1214-1222.
MacDonald, T.T. et al., "Tumour necrosis factor-alpha and interferon-gamma production measured at the single cell level in normal and inflamed human intestine," Clin. Exp. Immunol. 1990, vol. 81, pp. 301-305.
Bonifati, C. et al., "Correlated increase of tumour necrosis factor-alpha, interleukin-6 and granulocyte monocyte-colony stimulating factor levels in suction blister fluids and sera of psoriatic patients—relationship with disease severity," Clin. Exp. Dermatol., 1994, vol. 19, pp. 383-387.
Kupper, T.S., "Immunologic Targets in Psoriasis," N. Engl. J. Med, 2003, vol. 349, pp. 1987-1990.

* cited by examiner

Primary Examiner — D Margaret M Seaman
(74) Attorney, Agent, or Firm — Sunit Talapatra; Foley & Lardner LLP

(57) ABSTRACT

Compounds having formula (I) are described.

Also described, are methods of using these compounds to treat diseases, conditions, and disorders.

12 Claims, No Drawings

BENZENESULFONAMIDE COMPOUNDS, METHOD FOR SYNTHESIZING SAME, AND USE THEREOF IN MEDICINE AND COSMETICS

CROSS-REFERENCE TO PRIOR APPLICATIONS

This application claims priority under 35 U.S.C. § 119 to European Patent Application No. EP 16153702.2, filed Feb. 1, 2016, hereby expressly incorporated by reference in its entirety and each assigned to the assignee hereof.

TECHNICAL FIELD

The present invention relates to benzenesulfonamide compounds of formula (I) below:

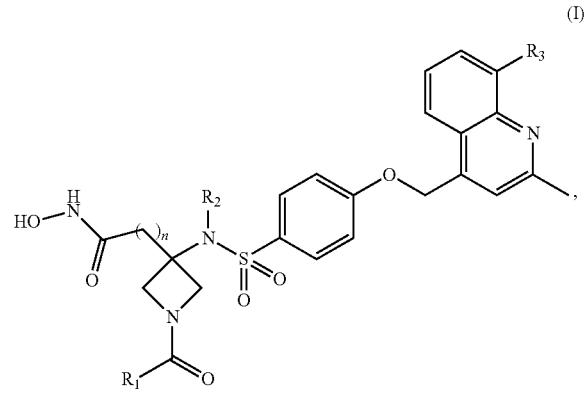

to the process for preparing the compounds of formula (I), and to compounds of formula (I) for use in pharmaceutical compositions for the treatment of diseases, conditions, and disorders. The compounds of the present invention act as inhibitors of TNFα-converting enzyme, also known as TACE or ADAM17. They are consequently of use in the treatment of TNFα mediated diseases, conditions, or disorders. The present invention also relates to the use of the compounds of formula (I) in cosmetic compositions.

BACKGROUND

Adamalysins ("ADAM" or A Disintegrin and Metalloproteinase) are a subfamily of zinc metalloendopeptidase enzymes. Their ectodomain comprises a protease domain, the activation of which is zinc-dependent, a disintegrin domain and a cysteine-rich domain. To date, at least 30 different ADAMs have been identified, of which the first characterized was ADAM17, also known as TACE (TNFα-converting enzyme) [Gueydan C et al. Med. Sci 1997, 13, 83-88; Black R. A et al. Nature 1997, 385:729-733; Moss et al. Nature 1997, 385:733-736]. The TACE mRNA is present in many tissues and more particularly in monocytes, macrophages and T lymphocytes, but also in keratinocytes for example. TACE is responsible for the cleavage of pro-TNFα, a 26 kDa membrane protein, so as to result in the release of biologically active soluble TNFα, a 17 kDa protein [Schlondorff et al. Biochem. J. 2000, 347, 131-138]. The soluble TNFα released by the cell is capable of acting on sites very remote from the site of synthesis.

TNFα is involved in a large number of pro-inflammatory biological processes [Aggarwal et al, Eur. Cytokine Netw., 1996, 7: 93-124]. Several pharmacological and clinical studies have shown in an obvious manner that blocking the effects of TNFα with specific anti-TNFα antibodies or anti-TNFα biologicals (Etanercept, Adalimumab, Infliximab) is beneficial in the treatment of autoimmune diseases such as rheumatoid arthritis [Feldman et al. Lancet, 1994, 344, 1105], non-insulin-dependent diabetes mellitus [Lohmander L. S et al. Arthritis Rheum, 1993, 36, 1214-1222], or Crohn's disease [MacDonald et al. Clin. Exp. Immunol. 1990, 81, 301].

TNFα also plays a fundamental role during the inflammatory phenomenon triggered in psoriasis lesions. Serum TNFα levels are elevated in psoriatic patients [Mussi A et al. J. Biol. Regul. Homeost Agents, 1997, 11, 115-118]; TNFα levels are also elevated in the actual psoriasis plaques [Bonifati C. et al. Clin. Exp. Dermatol., 1994, 19, 383-387]. The key cells in the physiopathology of psoriasis are keratinocytes, dendritic cells and certain T lymphocytes. The interaction between these families of cells results in an inflammatory cascade that leads to the characteristic psoriasis lesions with release of TNFα [Kupper T S, N. Engl. J. Med, 2003, 349, 1987-1990]. Clinical studies for the treatment of moderate to severe plaque psoriasis with anti-TNFα biologicals (Etanercept, Adalimumab, Infliximab) have demonstrated their efficacy both on psoriasis lesions and on the quality of life of the patients [Ortonne J P, Annales de dermatologie et de venereologie {Annals of dermatology and venereology], 2005, 132 (8-9 pt2), 4S6-9 and 2005, 132, 9S01-9S70].

Thus, compounds which inhibit TNFα production are of great interest for the treatment of inflammatory diseases and diseases involving TNFα release.

SUMMARY

The present invention provides compounds having formula (I)

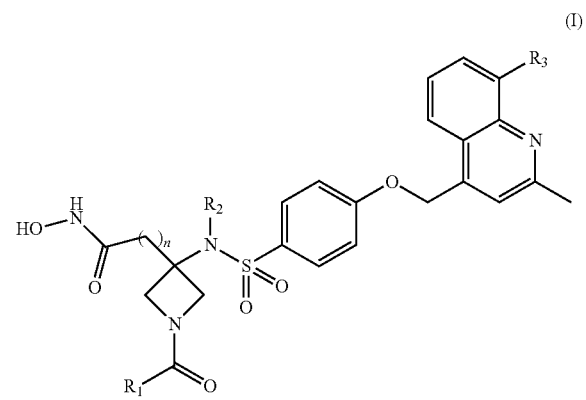

in which:
R₁ is a hydrogen atom, an alkyl radical, a substituted alkyl radical, an alkenyl radical, a substituted alkenyl radical, an alkynyl radical, a substituted alkynyl radical, an aralkyl radical, a substituted aralkyl radical, a heteroaralkyl radical, a substituted heteroaralkyl radical, an alkoxy radical, a substituted alkoxy radical, a cycloalkyl radical, a substituted cycloalkyl radical, a heterocyclic radical, a substituted heterocyclic radical, an amine radical, a substituted amine radical, a cyclic amine radical, or a heterocyclic amine radical;

R₂ is a hydrogen atom, an alkyl radical or a substituted alkyl radical;

R₃ is a hydrogen atom, an alkyl radical, a substituted alkyl radical, an alkynyl radical, a substituted alkynyl radical, an alkoxy radical, a halogen radical, or a nitrile radical; and n is 0 or 1.

The present invention also provides salts and enantiomers, including pharmaceutically acceptable salts and enantiomers, of the compound of formula (I). The present invention also provides compositions and pharmaceutical compositions comprising the compound of formula (I) and a carrier or a pharmaceutically acceptable carrier.

Another object of the invention is a compound as defined herein as a medicament.

The compounds disclosed herein are TACE inhibitors. Accordingly, the present invention provides a compound of formula (I), for use in the treatment of diseases, disorders, or conditions involving inhibition of TNFα production The diseases, disorders, or conditions include, but are not limited to, inflammatory skin diseases, such as psoriasis, atopic dermatitis, psoriatic arthritis, acne, allergic contact dermatitis and actinic keratosis.

DETAILED DESCRIPTION

The present invention provides novel molecules which inhibit the TACE enzyme (TNFα-converting enzyme) and, as a result, inhibit the secretion of soluble TNFα (active form of TNFα) by cells. These novel molecules are therefore potential active ingredients for the treatment of pathological conditions which involves a decrease or an inhibition of TNFα production.

By way of illustration, and in a nonlimiting manner, these pathological conditions are, for example, septic shock, hemodynamic shock, malaria, inflammatory bowel diseases (IBDs) such as Crohn's disease and ulcerative colitis, inflammatory bone diseases, mycobacterial infections, meningitis, fibrotic diseases, cardiac diseases, ischemic attack, transplant rejection, cancer, atherosclerosis, obesity, diseases involving angiogenesis phenomena, autoimmune diseases, osteoarthritis, rheumatoid arthritis, ankylosing spondylitis, juvenile chronic arthritis, multiple sclerosis, HIV, non-insulin-dependent diabetes mellitus, allergic diseases, asthma, chronic obstructive pulmonary disease (COPD), ocular inflammation, and inflammatory skin diseases, such as, but not limited to, psoriasis, atopic dermatitis, psoriatic arthritis, acne, allergic contact dermatitis and actinic keratosis.

These molecules are also potential active ingredients for the treatment of neurological pathological conditions that are inflammatory in nature, for which reducing TNFα production would be of great interest. These pathological conditions listed hereinafter in a nonlimiting manner are, for example, Alzheimer's disease, Parkinson's disease, Parkinsonian disorders, amyotrophic lateral sclerosis, autoimmune diseases of the nervous system, autonomic diseases of the nervous system, dorsal pain, cerebral edema, cerebrovascular disorders, dementia, nervous system nerve fiber demyelinating autoimmune diseases, diabetic neuropathies, encephalitis, encephalomyelitis, epilepsy, chronic fatigue syndrome, giant cell arteritis, Guillain-Barré syndrome, headaches, multiple sclerosis, neuralgia, peripheral nervous system diseases, polyneuropathies, polyradiculoneuropathy, radiculopathy, respiratory paralysis, spinal cord diseases, Tourette's syndrome, central nervous system vasculitis, Huntington's disease and stroke.

TACE inhibitors are already known. However, a large number of these inhibitors do not act selectively on the TACE enzyme compared with other enzymes of the family of ADAMs and/or of matrix metalloproteinases (MMPs).

As it happens, the nonselective inhibition of these enzyme families induces adverse side effects observed in vivo. For example, the inhibition of MMP-1 (collagenase-1) has been associated with musculoskeletal toxicity problems. As a nonselective inhibitor, mention may also be made of Apratastat, a known inhibitor tested clinically in phase 2 for the treatment of rheumatoid arthritis (Curr Opin Investig Drugs. 2006 November; 7(11), 1014-1019). This inhibitor is not selective for the TACE enzyme compared with certain MMPs (WO 00/44709, page 251, table 10, example 61).

Other TACE inhibitors which are also known and are part of the same family as Apratastat, namely that of cyclic benzenesulfonamide derivatives, have been described in WO 00/44709 and WO 97/18194. Other patents (WO 96/00214, WO 97/22587, WO98/33768) claim MMP and/or TACE inhibitors for which the benzenesulfonamide part is separated from the hydroxamic acid function by a single carbon atom. Publications describing MMP inhibitors of this type more broadly are also the publication by MacPherson et al. J. Med. Chem. 1997, 40, 2525 and the publication by Tamura et al. J. Med. Chem. 1998, 41, 640. Other examples of MMP/TACE inhibitors for which the sulfonamide function is separated from the hydroxamic acid by a series of two carbon atoms are described in patents WO 98/16503, WO 98/16506, WO 98/16514, WO 98/16520, WO2011/1088, WO2011/1089, WO2011/33009 and WO2011/33010. Other examples of MMP inhibitors for which the sulfonamide function is separated from the hydroxamic acid by a series of two carbon atoms are also described in WO 2008/045671.

Compounds of formula (I) provided herein exhibit a good TACE-inhibiting activity in a cellular setting (human Peripheral Blood Mononuclear Cell) with an IC50 of less than or equal to 1 μM. In addition, the compounds inhibit the TACE enzyme selectively compared with MMP1. Moreover, compounds have properties suitable for topical administration.

Thus, the present invention provides compounds of formula (I) below:

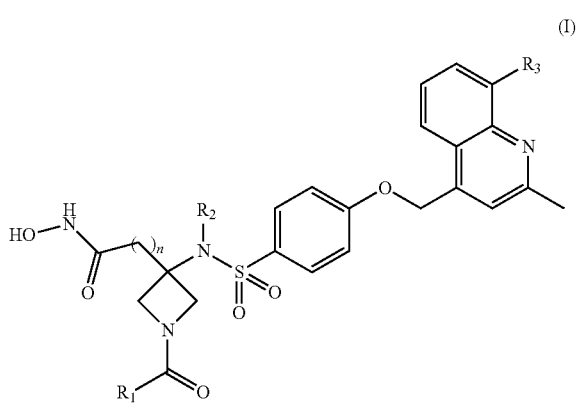

(I)

in which:

R₁ is a hydrogen atom, an alkyl radical, a substituted alkyl radical, an alkenyl radical, a substituted alkenyl radical, an alkynyl radical, a substituted alkynyl radical, an aralkyl radical, a substituted aralkyl radical, a heteroaralkyl radical, a substituted heteroaralkyl radical, an alkoxy radical, a substituted alkoxy radical, a cycloalkyl radical, a substituted cycloalkyl radical, a heterocyclic radical, a substituted heterocyclic radical, an amine radical, a substituted amine radical, a cyclic amine radical, or a heterocyclic amine radical;

$R_2$ is a hydrogen atom, an alkyl radical or a substituted alkyl radical;

$R_3$ is a hydrogen atom, an alkyl radical, a substituted alkyl radical, an alkynyl radical, a substituted alkynyl radical, an alkoxy radical, a halogen radical, or a nitrile radical; and n is 0 or 1.

The present invention also provides salts of the compound of formula (I). More specifically, the salts are pharmaceutically and/or physiologically acceptable salts of the compound of formula (I). Moreover, the present invention provides enantiomers, in particular pharmaceutically acceptable enantiomers, of the compound of formula (I).

Additionally, provided herein are salts of the compounds of formula (I) formed with a pharmaceutically acceptable acid, salts of the compounds of formula (I) formed with a pharmaceutically acceptable base, and enantiomers of the compounds of formula (I).

Salts of the compounds of formula (I) formed with a pharmaceutically acceptable acid, include salts formed with an organic acid or with an inorganic acid. The suitable inorganic acids are, for example, hydrohalic acids such as hydrochloric acid or hydrobromic acid, sulfuric acid, nitric acid, and phosphoric acid. The suitable organic acids are, for example, acetic acid, trifluoroacetic acid, trichloroacetic acid, propionic acid, glycolic acid, pyruvic acid, succinic acid, benzoic acid, cinnamic acid, mandelic acid, methanesulfonic acid, para-toluenesulfonic acid, salicylic acid, picric acid, citric acid, oxalic acid, tartaric acid, malonic acid, maleic acid, camphorsulfonic acid, and fumaric acid.

Salts of the compounds of formula (I) formed with a pharmaceutically acceptable base include salts formed with an organic base or with an inorganic base. The suitable inorganic bases are, for example, potassium hydroxide, sodium hydroxide, lithium hydroxide or calcium hydroxide. The suitable organic bases comprise amines and amino acids. Examples of amines include but are not limited to aliphatic or aromatic, primary, secondary, or tertiary amines, such as methylamine, ethylamine, ethanolamine, propylamine, isopropylamine, the 4 isomers of butylamine, dimethylamine, diethylamine, diethanolamine, dipropylamine, diisopropylamine, di-n-butylamine, pyrrolidine, piperidine, morpholine, diethanolphenylamine, trimethylamine, triethylamine, tripropylamine, quinuclidine, pyridine, quinoline, or isoquinoline. Examples of amino acids include but are not limited to lysine, arginine, and ornithine.

As used herein, the term "alkyl radical" denotes a linear or branched, saturated hydrocarbon-based chain containing from 1 to 10 carbon atoms. Examples of alkyl groups having from 1 to 10 carbon atoms inclusive are methyl, ethyl, propyl, isopropyl, t-butyl, n-butyl, pentyl, hexyl, heptyl, octyl, nonyl, decyl, 2-ethylhexyl, 2-methylbutyl, 2-methylpentyl, 1-methylhexyl, 3-methylheptyl and the other isomeric forms thereof.

As used herein, the term "lower alkyl radical" denotes a linear or branched, saturated hydrocarbon-based chain containing from 1 to 5 carbon atoms. Examples of alkyl groups having from 1 to 5 carbon atoms inclusive are methyl, ethyl, propyl, isopropyl, t-butyl, n-butyl, pentyl and the other isomeric forms thereof.

As used herein, the term "alkenyl radical" denotes a linear or branched, unsaturated hydrocarbon-based chain containing from 2 to 10 carbon atoms and comprising one or more double bonds. Examples of alkenyl containing from 2 to 10 carbon atoms are ethenyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl and the isomeric forms thereof.

As used herein, the term "alkynyl radical" denotes a linear or branched, unsaturated hydrocarbon-based chain containing from 2 to 10 carbon atoms and comprising one or more triple bonds. One can cite for instance ethynyl, prop-2-ynyl, but-2-ynyl, but-3-ynyl, pent-2-ynyl, pent-3-ynyl and pent-4-ynyl.

As used herein, the term "substituted alkyl radical" denotes an "alkyl radical" as defined above, i.e. containing from 1 to 10 carbon atoms, substituted with one or more radicals or atoms, such as a halogen atom, an alkoxy radical, a cycloalkyl radical, a heterocycloalkyl radical, a hydroxyl radical, a cyano group, an amine radical, and an amide radical.

As used herein, the term "substituted lower alkyl radical" denotes a "lower alkyl radical" as defined above, i.e. containing from 1 to 5 carbon atoms, substituted with one or more radicals or atoms, such as a halogen atom, an alkoxy radical, a cycloalkyl radical, a heterocycloalkyl radical, a hydroxyl radical, a cyano group, an amine radical, and an amide radical.

As used herein, the term "substituted alkenyl radical" denotes an "alkenyl radical" as defined above substituted with one or more radicals or atoms, such as a halogen atom, an alkoxy radical, a hydroxyl radical, a cyano group, an amine radical, and an amide radical.

As used herein, the term "substituted alkynyl radical" denotes an "alkynyl radical", as defined above, substituted with one or more radicals or atoms, such as a halogen atom, an alkoxy radical, a hydroxyl radical, a cyano group, an amine radical, and an amide radical.

As used herein, the term "cycloalkyl" denotes a cyclic saturated hydrocarbon-based chain containing from 3 to 7 carbon atoms. Mention will be made, in a non-limiting manner, of cyclopropyl, cyclobutyl, cyclopentyl or cyclohexyl radicals.

As used herein, the term "substituted cycloalkyl" denotes a "cycloalkyl", as defined above, substituted with one or more radicals chosen from a halogen atom, an alkoxy radical, a hydroxyl radical, a cyano group, an amine radical, and an amide radical.

As used herein, the term "aryl radical" denotes an aromatic hydrocarbon-based ring or two fused aromatic hydrocarbon-based rings. Examples of aryl radicals include phenyl and naphthyl radicals.

As used herein, the term "substituted aryl radical" denotes an "aryl radical", as defined above, substituted with one or more radicals or atoms, such as an alkyl, a substituted alkyl, an alkoxy, an aryl, a halogen, a hydroxyl, a cyano or a trifluoromethyl.

As used herein, the term "aralkyl radical" denotes an alkyl as defined above substituted with an aryl as defined above.

As used herein, the term "substituted aralkyl radical" denotes an aralkyl as defined above substituted with one or more radicals or atoms, such as a halogen atom, an alkyl radical, a substituted alkyl radical, an aryl, a trifluoromethyl radical, an alkoxy radical, a hydroxyl radical, a cyano group, an amine radical or an amide radical.

As used herein, the term "heterocyclic radical" denotes a saturated or unsaturated, cyclic or polycyclic hydrocarbon-based chain comprising one or more heteroatoms chosen from O, S, and N. Mention will be made, in a non-limiting manner, of morpholine, tetra-2H-pyran, piperidine or piperazine radicals.

As used herein, the term "substituted heterocyclic radical" denotes a heterocyclic radical as defined above substituted with one or more radicals or atoms, such as an alkyl, an alkoxy, a halogen, a hydroxyl, a cyano or a trifluoromethyl.

As used herein, the term "heteroaryl radical" denotes an aromatic heterocyclic radical, i.e. a cyclic or polycyclic aromatic hydrocarbon-based chain, comprising one or more heteroatoms chosen from O, S, and N.

As used herein, the term "substituted heteroaryl radical" denotes a heteroaryl radical as defined above substituted with one or more radicals or atoms, such as an alkyl, an alkoxy, an aryl, a substituted aryl, a halogen, a hydroxyl, a cyano or a trifluoromethyl.

As used herein, the term "heteroaralkyl radical" denotes an alkyl radical as defined above substituted with a heteroaryl radical as defined above.

As used herein, the term "substituted heteroaralkyl radical" denotes a heteroaralkyl radical as defined above substituted with one or more radicals or atoms, such as an alkyl, an alkoxy, a halogen, a hydroxyl, a cyano or a trifluoromethyl.

As used herein, the term "alkoxy radical" denotes an oxygen atom substituted with an alkyl radical as defined above. The alkyl radical may be branched, linear, substituted, or unsubstituted.

As used herein, the term "substituted alkoxy radical" denotes an alkoxy radical as defined above substituted by with one or more radicals, such as an alkenyl radical, a halogen atom, a cycloalkyl radical, a heterocycloalkyl radical, a hydroxyl radical, a cyano group, an amine radical, and an amide radical.

As used herein, the term "halogen atom" denotes a fluorine, chlorine, bromine, or iodine atom.

As used herein, the term "amine radical" may be a primary, secondary or tertiary amine radical. The amine radical may be branched, linear, substituted, or unsubstituted.

As used herein, the term "substituted amine radical" denotes an amine radical as defined above substituted with one or more radicals.

As used herein, the term "cyclic amine" denotes a radical in which the nitrogen has been incorporated into a ring structure.

As used herein, the term "heterocyclic amine" denotes a saturated or unsaturated cyclic amine comprising one or more heteroatoms, such as O, S, or N.

As used herein, the term "amide radical" may be a primary, secondary or tertiary amide radical.

In one embodiment, the present invention provides compounds of formula (I) in which:

$R_1$ is a lower alkyl radical, a substituted lower alkyl radical, an alkenyl radical, a substituted alkenyl radical, an alkynyl radical, a substituted alkynyl radical, an alkoxy radical, a substituted alkoxy radical, a cycloalkyl radical, a substituted cycloalkyl radical, a heterocyclic radical, a substituted heterocyclic radical, an amine radical, a substituted amine radical, a cyclic amine radical, or a heterocyclic amine radical;

$R_2$ is a hydrogen atom, a lower alkyl radical, a lower alkyl radical substituted with a halogen atom or a lower alkyl radical substituted with an alkoxy radical, $R_3$ is a hydrogen atom, a lower alkyl radical, a substituted lower alkyl radical, an alkynyl radical, a substituted alkynyl radical, an alkoxy radical, a halogen atom, or a nitrile radical; and n is 0 or 1.

In another embodiment, the compounds of formula (I) are those for which:

$R_1$ is a lower alkyl radical, a substituted lower alkyl radical, a cycloalkyl radical, a substituted cycloalkyl radical, a heterocyclic radical, a substituted heterocyclic radical, an alkoxy radical comprising a lower alkyl radical or a substituted amine radical comprising a lower alkyl radical;

$R_2$ is a hydrogen atom, a lower alkyl radical substituted with a fluorine atom; or a lower alkyl radical substituted with an alkoxy radical;

$R_3$ is a hydrogen atom, a lower alkyl radical containing 1 to 3 carbon atoms; a methoxy radical, or an ethoxy radical, a fluorine atom, or a nitrile radical; and n is 0 or 1.

In a preferred embodiment, the compounds having formula (I) include but are not limited to the compounds shown in Table 1 below.

TABLE 1

| Example number | Structure | Name |
|---|---|---|
| 1 | 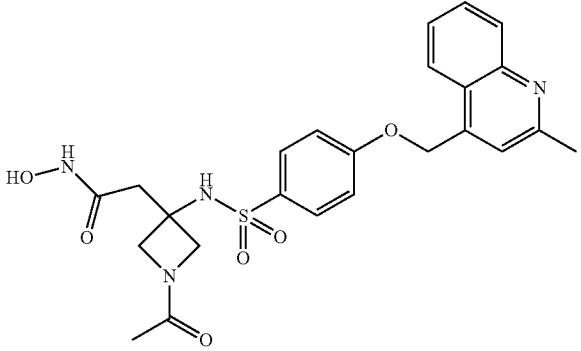 | 2-(1-acetyl-3-((4-((2-methylquinolin-4-yl)methoxy)phenyl)sulfonamido)azetidin-3-yl)-N-hydroxyacetamide |

TABLE 1-continued

| Example number | Structure | Name |
|---|---|---|
| 2 | 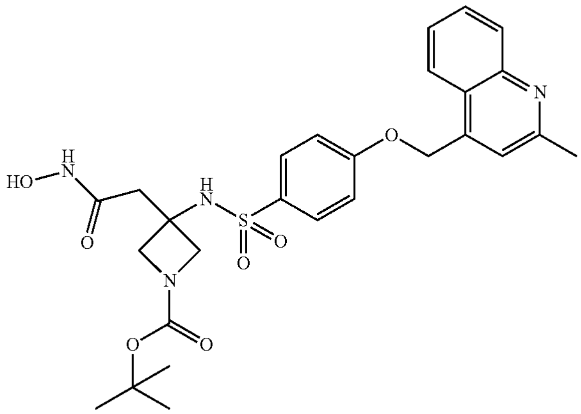 | tert-butyl 3-(2-(hydroxyamino)-2-oxoethyl)-3-((4-((2-methylquinolin-4-yl)methoxy)phenyl)sulfonamido)azetidine-1-carboxylate |
| 3 | 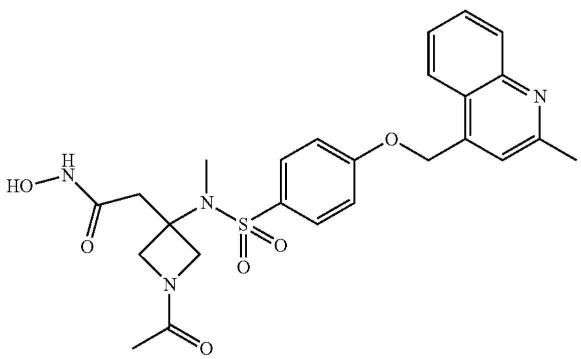 | 2-(1-acetyl-3-((N-methyl-4-((2-methylquinolin-4-yl)methoxy)phenyl)sulfonamido)azetidin-3-yl)-N-hydroxyacetamide |
| 4a | 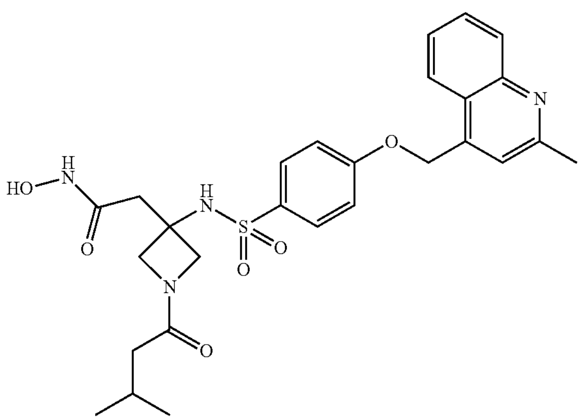 | N-hydroxy-2-(1-(3-methylbutanoyl)-3-((4-((2-methylquinolin-4-yl)methoxy)phenyl)sulfonamido)azetidin-3-yl)acetamide |
| 4b | 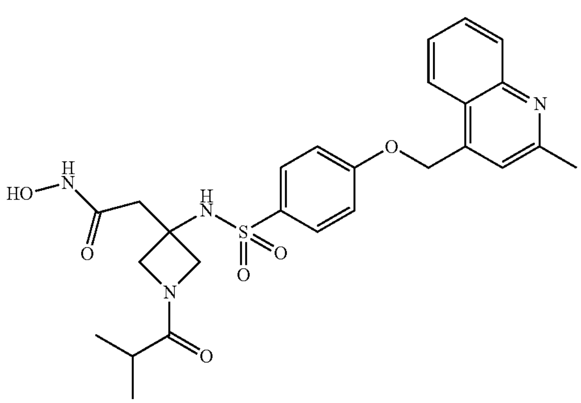 [SMILES: Cc1cc(COc2ccc(S(=O)(=O)NC3(CC(=O)NO)CN(C(=O)C(C)C)C3)cc2)c2ccccc2n1] | N-hydroxy-2-(1-isobutyryl-3-((4((2-methylquinolin-4-yl)methoxy)phenyl)sulfonamido)azetidin-3-yl)acetamide |

TABLE 1-continued

| Example number | Structure | Name |
|---|---|---|
| 4c | 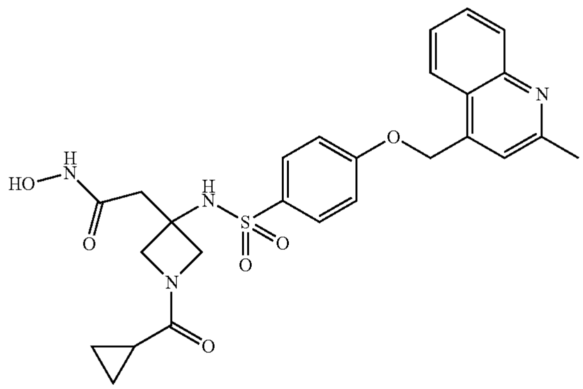 [SMILES: Cc1cc(COc2ccc(S(=O)(=O)NC3(CC(=O)NO)CN(C(=O)C4CC4)C3)cc2)c2ccccc2n1] | 2-(1-(cyclopropanecarbonyl)-3-((4-((2-methylquinolin-4-yl)methoxy)phenyl)sulfonamido)azetidin-3-yl)-N-hydroxyacetamide |
| 4d | 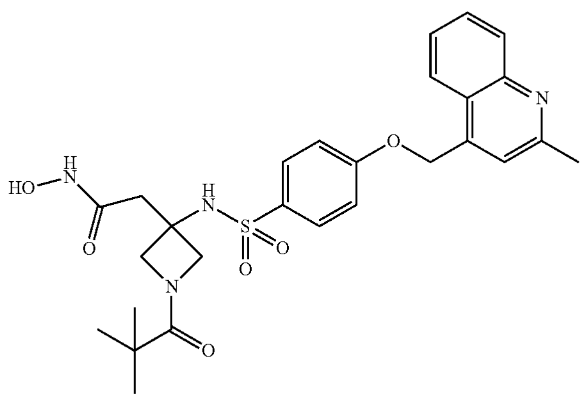 | N-hydroxy-2-(3-((4-((2-methylquinolin-4-yl)methoxy)phenyl)sulfonamido)-1-pivaloylazetidin-3-yl)acetamide |
| 4e | 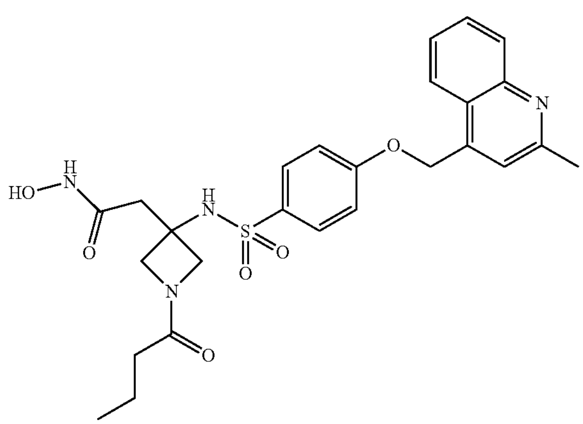 | 2-(1-butyryl-3-((4-((2-methylquinolin-4-yl)methoxy)phenyl)sulfonamido)azetidin-3-yl)-N-hydroxyacetamide |

TABLE 1-continued

| Example number | Structure | Name |
|---|---|---|
| 4f | 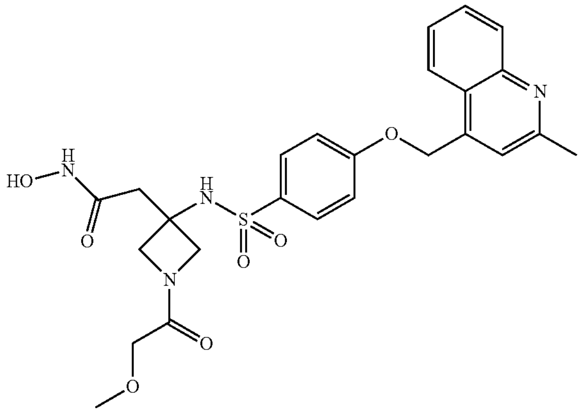 | N-hydroxy-2-(1-(2-methoxyacetyl)-3-((4-((2-methylquinolin-4-yl)methoxy)phenyl)sulfonamido)azetidin-3-yl)acetamide |
| 4g | 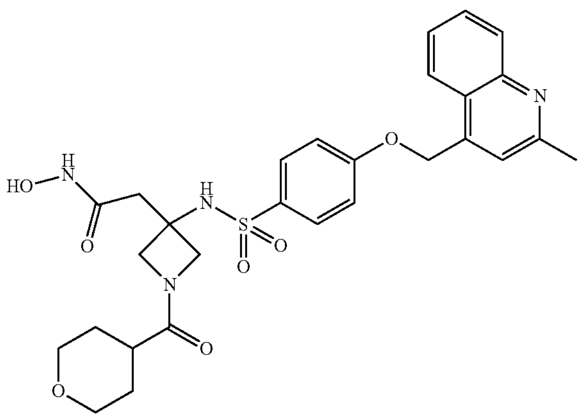 | N-hydroxy-2-(3-((4-((2-methylquinolin-4-yl)methoxy)phenyl)sulfonamido)-1-(tetrahydro-2H-pyran-4-carbonyl)azetidin-3-yl)acetamide |
| 4h | 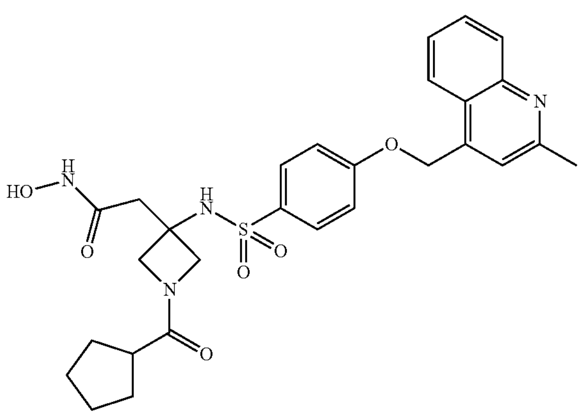 [SMILES: Cc1cc(COc2ccc(S(=O)(=O)NC3(CC(=O)NO)CN(C(=O)C4CCCC4)C3)cc2)c2ccccc2n1] | 2-(1-(cyclopentanecarbonyl)-3-((4-((2-methylquinolin-4-yl)methoxy)phenyl)sulfonamido)azetidin-3-yl)-N-hydroxyacetamide |

TABLE 1-continued

| Example number | Structure | Name |
|---|---|---|
| 4i | 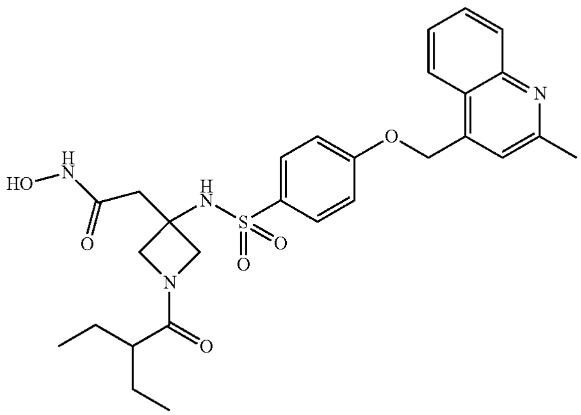 [SMILES: CCC(CC)C(=O)N1CC(CC(=O)NO)(NS(=O)(=O)c2ccc(OCc3cc(C)nc4ccccc34)cc2)C1] | 2-(1-(2-ethylbutanoyl)-3-((4-((2-methylquinolin-4-yl)methoxy)phenyl)sulfonamido)azetidin-3-yl)-N-hydroxyacetamide |
| 4j | 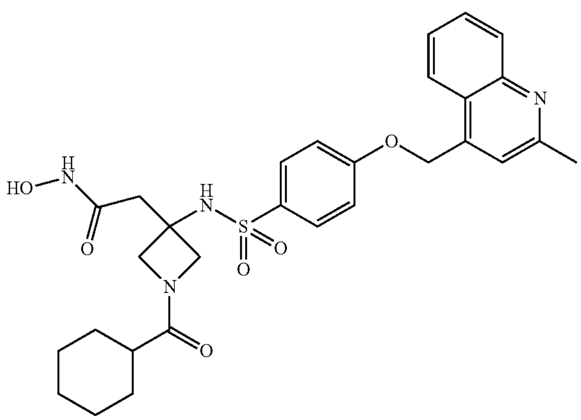 | 2-(1-(cyclohexanecarbonyl)-3-((4-((2-methylquinolin-4-yl)methoxy)phenyl)sulfonamido)azetidin-3-yl)-N-hydroxyacetamide |
| 5a | 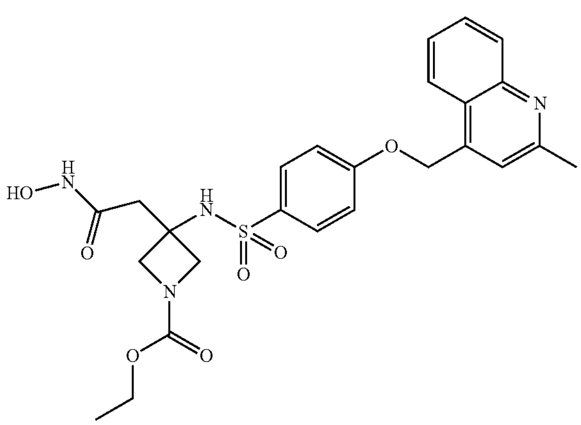 | ethyl 3-(2-(hydroxyamino)-2-oxoethyl)-3-((4-((2-methylquinolin-4-yl)methoxy)phenyl)sulfonamido)azetidine-1-carboxylate |

TABLE 1-continued

| Example number | Structure | Name |
|---|---|---|
| 5b | 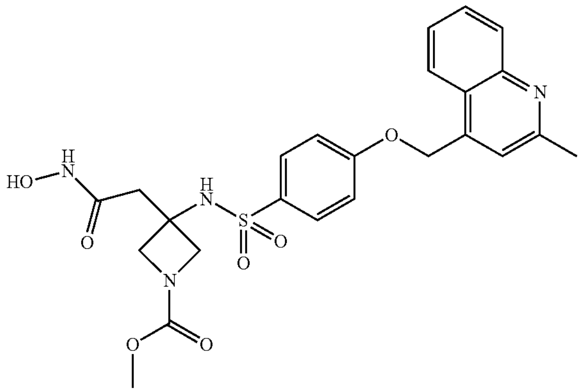 [SMILES: COC(=O)N1CC(CC(=O)NO)(NS(=O)(=O)c2ccc(OCc3cc(C)nc4ccccc34)cc2)C1] | methyl 3-(2-(hydroxyamino)-2-oxoethyl)-3-((4-((2-methylquinolin-4-yl)methoxy)phenyl)sulfonamido)azetidine-1-carboxylate |
| 5c | 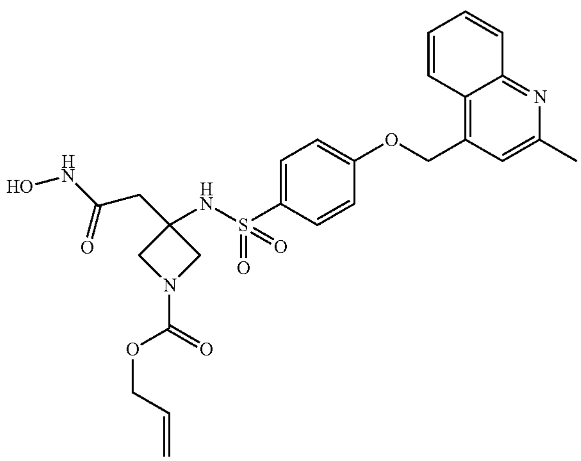 [SMILES: C=CCOC(=O)N1CC(CC(=O)NO)(NS(=O)(=O)c2ccc(OCc3cc(C)nc4ccccc34)cc2)C1] | allyl 3-(2-(hydroxyamino)-2-oxoethyl)-3-((4-((2-methylquinolin-4-yl)methoxy)phenyl)sulfonamido)azetidine-1-carboxylate |
| 5d | 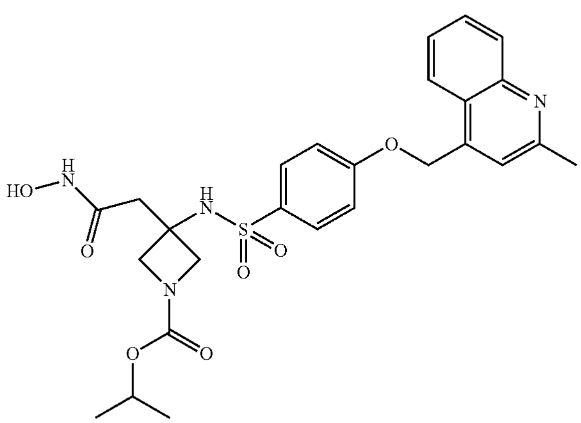 [SMILES: Cc1cc(COc2ccc(S(=O)(=O)NC3(CC(=O)NO)CN(C(=O)OC(C)C)C3)cc2)c2ccccc2n1] | isopropyl 3-(2-(hydroxyamino)-2-oxoethyl)-3-((4-((2-methylquinolin-4-yl)methoxy)phenyl)sulfonamido)azetidine-1-carboxylate |

TABLE 1-continued

| Example number | Structure | Name |
|---|---|---|
| 6 | 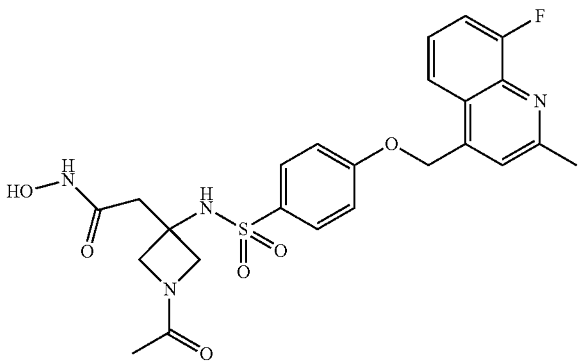 [SMILES: CC(=O)N1CC(CC(=O)NO)(NS(=O)(=O)c2ccc(OCc3cc(C)nc4c(F)cccc34)cc2)C1] | 2-(1-acetyl-3-((4-((8-fluoro-2-methylquinolin-4-yl)methoxy)phenyl)sulfonamido)azetidin-3-yl)-N-hydroxyacetamide |
| 7a | 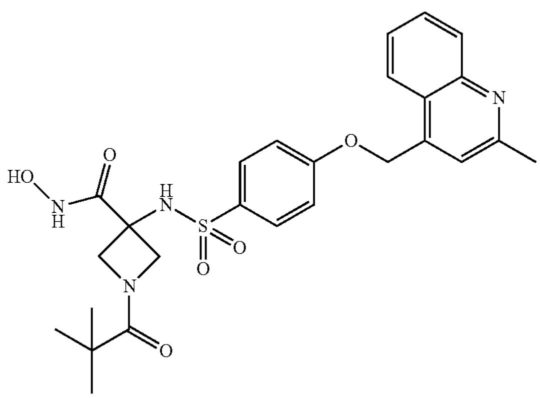 [SMILES: Cc1cc(COc2ccc(S(=O)(=O)NC3(C(=O)NO)CN(C(=O)C(C)(C)C)C3)cc2)c2ccccc2n1] | N-hydroxy-3-((4-((2-methylquinolin-4-yl)methoxy)phenyl)sulfonamido)-1-pivaloylazetidine-3-carboxamide |
| 7b | 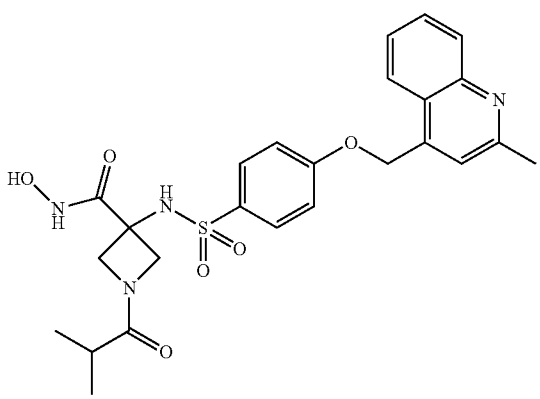 [SMILES: Cc1cc(COc2ccc(S(=O)(=O)NC3(C(=O)NO)CN(C(=O)C(C)C)C3)cc2)c2ccccc2n1] | N-hydroxy-1-isobutyryl-3-((4-((2-methylquinolin-4-yl)methoxy)phenyl)sulfonamido)azetidine-3-carboxamide |
| 7c | 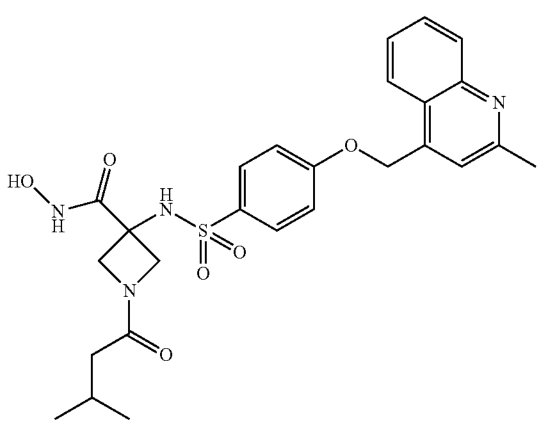 [SMILES: Cc1cc(COc2ccc(S(=O)(=O)NC3(C(=O)NO)CN(C(=O)CC(C)C)C3)cc2)c2ccccc2n1] | N-hydroxy-1-(3-methylbutanoyl)-3-((4-((2-methylquinolin-4-yl)methoxy)phenyl)sulfonamido)azetidine-3-carboxamide |

TABLE 1-continued

| Example number | Structure | Name |
|---|---|---|
| 7d | 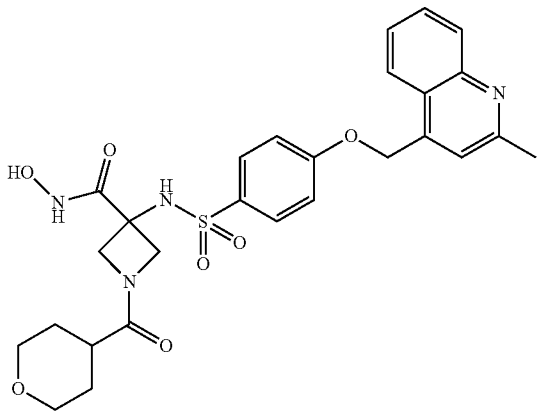 [SMILES: Cc1cc(COc2ccc(S(=O)(=O)NC3(C(=O)NO)CN(C(=O)C4CCOCC4)C3)cc2)c2ccccc2n1] | N-hydroxy-3-((4-((2-methylquinolin-4-yl)methoxy)phenyl)sulfonamido)-1-(tetrahydro-2H-pyran-4-carbonyl)azetidine-3-carboxamide |
| 7e | 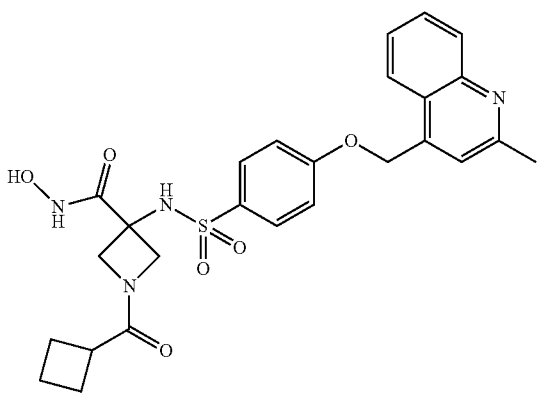 [SMILES: Cc1cc(COc2ccc(S(=O)(=O)NC3(C(=O)NO)CN(C(=O)C4CCC4)C3)cc2)c2ccccc2n1] | 1-(cyclobutanecarbonyl)-N-hydroxy-3-((4-((2-methylquinolin-4-yl)methoxy)phenyl)sulfonamido)azetidine-3-carboxamide |
| 7f | 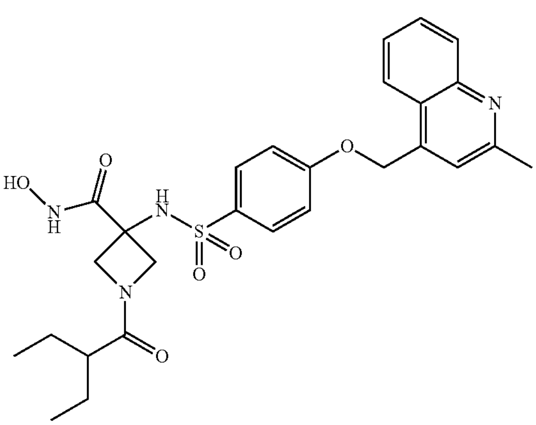 [SMILES: CCC(CC)C(=O)N1CC(NS(=O)(=O)c2ccc(OCc3cc(C)nc4ccccc34)cc2)(C(=O)NO)C1] | 1-(2-ethylbutanoyl)-N-hydroxy-3-((4-((2-methylquinolin-4-yl)methoxy)phenyl)sulfonamido)azetidine-3-carboxamide |

TABLE 1-continued
| Example number | Structure | Name |
|---|---|---|
| 7g | 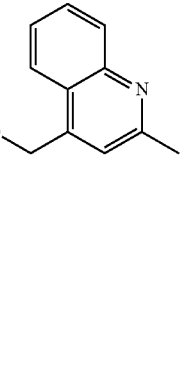 | N-hydroxy-3-((4-((2-methylquinolin-4-yl)methoxy)phenyl)sulfonamido)-1-propionylazetidine-3-carboxamide |
| 7h | 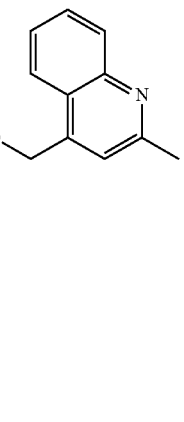 | 1-butyryl-N-hydroxy-3-((4-((2-methylquinolin-4-yl)methoxy)phenyl)sulfonamido)azetidine-3-carboxamide |
| 7i | 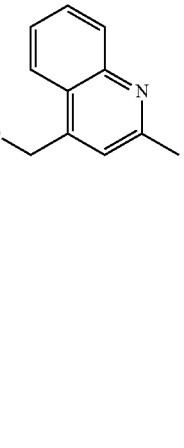 | N-hydroxy-3-((4-((2-methylquinolin-4-yl)methoxy)phenyl)sulfonamido)-1-pentanoylazetidine-3-carboxamide |

TABLE 1-continued

| Example number | Structure | Name |
|---|---|---|
| 8 | 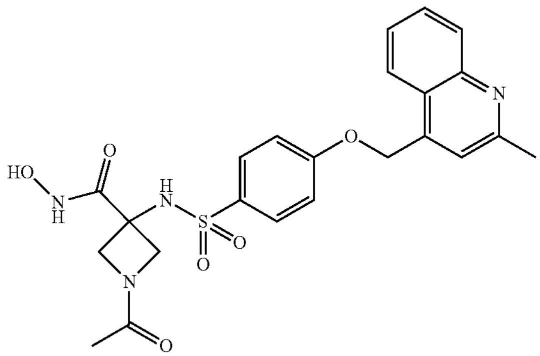 [SMILES: CC(=O)N1CC(NS(=O)(=O)c2ccc(OCc3cc(C)nc4ccccc34)cc2)(C(=O)NO)C1] | 1-acetyl-N-hydroxy-3-((4-((2-methylquinolin-4-yl)methoxy)phenyl)sulfonamido)azetidine-3-carboxamide |
| 9 | 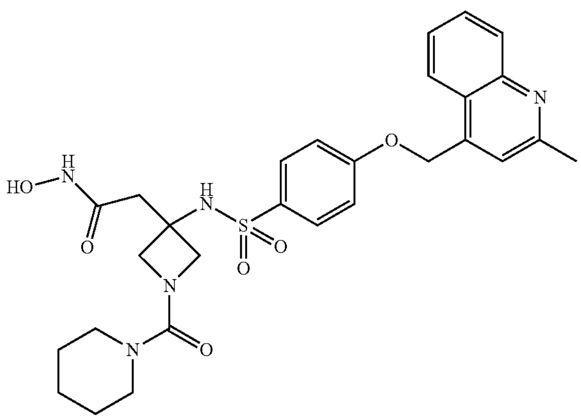 | N-hydroxy-2-(3-((4-((2-methylquinolin-4-yl)methoxy)phenyl)sulfonamido)-1-(piperidine-1-carbonyl)azetidin-3-yl)acetamide |
| 10 | 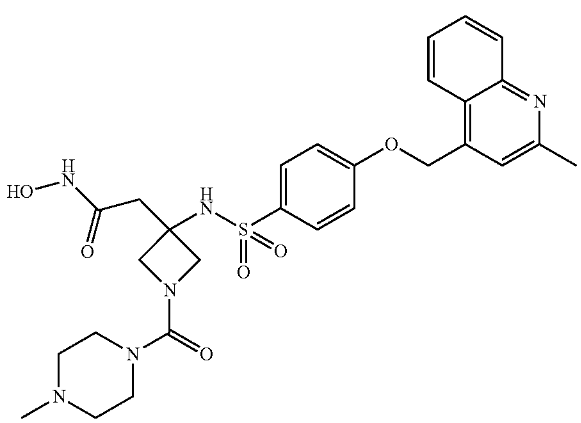 | N-hydroxy-2-(1-(4-methylpiperazine-1-carbonyl)-3-((4-((2-methylquinolin-4-yl)methoxy)phenyl)sulfonamido)azetidin-3-yl)acetamide |

TABLE 1-continued

| Example number | Structure | Name |
|---|---|---|
| 11 | 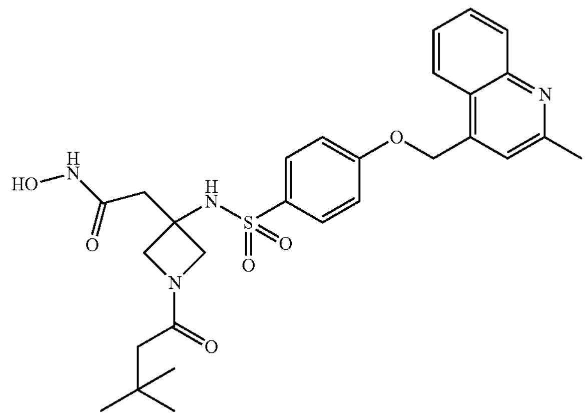 [SMILES: Cc1cc(COc2ccc(S(=O)(=O)NC3(CC(=O)NO)CN(C(=O)CC(C)(C)C)C3)cc2)c2ccccc2n1] | 2-(1-(3,3-dimethylbutanoyl)-3-((4-((2-methylquinolin-4-yl)methoxy)phenyl)sulfonamido)azetidin-3-yl)-N-hydroxyacetamide |
| 12 | 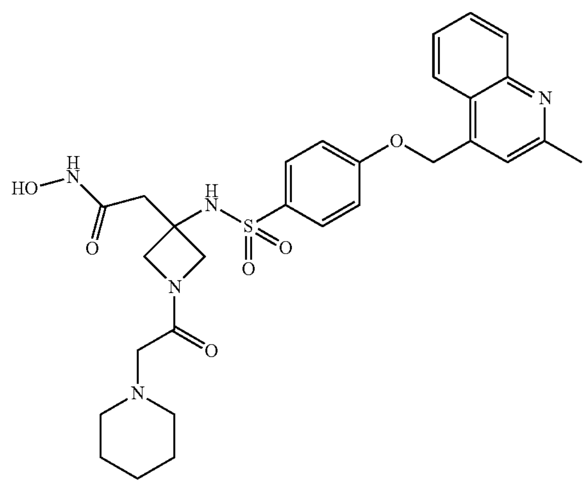 [SMILES: Cc1cc(COc2ccc(S(=O)(=O)NC3(CC(=O)NO)CN(C(=O)CN4CCCCC4)C3)cc2)c2ccccc2n1] | N-hydroxy-2-(3-((4-((2-methylquinolin-4-yl)methoxy)phenyl)sulfonamido)-1-(2-(piperidin-1-yl)acetyl)azetidin-3-yl)acetamide |
| 13 | 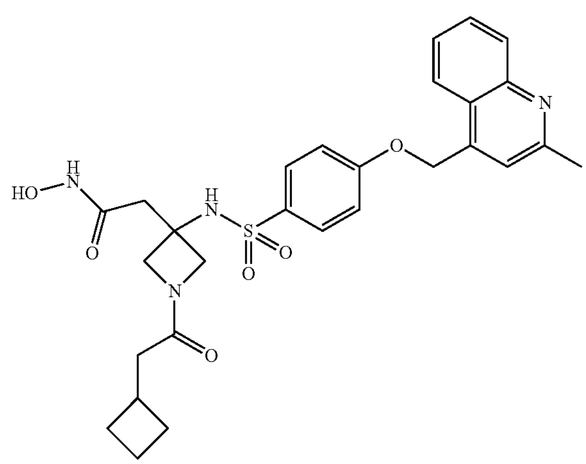 [SMILES: Cc1cc(COc2ccc(S(=O)(=O)NC3(CC(=O)NO)CN(C(=O)CC4CCC4)C3)cc2)c2ccccc2n1] | 2-(1-(2-cyclobutylacetyl)-3-((4-((2-methylquinolin-4-yl)methoxy)phenyl)sulfonamido)azetidin-3-yl)-N-hydroxyacetamide |

TABLE 1-continued
| Example number | Structure | Name |
|---|---|---|
| 14 | 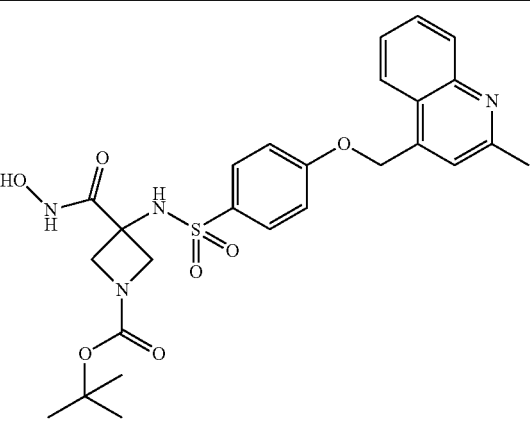 | tert-butyl 3-(hydroxycarbamoyl)-3-((4-((2-methylquinolin-4-yl)methoxy)phenyl)sulfonamido)azetidine-1-carboxylate |
| 15 | 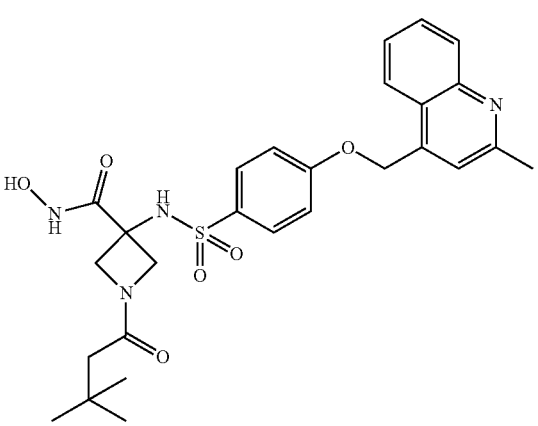 [SMILES: Cc1cc(COc2ccc(S(=O)(=O)NC3(C(=O)NO)CN(C(=O)CC(C)(C)C)C3)cc2)c2ccccc2n1] | 1-(3,3-dimethylbutanoyl)-N-hydroxy-3-((4-((2-methylquinolin-4-yl)methoxy)phenyl)sulfonamido)azetidine-3-carboxamide |
| 16a | 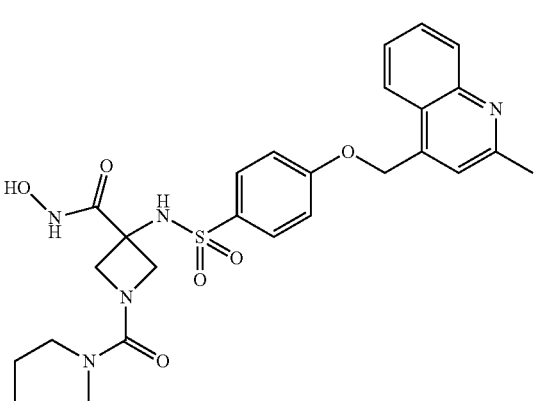 | N-hydroxy-3-((4-((2-methylquinolin-4-yl)methoxy)phenyl)sulfonamido)-1-(piperidine-1-carbonyl)azetidine-3-carboxamide |

TABLE 1-continued

| Example number | Structure | Name |
|---|---|---|
| 16b | 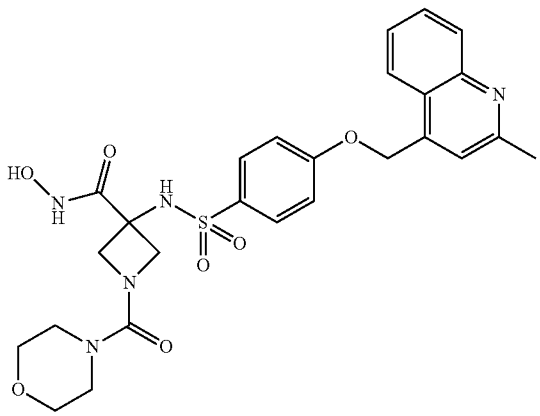 [SMILES: Cc1cc(COc2ccc(S(=O)(=O)NC3(C(=O)NO)CN(C(=O)N4CCOCC4)C3)cc2)c2ccccc2n1] | N-hydroxy-3-((4-((2-methylquinolin-4-yl)methoxy)phenyl)sulfonamido)-1-(morpholine-4-carbonypazetidine-3-carboxamide |
| 16c | 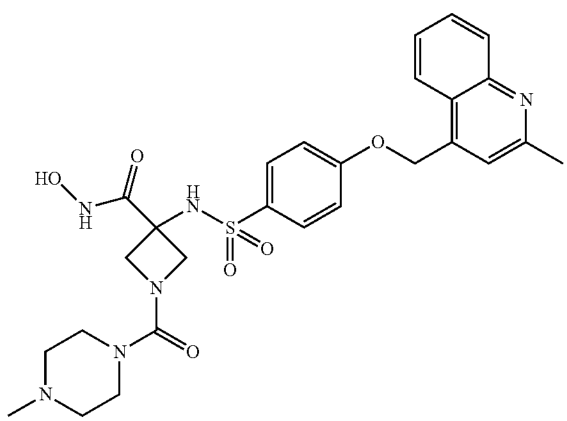 | N-hydroxy-1-(4-methylpiperazine-1-carbonyl)-3-((4-((2-methylquinolin-4-yl)methoxy)phenyl)sulfonamido)azetidine-3-carboxamide |
| 17 | 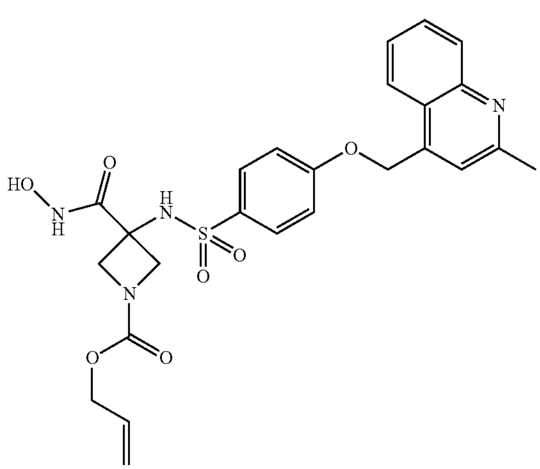 [SMILES: C=CCOC(=O)N1CC(NS(=O)(=O)c2ccc(OCc3cc(C)nc4ccccc34)cc2)(C(=O)NO)C1] | ally 3-(hydroxycarbamoyl)-3-((4-((2-methylquinolin-4-yl)methoxy)phenyl)sulfonamido)azetidine-1-carboxylate |

TABLE 1-continued

| Example number | Structure | Name |
|---|---|---|
| 18 | 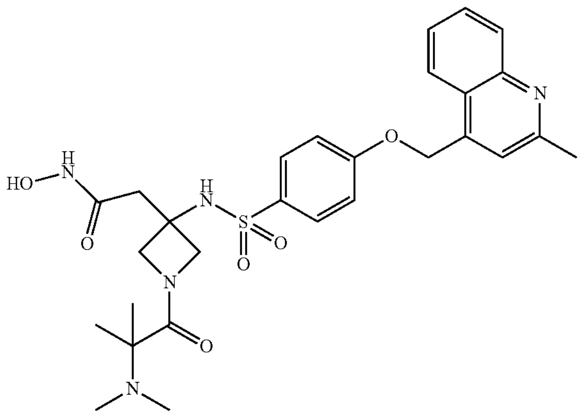 [SMILES: Cc1cc(COc2ccc(S(=O)(=O)NC3(CC(=O)NO)CN(C(=O)C(C)(C)N(C)C)C3)cc2)c2ccccc2n1] | 2-(1-(2-(dimethylamino)-2-methylpropanoyl)-3-((4-((2-methylquinolin-4-yl)methoxy)phenyl)sulfonamido)azetidin-3-yl)-N-hydroxyacetamide |
| 19a | 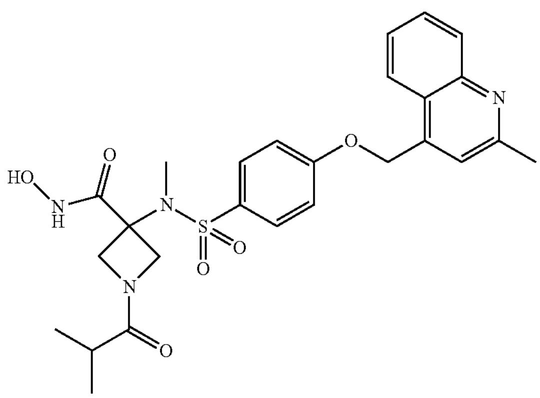 [SMILES: Cc1cc(COc2ccc(S(=O)(=O)N(C)C3(C(=O)NO)CN(C(=O)C(C)C)C3)cc2)c2ccccc2n1] | N-hydroxy-1-isobutyryl-3-((N-methyl-4-((2-methylquinolin-4-yl)methoxy)phenyl)sulfonamido)azetidine-3-carboxamide |
| 19b | 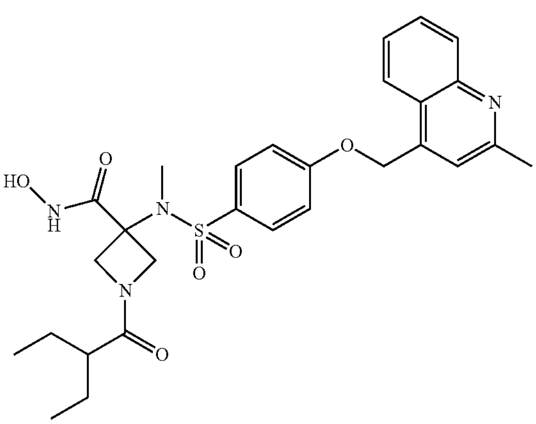 [SMILES: CCC(CC)C(=O)N1CC(C(=O)NO)(N(C)S(=O)(=O)c2ccc(OCc3cc(C)nc4ccccc34)cc2)C1] | 1-(2-ethylbutanoyl)-N-hydroxy-3-((N-methyl-4-((2-methylquinolin-4-yl)methoxy)phenyl)sulfonamido)azetidine-3-carboxamide |

TABLE 1-continued

| Example number | Structure | Name |
|---|---|---|
| 19c | 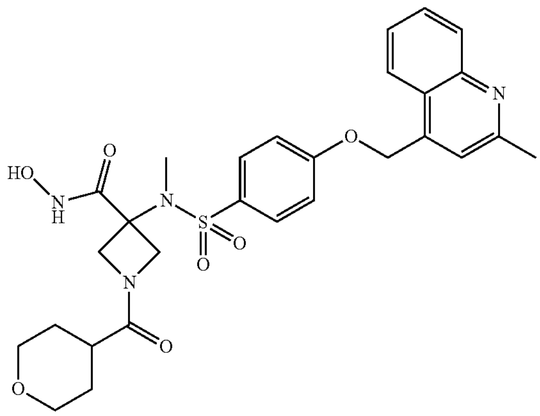 [SMILES: Cc1cc(COc2ccc(S(=O)(=O)N(C)C3(C(=O)NO)CN(C(=O)C4CCOCC4)C3)cc2)c2ccccc2n1] | N-hydroxy-3-((N-methyl-4-((2-methylquinolin-4-yl)methoxy)phenyl)sulfonamido)-1-(tetrahydro-2H-pyran-4-carbonyl)azetidine-3-carboxamide |
| 19d | 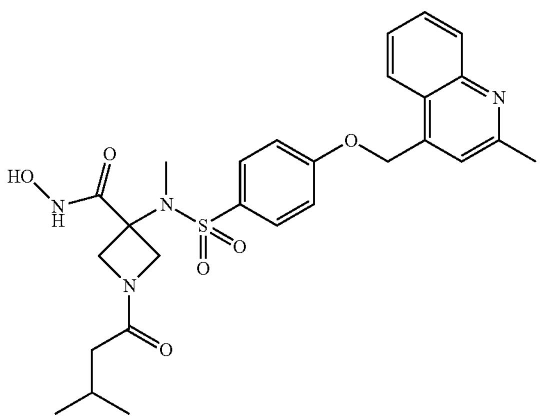 [SMILES: Cc1cc(COc2ccc(S(=O)(=O)N(C)C3(C(=O)NO)CN(C(=O)CC(C)C)C3)cc2)c2ccccc2n1] | N-hydroxy-3-((N-methyl-4-((2-methylquinolin-4-yl)methoxy)phenyl)sulfonamido)-1-(3-methylbutanoyl)azetidine-3-carboxamide |
| 20 | 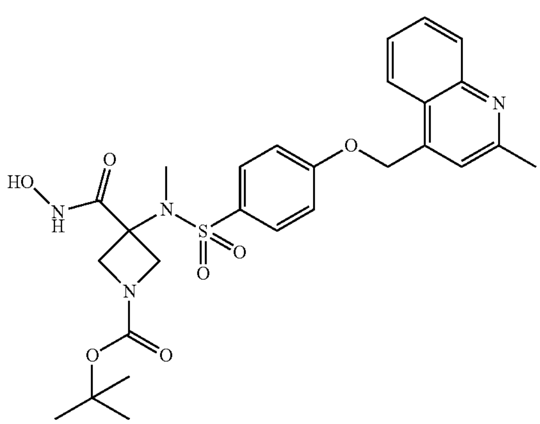 [SMILES: Cc1cc(COc2ccc(S(=O)(=O)N(C)C3(C(=O)NO)CN(C(=O)OC(C)(C)C)C3)cc2)c2ccccc2n1] | tert-butyl 3-(hydroxycarbamoyl)-3-((N-methyl-4-((2-methylquinolin-4-yl)methoxy)phenyl)sulfonamido)azetidine-1-carboxylate |

TABLE 1-continued

| Example number | Structure | Name |
|---|---|---|
| 21a | 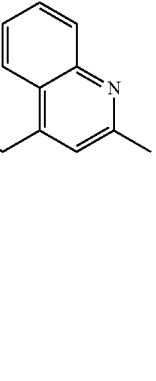 | 3-((N-ethyl-4-((2-methylquinolin-4-yl)methoxy)phenyl)sulfonamido)-N-hydroxy-1-isobutyrylazetidine-3-carboxamide |
| 21b | 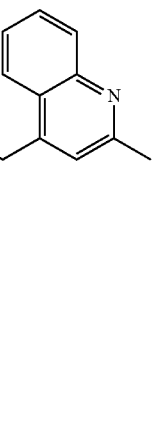 | 3-((N-ethyl-4-((2-methylquinolin-4-yl)methoxy)phenyl)sulfonamido)-N-hydroxy-1-(tetrahydro-2H-pyran-4-carbonyl)azetidine-3-carboxamide |
| 22 | 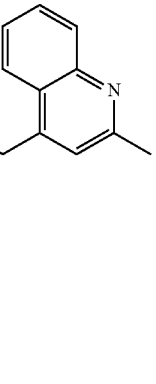 | N-hydroxy-1-isobutyryl-3-((N-(2-methoxyethyl)-4-((2-methylquinolin-4-yl)methoxy)phenyl)sulfonamido)azetidine-3-carboxamide |
| 23 | 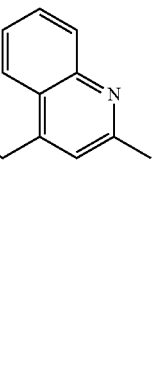 | N-hydroxy-1-isobutyryl-3-((N-isopropyl-4-((2-methylquinolin-4-yl)methoxy)phenyl)sulfonamido)azetidine-3-carboxamide |

TABLE 1-continued

| Example number | Structure | Name |
|---|---|---|
| 24 | 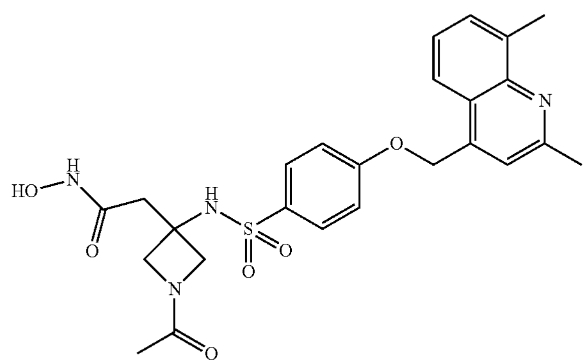 [SMILES: CC(=O)N1CC(CC(=O)NO)(NS(=O)(=O)c2ccc(OCc3cc(C)nc4c(C)cccc34)cc2)C1] | 2-(1-acetyl-3-((4-((2,8-dimethylquinolin-4-yl)methoxy)phenyl)sulfonamido)azetidin-3-yl)-N-hydroxyacetamide |
| 25 | 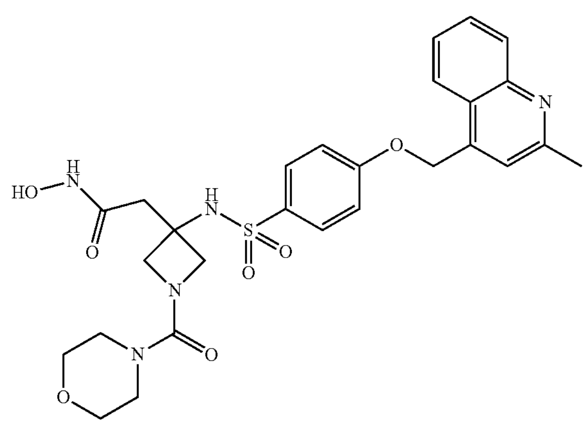 | N-hydroxy-2-(3-((4-((2-methylquinolin-4-yl)methoxy)phenyl)sulfonamido)-1-(morpholine-4-carbonyl)azetidin-3-yl)acetamide |
| 26a | 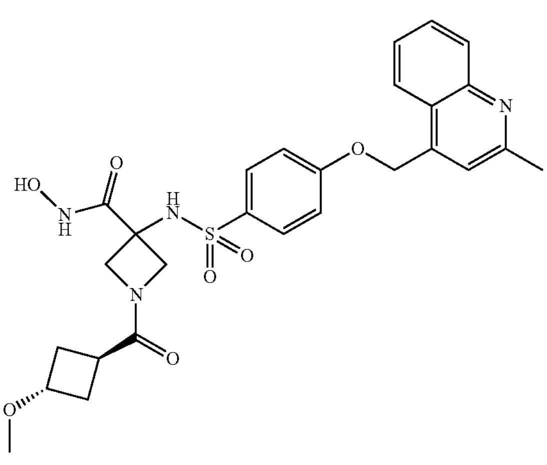 [SMILES: CO[C@H]1C[C@H](C(=O)N2CC(NS(=O)(=O)c3ccc(OCc4cc(C)nc5ccccc45)cc3)(C(=O)NO)C2)C1] | N-hydroxy-1-((1r,3r)-3-methoxycyclobutane-1-carbonyl)-3-((4-((2-methylquinolin-4-yl)methoxy)phenyl)sulfonamido)azetidine-3-carboxamide |

TABLE 1-continued

| Example number | Structure | Name |
|---|---|---|
| 26b | 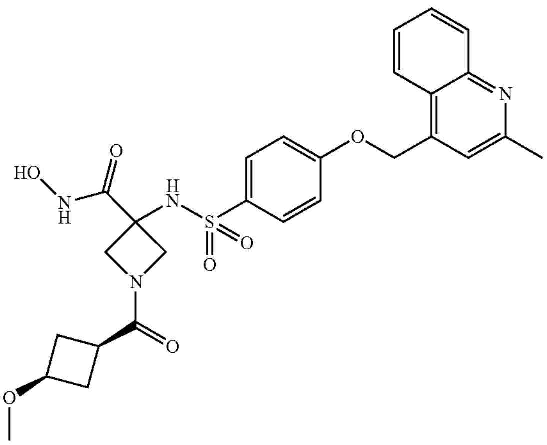 [SMILES: CO[C@H]1C[C@@H](C(=O)N2CC(NS(=O)(=O)c3ccc(OCc4cc(C)nc5ccccc45)cc3)(C(=O)NO)C2)C1] | N-hydroxy-1-((1s,3s)-3-methoxycyclobutane-1-carbonyl)-3-((4-((2-methylquinolin-4-yl)methoxy)phenyl)sulfonamido)azetidine-3-carboxamide |
| 26c | 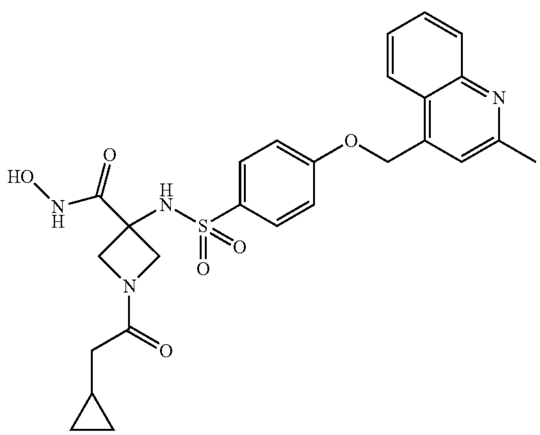 [SMILES: Cc1cc(COc2ccc(S(=O)(=O)NC3(C(=O)NO)CN(C(=O)CC4CC4)C3)cc2)c2ccccc2n1] | 1-(2-cyclopropylacetyl)-N-hydroxy-3-((4-((2-methylquinolin-4-yl)methoxy)phenyl)sulfonamido)azetidine-3-carboxamide |
| 26d | 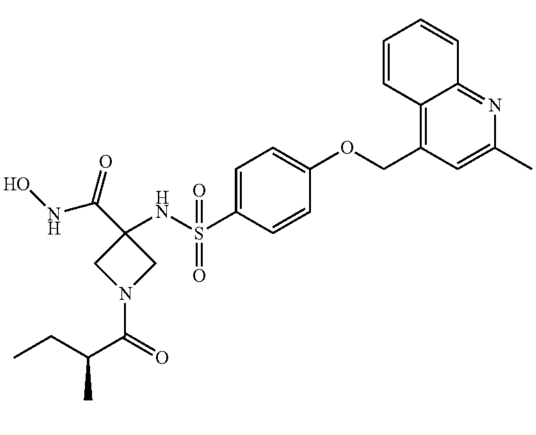 [SMILES: CC[C@H](C)C(=O)N1CC(NS(=O)(=O)c2ccc(OCc3cc(C)nc4ccccc34)cc2)(C(=O)NO)C1] | (S)-N-hydroxy-1-(2-methylbutanoyl)-3-((4-((2-methylquinolin-4-yl)methoxy)phenyl)sulfonamido)azetidine-3-carboxamide |

TABLE 1-continued

| Example number | Structure | Name |
|---|---|---|
| 26e | 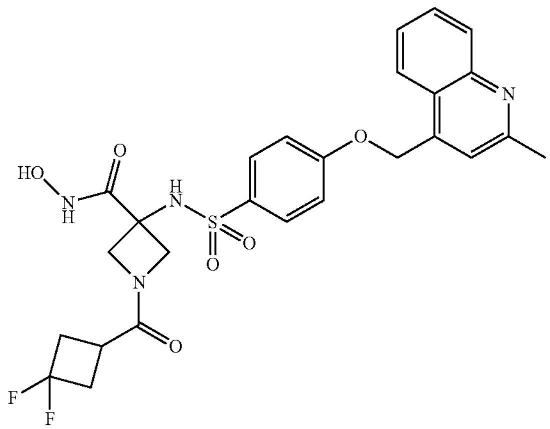 [SMILES: Cc1cc(COc2ccc(S(=O)(=O)NC3(C(=O)NO)CN(C(=O)C4CC(F)(F)C4)C3)cc2)c2ccccc2n1] | 1-(3,3-difluorocyclobutane-1-carbonyl)-N-hydroxy-3-((4-((2-methylquinolin-4-yl)methoxy)phenyl)sulfonamido)azetidine-3-carboxamide |
| 26f | 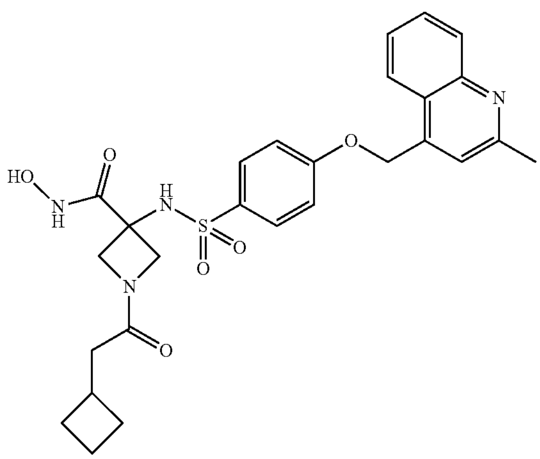 [SMILES: Cc1cc(COc2ccc(S(=O)(=O)NC3(C(=O)NO)CN(C(=O)CC4CCC4)C3)cc2)c2ccccc2n1] | 1-(2-cyclobutylacetyl)-N-hydroxy-3-((4-((2-methylquinolin-4-yl)methoxy)phenyl)sulfonamido)azetidine-3-carboxamide |
| 27 | 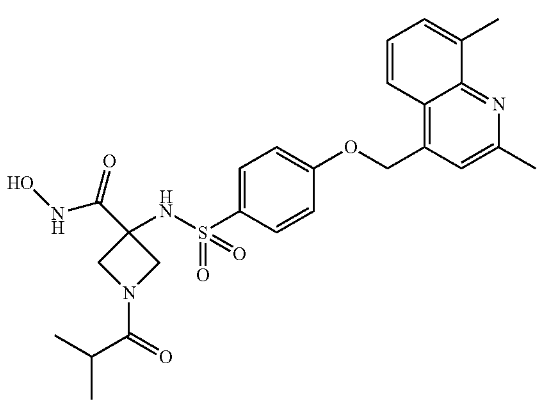 [SMILES: Cc1cc(COc2ccc(S(=O)(=O)NC3(C(=O)NO)CN(C(=O)C(C)C)C3)cc2)c2cccc(C)c2n1] | 3-((4-((2,8-dimethylquinolin-4-yl)methoxy)phenyl)sulfonamido)-N-hydroxy-1-isobutyrylazetidine-3-carboxamide |

TABLE 1-continued

| Example number | Structure | Name |
|---|---|---|
| 28a | 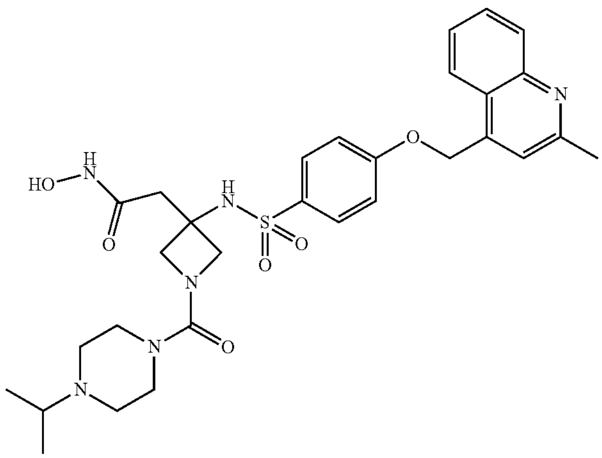 [SMILES: Cc1cc(COc2ccc(S(=O)(=O)NC3(CC(=O)NO)CN(C(=O)N4CCN(C(C)C)CC4)C3)cc2)c2ccccc2n1] | N-hydroxy-2-(1-(4-isopropylpiperazine-1-carbonyl)-3-((4((2-methylquinolin-4-yl)methoxy)phenyl)sulfonamido)azetidin-3-yl)acetamide |
| 28b | 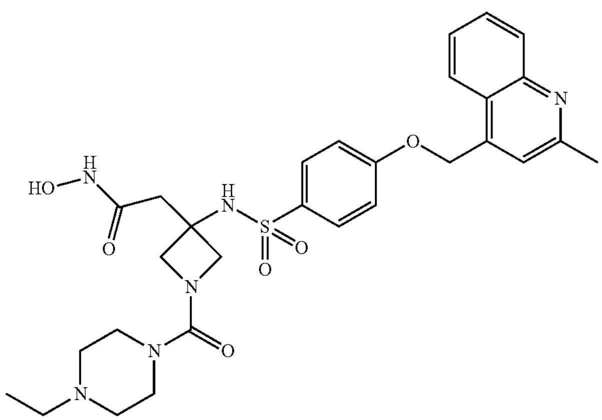 [SMILES: CCN1CCN(C(=O)N2CC(CC(=O)NO)(NS(=O)(=O)c3ccc(OCc4cc(C)nc5ccccc45)cc3)C2)CC1] | 2-(1-(4-ethylpiperazine-1-carbonyl)-3-((4-((2-methylquinolin-4-yl)methoxy)phenyl)sulfonamido)azetidin-3-yl)-N-hydroxyacetamide |
| 29 | 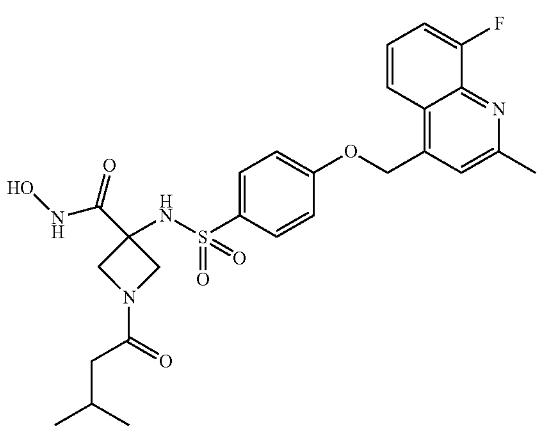 [SMILES: Cc1cc(COc2ccc(S(=O)(=O)NC3(C(=O)NO)CN(C(=O)CC(C)C)C3)cc2)c2cccc(F)c2n1] | 3-((4-((8-fluoro-2-methylquinolin-4-yl)methoxy)phenyl)sulfonamido)-N-hydroxy-1-(3-methylbutanoyl)azetidine-3-carboxamide |

TABLE 1-continued

| Example number | Structure | Name |
|---|---|---|
| 30 | 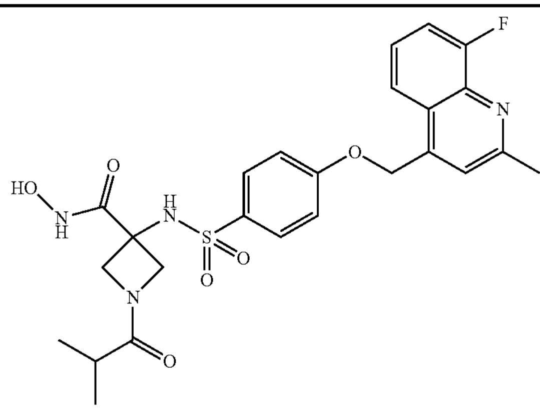 | 3-((4-((8-fluoro-2-methylquinolin-4-yl)methoxy)-N-methylphenyl)sulfonamido)-N-hydroxy-1-isobutyrylazetidine-3-carboxamide |
| 31 | 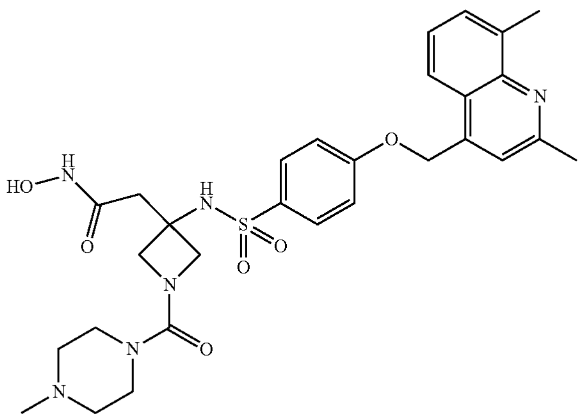 | 2-(3-((4-((2,8-dimethylquinolin-4-yl)methoxy)phenyl)sulfonamido)-1-(4-methylpiperazine-1-carbonyl)azetidin-3-yl)-N-hydroxyacetamide |

The present invention provides compounds exhibiting good TACE-inhibiting activity in a cellular setting (hPBMC). This TACE inhibiting activity is measured in a cellular setting and quantified via measurement of an IC50. The compounds provided herein have an IC50 of less than or equal to 1 µM. Advantageously, the compounds described herein have an $IC_{50}$ of less than or equal to 0.1 µM.

In addition, these compounds inhibit the TACE enzyme selectively as compared with MMP1. This TACE enzyme-inhibiting activity is measured in an enzymatic assay and quantified via the measurement of an $IC_{50}$ (inhibitory concentration necessary to obtain 50% inhibition of the TACE enzyme). The compounds provided herein have an $IC_{50}$ for TACE of less than or equal to 1 µM and more particularly less than or equal to 0.1 µM. Advantageously, the compounds described herein have an $IC_{50}$ for TACE less than or equal to 0.05 µM. Advantageously, these compounds are selective for TACE compared with MMP1: their inhibitory activity is at least 10 times greater for TACE than for MMP1 (i.e. the $IC_{50}$ value for TACE is at least 10 times smaller than that for other ADAMs and MMPs), and more advantageously at least 100 times greater.

TACE (TNFα-converting enzyme) catalyzes the formation of soluble TNFα from the precursor protein (transmembrane TNFα) bound to the membranes of certain cells. TNFα is a pro-inflammatory cytokine which is known to play a role in many pathological conditions with an inflammatory nature.

The present invention provides the use of at least one compound of formula (I) as defined above, for the treatment of pathological diseases, conditions, and disorders linked to TNFα release. A TACE enzyme inhibitor of formula (I) decreases TNFα production. As a result, a TACE enzyme inhibitor is useful for the treatment of pathological conditions, disease, or disorders associated with TNFα release.

The present invention provides compositions, in particular pharmaceutical and cosmetic compositions, comprising one or more compounds of formula (I) for use for the treatment of TNFα mediated diseases, condition, or disorders. The present invention provides a use of at least one compound of formula (I) having a TACE enzyme-inhibiting activity, for preparing a pharmaceutical or cosmetic composition.

In one aspect, the present invention provides one or more compounds of formula (I) as defined above, for use for the treatment of pathological diseases, conditions, or disorders which are improved by inhibiting the TACE enzyme. The one or more compounds may be in a pharmaceutical or cosmetic composition formulated for the treatment of TNFα mediated diseases, disorders, or conditions.

The present invention provides a method of therapeutic (human or animal) or cosmetic treatment comprising the administration or the application of a pharmaceutical or cosmetic composition comprising a compound of formula (I) as a TACE inhibitor and, consequently, as an inhibitor of soluble TNFα production. The method provided herein can be used to treat mammals, in particular humans, in particular mammals or humans in need of such treatment.

The present invention provides a method of using one or more compounds of formula (I) as defined above, for the treatment of pathological diseases, conditions, or disorders linked to or involving TNFα production.

In another aspect, the present invention also relates to a method of using a compound of formula (I) as defined above, for preparing a medicament intended for the treatment of pathological diseases, conditions, or disorders for which reducing TNFα production is desired.

The compounds disclosed herein are particularly suitable for the treatment and prevention of diseases, disorders, or conditions, such as but not limited to, the inflammatory diseases listed hereinafter, but are not limited thereto, such as septic shock, hemodynamic shock, malaria, inflammatory bowel diseases (IBDs) such as Crohn's disease and ulcerative colitis, inflammatory bone diseases, mycobacterial infections, meningitis, fibrotic diseases, cardiac diseases, atherosclerosis, obesity, ischemic attack, transplant rejection, cancer, diseases involving angiogenesis phenomena, autoimmune diseases, osteoarthritis, rheumatoid arthritis, ankylosing spondylitis, juvenile chronic arthritis, multiple sclerosis, HIV, non-insulin-dependent diabetes mellitus, allergic diseases, asthma, chronic obstructive pulmonary disease (COPD), inflammatory skin diseases, psoriasis, atopic dermatitis, psoriatic arthritis, acne, allergic contact dermatitis and actinic keratosis.

These compounds are also potential active ingredients for the treatment of neurological pathological conditions with an inflammatory nature, for which reducing TNFα production would be of great interest. These pathological conditions listed hereinafter in a nonlimiting manner are, for example, Alzheimer's disease, Parkinson's disease, parkinsonian disorders, amyotrophic lateral sclerosis, autoimmune diseases of the nervous system, autonomic diseases of the nervous system, dorsal pain, cerebral edema, cerebrovascular disorders, dementia, nervous system nerve fiber demyelinating autoimmune diseases, diabetic neuropathies, encephalitis, encephalomyelitis, epilepsy, chronic fatigue syndrome, giant cell arteritis, Guillain-Barré syndrome, headaches, multiple sclerosis, neuralgia, peripheral nervous system diseases, polyneuropathies, polyradiculoneuropathy, radiculopathy, respiratory paralysis, spinal cord diseases, Tourette's syndrome, central nervous system vasculitis, Huntington's disease and stroke.

The present invention provides a use of a compound of formula (I) as defined above, for preparing a medicament intended for the treatment of pathological conditions with an inflammatory nature, particularly in which TNFα is involved.

The present invention provides a use of a compound of formula (I) as defined above, for preparing a medicament for the treatment of inflammatory skin diseases, preferably psoriasis, atopic dermatitis, psoriatic arthritis, acne or actinic keratosis.

The present invention also provides a pharmaceutical composition for use in the treatment of the above mentioned diseases, disorders, or conditions, comprising at least one compound of formula (I), in a pharmaceutically acceptable carrier. The pharmaceutical carrier is compatible with the method of administration selected for this composition. The compound of formula (I) can also be in one of its enantiomeric forms or in the form of one of its pharmaceutically acceptable salts.

The following examples illustrate exemplary methods provided herein. These examples are not intended, nor are they to be construed, as limiting the scope of the invention. It will be clear that the methods can be practiced otherwise than as particularly described herein. Numerous modifications and variations are possible in view of the teachings herein and, therefore, are within the scope of the invention.

EXAMPLES

Representative compounds of formula (I) were synthesized and characterized.

Standard HPLC Preparation Method Used for Purification:

C18 column, using increasing amounts of acetonitrile in water/0.1% formic acid.

The compounds of formula (I) are prepared according to the reaction scheme (Scheme 1) presented below with standard conditions i) to vi).

Scheme 1
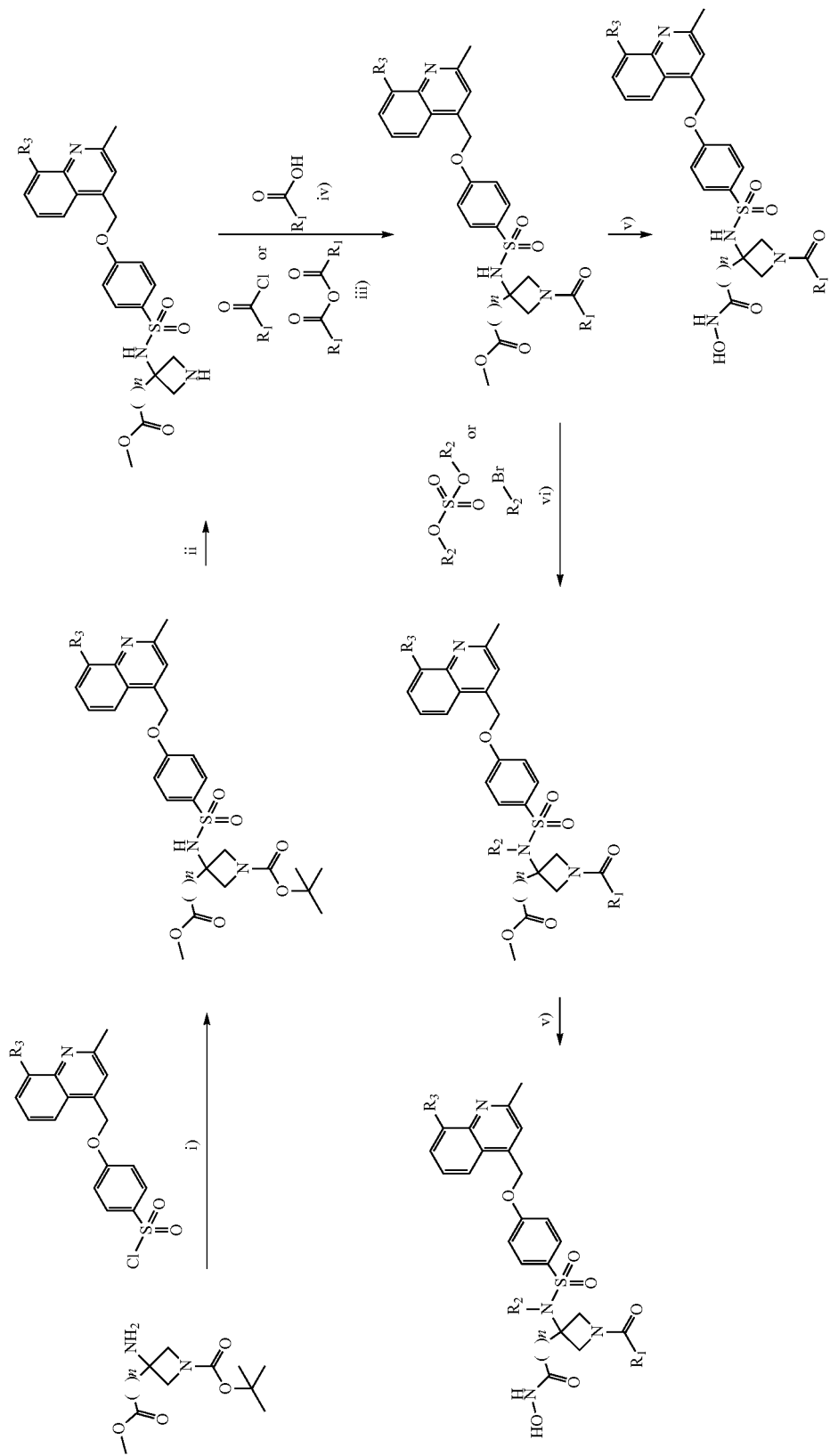
i) Dichloromethane, triethylamine
ii) Dichloromethane, trifluoroacetic acid
iii) Dichloromethane, triethylamine
iv) Dimethylformamide, 1-Ethyl-3-(3-dimethylaminopropyl)carbodiimide hydrochloride, 1-Oxy-pyridin-2-ol, N,N-diisopropylethylamine
v) Methanol, NH₂OHaq, DBU
vi) Dimethylformamide, Potassium carbonate A—Preparation of Intermediates Intermediate A Tert-butyl 3-(2-methoxy-2-oxo-ethyl)-3-[[4-[(2-methyl-4-quinolyl)methoxy]phenyl] sulfonylamino] azetidine-1-carboxylate

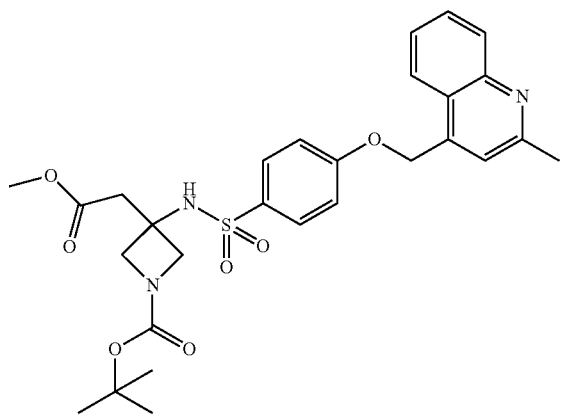

To a solution of tert-butyl 3-amino-3-(2-methoxy-2-oxo-ethyl)azetidine-1-carboxylate (9.5 g, 38.9 mmol, 1 eq) and triethylamine (13.13 ml, 97.2 mmol, 2.5 eq) in dichloromethane (200 mL) at 4° C. was slowly added 4-[(2-methyl-4-quinolyl)methoxy]benzenesulfonyl chloride (16.23 g, 46.7 mmol, 1.2 eq). The reaction mixture was stirred at room temperature overnight. Water was added to the reaction mixture and the organic layer was extracted, dried over magnesium sulfate, filtered and evaporated under reduced pressure. Dichloromethane was added to the residue. The precipitate was filtered and the filtrate was evaporated and purified by flash chromatography (dichloromethane/ethyl acetate 90/10 to 20/80). The solid filtered and the purified residue were gathered affording tert-butyl 3-(2-methoxy-2-oxo-ethyl)-3-[[4-[(2-methyl-4-quinolyl)methoxy]phenyl]sulfonylamino] azetidine-1-carboxylate as a white solid (12 g, 55.6%).

NMR (300 MHz, DMSO-$d_6$): δ (ppm) 1.33 (s, 9H), 2.66 (s, 3H), 2.90 (s, 2H), 3.37 (s, 3H), 3.76-3.84 (m, 4H), 5.71 (s, 2H), 7.32 (d, J=8.8 Hz, 2H), 7.56-7.62 (m, 2H), 7.71-7.77 (m, 3H), 7.97 (d, J=8.4 Hz, 1H), 8.10 (d, J=8.4 Hz, 1H), 8.40 (s, 1H).

MS(ES+) m/z 556 (MH+)

Intermediate B

Methyl 2-[3-[[4-[(2-methyl-4-quinolyl)methoxy] phenyl]sulfonylamino]azetidin-3-yl] acetate

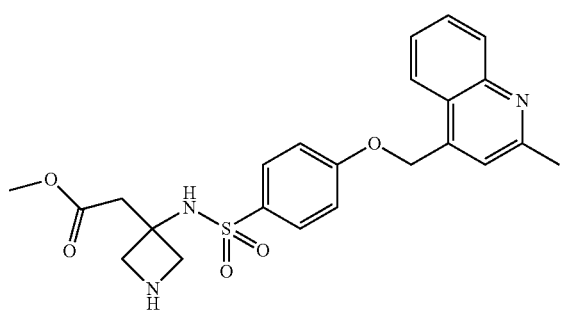

To a suspension of intermediate A (3 g, 5.4 mmol, 1 eq) in dichloromethane (30 mL) was added a 4N solution of HCl in dioxane (5.4 mL, 21.6 mmol, 4 eq). The reaction mixture was stirred at room temperature overnight. The solvent was removed under reduced pressure affording the dihydrochloride salt of methyl 2-[3-[[4-[(2-methyl-4-quinolyl)methoxy] phenyl]sulfonylamino]azetidin-3-yl]acetate as a white solid (2.85 g, 100%).

MS(ES+) m/z 456 (MH+)

Intermediate C

Methyl 2-[3-[[4-[(2,8-dimethyl-4-quinolyl)methoxy] phenyl]sulfonylamino] azetidin-3-yl]acetate

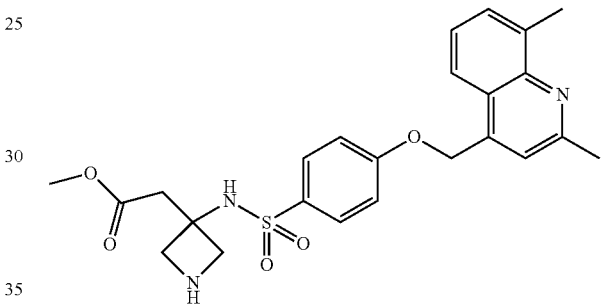

To a solution of tert-butyl 3-[[4-[(2,8-dimethyl-4-quinolyl)methoxy]phenyl] sulfonylamino]-3-(2-methoxy-2-oxo-ethyl)azetidine-1-carboxylate (191 mg, 0.34 mmol, 1 eq) in dichloromethane (2.2 ml) was added trifluoroacetic acid (0.51 ml, 6.7 mmol, 20 eq) and the mixture was stirred at room temperature overnight. The solvent was evaporated affording the di-trifluoroacetic acid salt of methyl 2-[3-[[4-[(2,8-dimethyl-4-quinolyl)methoxy]phenyl]sulfonylamino] azetidin-3-yl]acetate as a light brown oil (253 mg, 100% yield).

MS(ES+) m/z 470 (MH+)

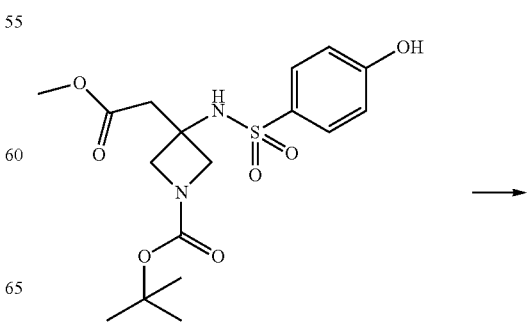

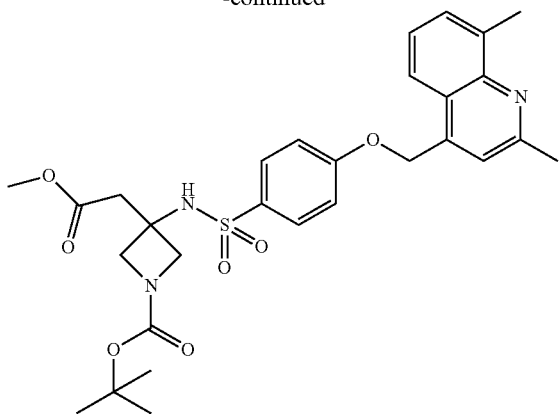

To a solution of tert-butyl 3-[(4-hydroxyphenyl)sulfonylamino]-3-(2-methoxy-2-oxo-ethyl)azetidine-1-carboxylate (247.3 mg, 0.62 mmol, 1 eq) and (2,8-dimethyl-4-quinolyl)methyl methanesulfonate (180.24 mg, 0.68 mmol, 1 eq) in anhydrous dimethylformamide (6 mL) was added potassium carbonate (256.1 mg, 1.8 mmol, 3 eq). The mixture was stirred at room temperature for 19 h then a saturated solution of sodium bicarbonate was added. The organic layer was extracted with AcOEt, dried over magnesium sulfate and concentrated under reduced pressure. The mixture was purified by flash chromatography (cyclohexane/AcOEt: 85:15 to 70:30) to give tert-butyl 3-[[4-[(2,8-dimethyl-4-quinolyl)methoxy]phenyl]sulfonylamino]-3-(2-methoxy-2-oxo-ethyl)azetidine-1-carboxylate as a colorless solid (194 mg, 55.1%).

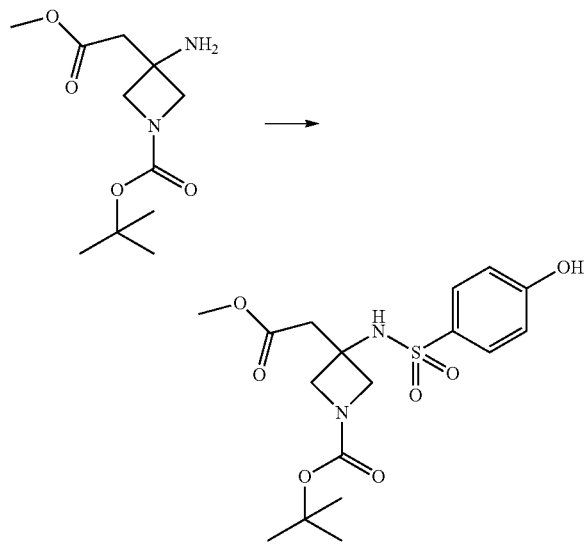

To a solution of 4-hydroxybenzenesulfonyl chloride (433.7 mg, 2.2 mmol, 1.1 eq) in chloroform (3.5 ml) was added N,O-bis(trimethylsilyl)acetamide (0.6 ml, 2.5 mmol, 1.2 eq). The mixture was stirred at room temperature for 3 h. Triethylamine (829 µl, 6.1 mmol, 3 eq) and tert-butyl 3-amino-3-(2-methoxy-2-oxo-ethyl)azetidine-1-carboxylate (509.2 µl, 2.05 mmol, 1 eq) in chloroform (3 mL) were added to the reaction mixture. The mixture was stirred overnight at room temperature and methanol (7 mL) was added. The reaction mixture was heated at 65° C. for 1 h.

Solvent were evaporated and the residue was purified by flash chromatography (cyclohexane/ethylacetate 60:40) to give tert-butyl 3-[(4-hydroxyphenyl)sulfonylamino]-3-(2-methoxy-2-oxo-ethyl)azetidine-1-carboxylate as a white solid (150 mg, 18.3% yield).

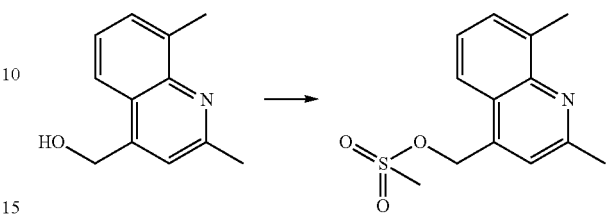

To a solution of (2,8-dimethyl-4-quinolyl)methanol (1 g, 5.34 mmol, 1 eq) in dichloromethane (20 mL) were added mesyl chloride (496.03 µl, 6.41 mmol, 1.2 eq) and triethylamine (2.16 ml, 16.02 mmol, 3 eq). The mixture was stirred at room temperature for 25 min then a saturated solution of sodium bicarbonate was added. The organic layer was dried over magnesium sulfate, filtered and the solvent was removed under reduced pressure to give (2,8-dimethyl-4-quinolyl)methyl methanesulfonate as a light brown solid (1.43 g, 100%). The solid was used in the next step without further purification.

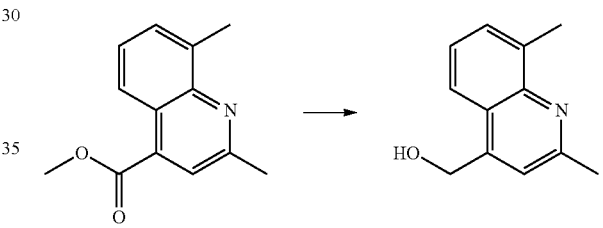

To a solution of methyl 2,8-dimethylquinoline-4-carboxylate (4 g, 18.58 mmol, 1 eq) in anhydrous dichloromethane (55 mL) was added dropwise 1.1M diisobutyl aluminum hydride in cyclohexane (35.48 ml, 39.02 mmol, 1.1 eq). The mixture was stirred at room temperature for 30 min. A saturated solution of ammonium chloride was added and the mixture was stirred at room temperature for 15 min. Aluminum salts were filtered, the organic layer was dried over magnesium sulfate, filtered and the solvent was removed under reduced pressure to give of (2,8-dimethyl-4-quinolyl)methanol as a yellow solid (2.58 g, 74.1%).

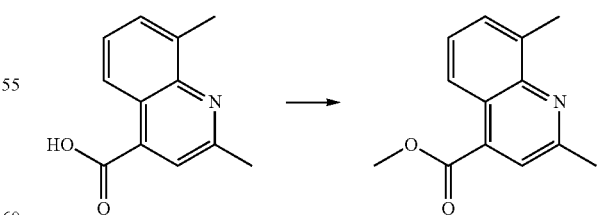

Thionyl chloride (10.61 ml, 146.29 mmol, 3.5 eq) was added dropwise to a cooled-down solution of 2,8-dimethylquinoline-4-carboxylic acid (8.49 g, 42.19 mmol, 1 eq) in methanol (200 mL) at 0° C. The mixture was heated at 70° C. overnight then concentrated to dryness. The residue was partitioned between a saturated solution of sodium bicarbonate and dichloromethane. The organic layer was dried over magnesium sulfate, filtered and the solvent was removed under reduced pressure to give methyl 2,8-dimethylquinoline-4-carboxylate as a brown solid (7.36 g, 81%). The solid was used in the next step without further purification.

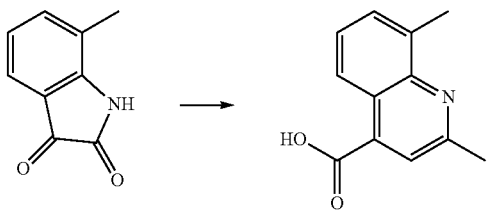

To a solution of potassium hydroxide (11.8 g, 211 mmol, 5 eq) in water (80 mL) was added 7-methylindoline-2,3-dione (6.8 g, 42.2 mmol, 1 eq) in ethanol (100 mL). The mixture was stirred at 76° C. then acetone (50 mL) was added. The mixture was heated to 76° C. for 3 days. Acetone and ethanol were removed under reduced pressure. Impurities were removed by extraction with dichloromethane. Aqueous layer was lyophilized to give 2,8-dimethylquinoline-4-carboxylic acid as a brown solid (7.05 g, 83%).

Intermediate D

O1-tert-butyl O3-methyl 3-[[4-[(2-methyl-4-quinolyl)methoxy]phenyl]sulfonylamino] azetidine-1,3-dicarboxylate

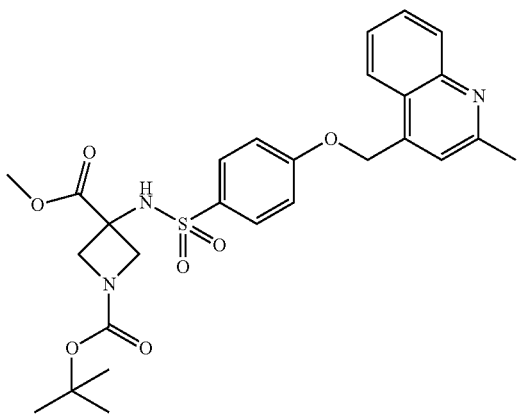

To a solution of 3-amino-1-tert-butoxycarbonyl-azetidine-3-carboxylic acid (1.4 g, 6 mmol, 1 eq) in dichloromethane (14 mL) were added triethylamine (2.05 mL, 15.2 mmol, 2.5 eq) and 4-[(2-methyl-4-quinolyl)methoxy]benzenesulfonyl chloride hydrochloride (2.8 g, 7.3 mmol, 1.2 eq). The mixture was stirred at room temperature for 48 h. Water (20 mL) was added to the reaction mixture and the organic layer was extracted with dichloromethane, dried over magnesium sulfate, filtered and evaporated. The residue was purified by flash chromatography (dichloromethane/ethyl acetate 100:0 to 50:50) to give O1-tert-butyl O3-methyl 3-[[4-[(2-methyl-4-quinolyl)methoxy]phenyl]sulfonylamino]azetidine-1,3-dicarboxylate as a white solid (1.80 g, 54.7%).

$^1$H NMR (300 MHz, DMSO-$d_6$): δ 1.34 (s, 9H), 2.66 (s, 3H), 3.39 (s, 3H), 3.84 (d, J=9.0 Hz, 2H), 4.10 (d, J=9.0 Hz, 2H), 5.73 (s, 2H), 7.34 (d, J=8.8 Hz, 2H), 7.55 (s, 1H), 7.60 (t, J=8.3 Hz, 1H), 7.69 (d, J=8.8 Hz, 2H), 7.75 (t, J=8.3 Hz, 1H), 7.97 (d, J=8.3 Hz, 1H), 8.10 (d, J=8.3 Hz, 1H), 8.87 (s, 1H).

MS(ES+) m/z 542 (MH+)

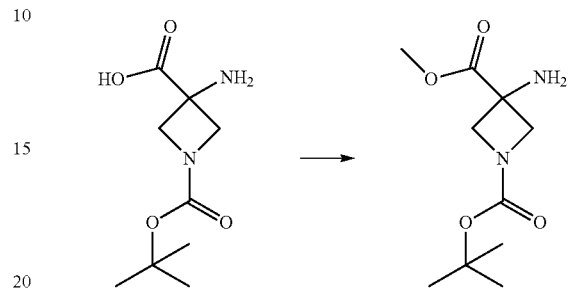

To a suspension of 3-amino-1-tert-butoxycarbonyl-azetidine-3-carboxylic acid (1.4 g, 6.5 mmol, 1 eq) in dichloromethane (21 mL) and methanol (14 mL) was added Trimethylsilyl)diazomethane (2M in hexane, 7.1 mL, 14.2 mmol, 2.2 eq). The reaction mixture was stirred at room temperature for 17 h. 3 drops of acetic acid was added. Solvent were removed and dichloromethane was added to the residue. A saturated solution of NaHCO$_3$ was added. Aqueous layer was washed with dichloromethane. The organic layer was washed with brine, dried over magnesium sulfate, filtered and evaporated to give O1-tert-butyl O3-methyl 3-aminoazetidine-1,3-dicarboxylate as a yellow oil (1.4 g, 93.9%). The product was used in the next step without further purification.

Intermediate E

Methyl 3-[[4-[(2-methyl-4-quinolyl)methoxy]phenyl]sulfonylamino]azetidine-3-carboxylate

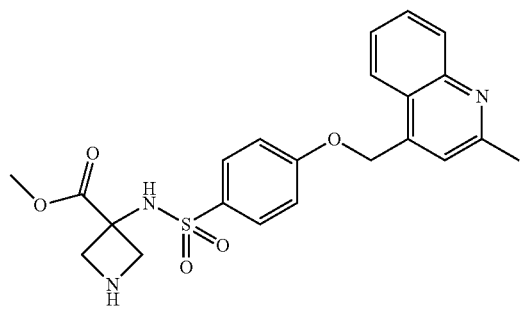

To a suspension of Intermediate D (1.8 g, 3.3 mmol, 1 eq) in dichloromethane (30 ml) was added 4N HCl in dioxane (8.3 ml, 33.2 mmol, 10 eq). The mixture was stirred at room temperature overnight then was concentrated to dryness to give the dihydrochloride salt of methyl 3-[[4-[(2-methyl-4-quinolyl)methoxy]phenyl]sulfonylamino]azetidine-3-carboxylate as a white solid (1.7 g, 99.4%).

MS(ES+) m/z 442 (MH+)

Intermediate F

Methyl 3-[[4-[(2,8-dimethyl-4-quinolyl)methoxy]phenyl]sulfonylamino]azetidine-3-carboxylate

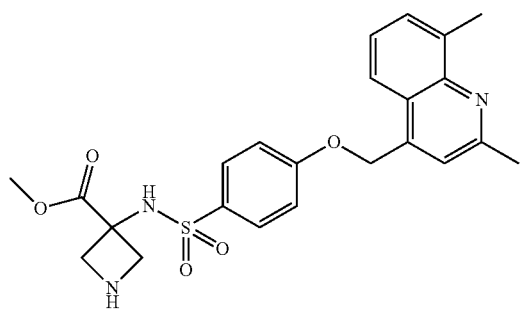

Methyl 3-[[4-[(2,8-dimethyl-4-quinolyl)methoxy]phenyl]sulfonylamino]azetidine-3-carboxylate was obtained using the same procedure as for Intermediate E starting from O1-tert-butyl O3-methyl 3-[[4-[(2,8-dimethyl-4-quinolyl)methoxy]phenyl] sulfonylamino] azetidine-1,3-dicarboxylate.

MS(ES+) m/z 456 (MH+)

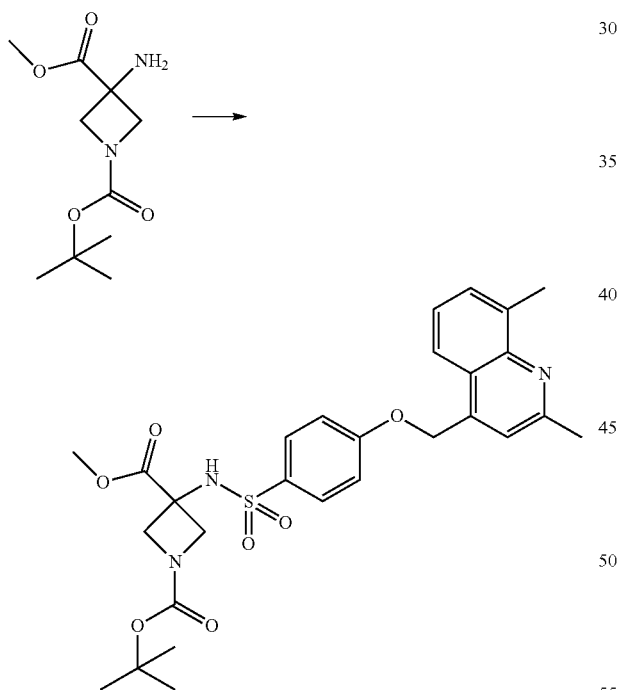

To O1-tert-butyl O3-methyl 3-aminoazetidine-1,3-dicarboxylate (433 mg, 1.88 mmol, 1 eq) in dichloromethane (4.3 mL) were added triethylamine (312.7 µl, 2.32 mmol, 2.5 eq) and the hydrochloride salt of 4-[(2,8-dimethyl-4-quinolyl) methoxy]benzenesulfonyl chloride (369 mg, 0.93 mmol, 2 eq). The mixture was stirred at room temperature overnight. A NaHCO₃ saturated solution was added to the reaction, the organic layer was extracted with AcOEt, dried over magnesium sulfate, filtered and evaporated. The residue was purified by flash chromatography (cyclohexane/AcOEt 85:15 then 60:40) to give O1-tert-butyl O3-methyl 3-[[4-[(2,8-dimethyl-4-quinolyl)methoxy]phenyl]sulfonylamino]azetidine-1,3-dicarboxylate as a colorless solid (223 mg, 43.3%).

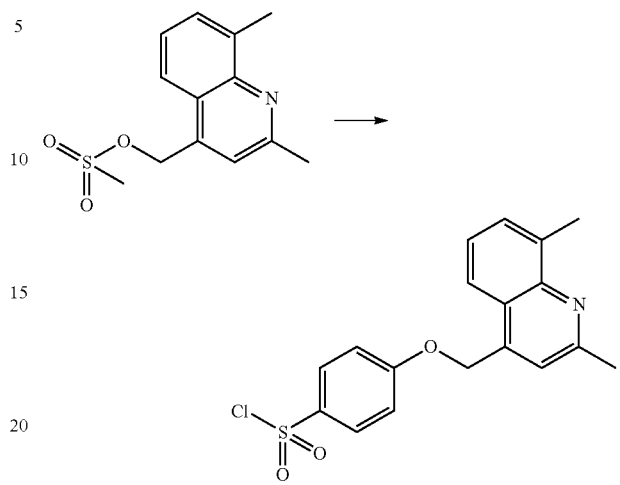

To a solution of sodium 4 hydroxybenzene sulfinate (261 mg, 0.68 mmol) and (2,8-dimethyl-4-quinolyl)methyl methanesulfonate (754.21 mg, 2.84 mmol) in acetonitrile (26 ml) was added potassium carbonate (535.73 mg, 3.88 mmol). The mixture was heated at 70° C. for 3 days. The precipitate was filtered to give sodium; 4-[(2,8-dimethyl-4-quinolyl) methoxy]benzenesulfonate as an orange solid (910 mg, 96%). The compound was used in the next step without further purification.

Oxalyl chloride (4.7 mL, 54.7 mmol, 10 eq) was added dropwise to a cooled down suspension of sodium 4-[(2,8-dimethyl-4-quinolyl)methoxy]benzenesulfonate (2 g, 5.47 mmol, 1 eq) in N,N dimethylformamide (0.3 mL) and dichloromethane (10 mL) at 0° C. The mixture was stirred at room temperature for 1 hr. The resulting suspension was filtered off. The cake was washed with dichloromethane and dried under reduced pressure to give the hydrochloride salt of 4-[(2,8-dimethyl-4-quinolyl)methoxy]benzenesulfonyl chloride as white solid (1.85 g, 84.9%).

B—Preparation of Compounds of Formula (I)

Example 1

2-(1-acetyl-3-((4-((2-methylquinolin-4-yl)methoxy)phenyl)sulfonamido)azetidin-3-yl)-N-hydroxyacetamide

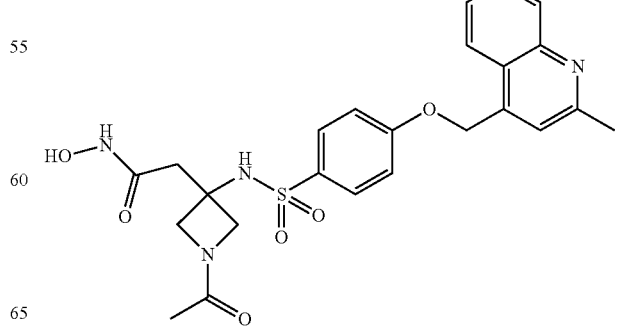

An aqueous solution of hydroxylamine (145 μl; 2.37 mmol; 20.00 eq.) was added dropwise to a solution of {1-acetyl-3-[4-(2-methyl-quinolin-4-ylmethoxy)-benzene-sulfonylamino]-azetidin-3-yl}-acetic acid methyl ester (59.00 mg; 0.12 mmol; 1.00 eq.) in tetrahydrofuran (0.59 ml) and methanol (0.59 ml), immediately followed by potassium cyanide (1.54 mg; 0.02 mmol; 0.20 eq.). The reaction mixture was stirred for 17 hours at room temperature. The reaction mixture was concentrated to dryness. Water was added. A 1N hydrochloric acid solution was added until pH reached 5-6. The suspension was washed with ethylacetate. The suspension was filtered and the solid washed with ethyl acetate. 2-{1-Acetyl-3-[4-(2-methyl-quinolin-4-ylmethoxy)-benzenesulfonylamino]-azetidin-3-yl}-N-hydroxy-acetamide (30.00 mg; 48.92%) was isolated as a white solid.

¹H NMR (400 MHz, DMSO-d₆): δ (ppm) 1.63 (s, 3H), 2.55 (s, 2H), 2.67 (s, 3H), 3.74-3.82 (q, J=10.0 Hz, 2H), 4.05 (d, J=9.0 Hz, 1H), 4.17 (d, J=9.0 Hz, 1H), 5.72 (s, 2H), 7.33 (d, J=8.8 Hz, 2H), 7.56 (s, 1H), 7.60 (t, J=7.3 Hz, 1H), 7.76 (t, J=7.1 Hz, 1H), 7.81 (d, J=8.8 Hz, 2H), 7.99 (d, J=8.3 Hz, 1H), 8.10 (d, J=8.2 Hz, 1H), 8.80 (s, 1H), 10.44 (s, 1H)

MS(ES+) m/z 499 (MH+)

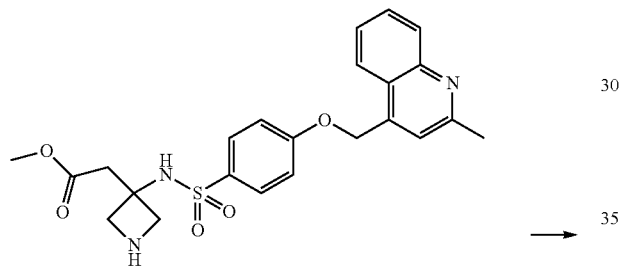

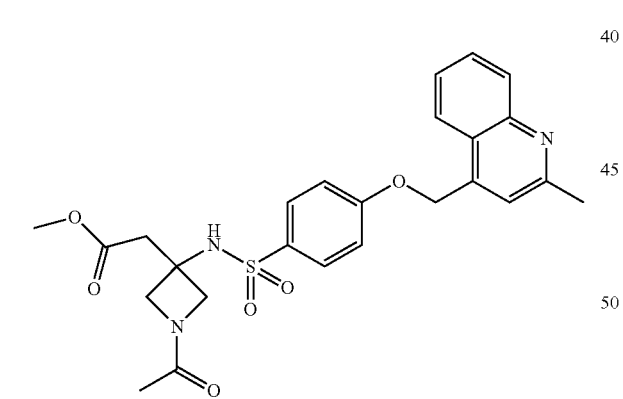

Triethylamine (30 μl; 0.21 mmol; 1.20 eq.) was added dropwise to a cooled down solution of Intermediate B (81.00 mg; 0.18 mmol; 1.00 eq.) in tetrahydrofuran (1.00 ml) at 0° C., followed by acetic anhydride (17 μl; 0.18 mmol; 1.00 eq.). The reaction mixture was stirred at 0° C. for 45 minutes. Water was added to the mixture, which was then extracted with ethyl acetate. The organic layers were combined, washed with brine, dried over magnesium sulfate, filtered and concentrated. {1-Acetyl-3-[4-(2-methyl-quinolin-4-ylmethoxy)-benzenesulfonylamino]-azetidin-3-yl}-acetic acid methyl ester, (61.00 mg; 68.95%) was isolated as a white solid.

Example 2

Tert-butyl 3-(2-(hydroxyamino)-2-oxoethyl)-3-((4-((2-methylquinolin-4-yl)methoxy)phenyl)sulfonamido)azetidine-1-carboxylate

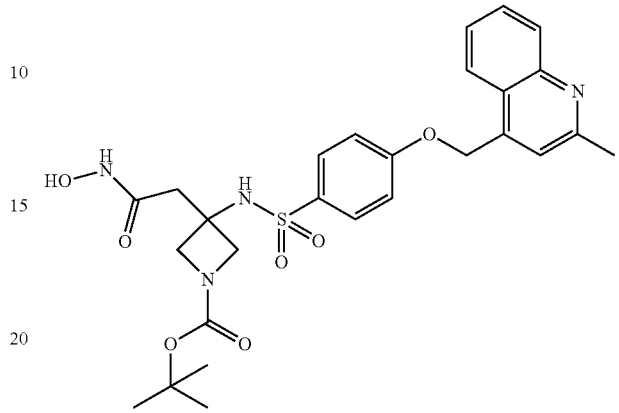

Example 2 was synthesized using the same protocol as Example 1 starting from Intermediate A.

¹H NMR (400 MHz, DMSO-d₆) δ 1.32 (s, 9H), 2.68 (s, 3H), 3.82 (br m, 6H), 5.74 (s, 2H), 7.24-7.41 (m, 2H), 7.51-7.67 (m, 2H), 7.69-7.87 (m, 3H), 7.99 (d, J=8.2 Hz, 1H), 8.97 (br s, 1H).

MS(ES+) m/z 557 (MH+)

Example 3

2-(1-acetyl-3-((N-methyl-4-((2-methylquinolin-4-yl)methoxy)phenyl)sulfonamido)azetidin-3-yl)-N-hydroxyacetamide

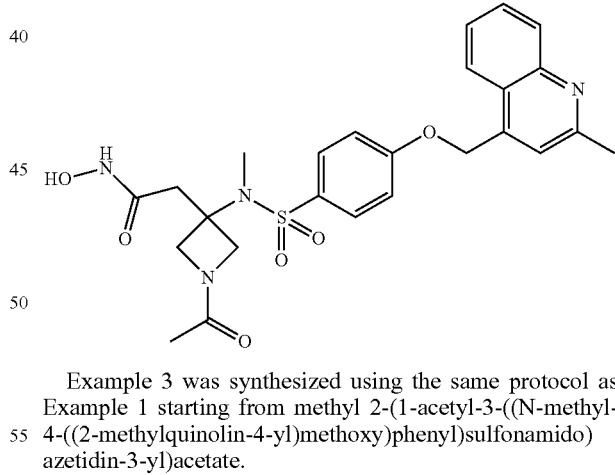

Example 3 was synthesized using the same protocol as Example 1 starting from methyl 2-(1-acetyl-3-((N-methyl-4-((2-methylquinolin-4-yl)methoxy)phenyl)sulfonamido)azetidin-3-yl)acetate.

¹H NMR (400 MHz, DMSO-d₆) δ 1.74 (s, 3H), 2.69 (2 overlapping s, 6H), 4.02 (s, 2H), 4.11-4.52 (m, 2H), 5.78 (s, 2H), 7.37 (d, J=9.0 Hz, 2H), 7.66 (s, 2H), 7.69-7.96 (m, 3H), 8.03 (d, J=8.4 Hz, 1H), 8.17 (d, J=8.4 Hz, 1H), 8.88 (s, 1H), 10.65 (s, 1H).

MS(ES+) m/z 513 (MH+)

Methyl 2-(1-acetyl-3-((N-methyl-4-((2-methylquinolin-4-yl)methoxy)phenyl)sulfonamido) azetidin-3-yl)acetate was synthesized using the protocol described in Example 1 (acetyl formation) and in Intermediate B (Boc deprotection) starting from tert-butyl 3-(2-methoxy-2-oxoethyl)-3-((N- methyl-4-((2-methylquinolin-4-yl)methoxy)phenyl)sulfonamido)azetidine-1-carboxylate.

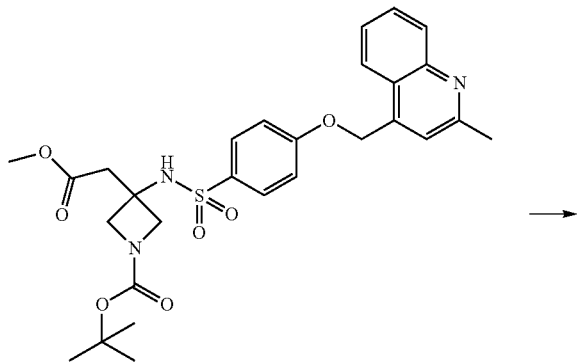

Potassium carbonate (87.30 mg; 0.63 mmol; 1.30 eq.) was added to a solution of Intermediate A (270.00 mg; 0.49 mmol; 1.00 eq.) in dimethylformamide (5 ml). Methyl sulfate was subsequently added (67 mg; 0.53 mmol; 1.10 eq.). The reaction mixture was stirred at room temperature for 16 hours. The mixture was diluted in ethyl acetate (50 mL), washed with water (5×5 mL), dried over Magnesium sulfate and concentrated. Tert-butyl 3-(2-methoxy-2-oxo-ethyl)-3-((N-methyl-4-((2-methylquinolin-4-yl)methoxy)phenyl)sulfonamido)azetidine-1-carboxylate (270.00 mg; 97.54%) was isolated as a colorless gum.

Example 4a

N-hydroxy-2-(1-(3-methylbutanoyl)-3-((4-((2-methylquinolin-4-yl)methoxy)phenyl) sulfonamido)azetidin-3-yl)acetamide

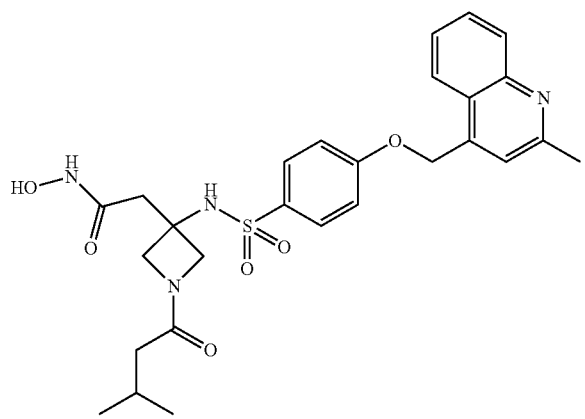

Example 4a was synthesized using the same protocol as Example 1 starting from {1-(3-Methyl-butyryl)-3-[4-(2-methyl-quinolin-4-ylmethoxy)-benzenesulfonylamino]-azetidin-3-yl}-acetic acid methyl ester. The final compound was purified by gel chromatography using dichloromethane/methanol (90/10) as eluent.

$^1$H NMR (400 MHz, DMSO-$d_6$): δ (ppm) 0.77-0.79 (d, J=6.3 Hz, 3H), 0.81-0.83 (d, J=6.4 Hz, 3H), 1.76 (d, 1H), 1.77-1.84 (m, 1H), 2.56 (s, 2H), 2.67 (s, 3H), 3.76-3.83 (q, J=10.2 Hz, 2H), 4.04-4.06 (d, J=9.0 Hz, 1H), 4.15-4.17 (d, J=9.1 Hz, 1H), 5.71 (s, 2H), 7.31-7.33 (d, J=9.0 Hz, 2H), 7.57 (s, 1H), 7.58-7.62 (td, J=7.0-1.2 Hz, 1H), 7.74-7.77 (td, 1H), 7.78-7.82 (dd, 2H), 7.97-7.99 (d, J=8.4 Hz, 1H), 8.09-8.11 (d, J=8.3 Hz, 1H), 8.25 (, 1H), 8.8 (s, 1H)

MS(ES+) m/z 541 (MH+)

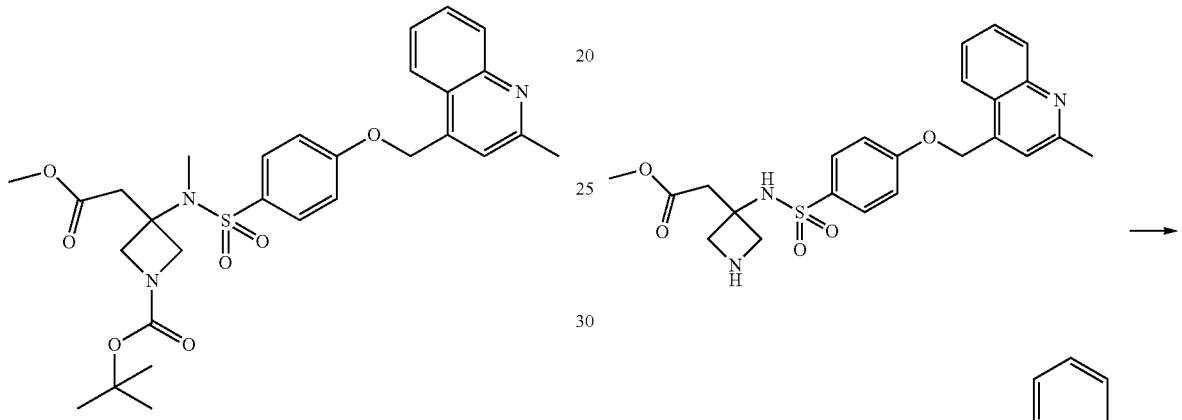

Triethylamine (219 μl; 1.58 mmol; 3.00 eq.) was added dropwise to a cooled down suspension of Intermediate B (300.00 mg; 0.53 mmol; 1.00 eq.) in tetrahydrofuran (6.00 ml) at 0° C., followed by isovaleryl chloride (64.22 μl; 0.53 mmol; 1.00 eq.). The reaction mixture was stirred at 0° C. for 2 hours. Water was added to the mixture. The mixture was extracted with ethyl acetate. The organic layers were combined, washed with brine, dried over magnesium sulfate and concentrated. {1-(3-Methyl-butyryl)-3-[4-(2-methyl-quinolin-4-ylmethoxy)-benzenesulfonylamino]-azetidin-3-yl}-acetic acid methyl ester (234.00 mg; 82.32%) was isolated as a white solid.

The examples shown in the following table were all synthesized using a similar protocol as Example 4a starting from the corresponding acyl chlorides. When necessary, the final compounds were purified either by gel chromatography using dichloromethane/methanol (90/10) as eluent, or by the standard prep HPLC method described above.

| Example number/ Name | Structure | NMR | MS(ES+) m/z |
|---|---|---|---|
| Example 4b: N-hydroxy-2-(1-isobutyryl-3-((4-((2-methylquinolin-4-yl)methoxy)phenyl)sulfonamido)azetidin-3-yl)acetamide | 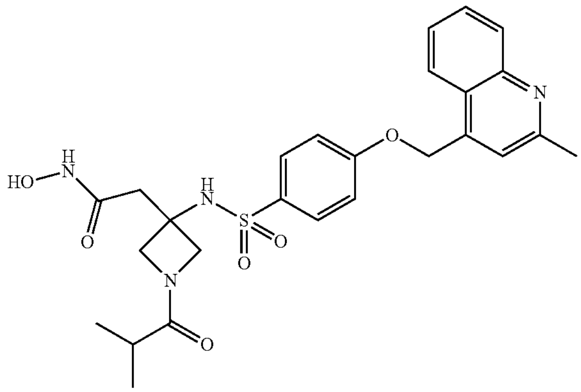 [SMILES: Cc1cc(COc2ccc(S(=O)(=O)NC3(CC(=O)NO)CN(C(=O)C(C)C)C3)cc2)c2ccccc2n1] | ¹H NMR (400 MHz, DMSO-d₆): δ (ppm) 0.83 (d, J = 1.7 Hz 3H), 0.88 (d, J = 1.7 Hz, 3H), 2.26 (m, 1H), 2.56 (s, 2H), 2.94 (s, 3H), 3.75 (m, 2H), 4.09 (d, J = 2.0 Hz, 1H), 4.22 (d, J = 2.0 Hz, 1H), 5.94 (s, 2H), 7.39 (d, J = 2.2 Hz, 2H), 7.84 (d, J = 2.2 Hz, 2H), 7.98 (m, 1H), 8.08 (m, 1H), 8.38 (m, 3H), 10.05 (bs, 1H), 10.50 (s, 1H) | 527 |
| Example 4c: 2-(1-(cyclopropanecarbonyl)-3-((4-((2-methylquinolin-4-yl)methoxy)phenyl)sulfonamido)azetidin-3-yl)-N-hydroxyacetamide | 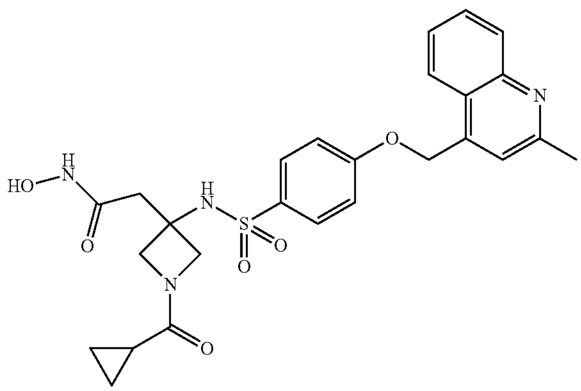 [SMILES: Cc1cc(COc2ccc(S(=O)(=O)NC3(CC(=O)NO)CN(C(=O)C4CC4)C3)cc2)c2ccccc2n1] | ¹H NMR (400 MHz, DMSO-d₆): δ (ppm) 0.62 (m, 4H), 1.37 (m, 1H), 2.57 (s, 2H), 2.66 (s, 3H), 3.79 (m, 2H), 4.17 (m, 1H), 4.31 (m, 1H), 5.71 (s, 2H), 7.32 (d, J = 2.1 Hz, 2H), 7.58 (m, 2H), 7.76 (m, 3H), 7.97 (d, J = 2.1 Hz, 1H), 8.09 (d, J = 2.1 Hz, 1H), 8.24 (bs, 1H), 8.82 (bs, 1H), 10.47 (s, 1H) | 525 |
| Example 4d: N-hydroxy-2-(3-((4-((2-methylquinolin-4-yl)methoxy)phenyl)sulfonamido)-1-pivaloylazetidin-3-yl)acetamide | 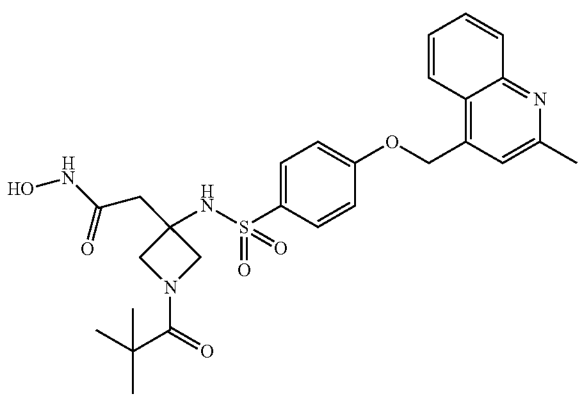 [SMILES: Cc1cc(COc2ccc(S(=O)(=O)NC3(CC(=O)NO)CN(C(=O)C(C)(C)C)C3)cc2)c2ccccc2n1] | ¹H NMR (400 MHz, DMSO-d₆): δ (ppm) 0.95 (s, 9H), 2.55 (s, 2H), 2.67 (s, 3H), 3.79 (s, 2H), 4.25 (s, 1H), 4.40 (s, 1H), 5.71 (s, 2H), 7.31-7.34 (dd, J = 9.0 Hz, 2H), 7.57 (s, 1H), 7.58-7.61 (td, J = 7.0-1.2 Hz, 1H), 7.74-7.78 (td, 1H), 7.81-7.83 (dd, 2H), 7.97-7.99 (d, J = 8.4 Hz, 1H), 8.09-8.11 (dd, J = 8.3-0.7 Hz, 1H), 8.25 (s, 1H), 8.8 (s, 1H), 10.45 (s, 1H). | 541 |
| Example 4e: 2-(1-butyryl-3-((4-(2-methylquinolin-4-yl)methoxy)phenyl)sulfonamido)azetidin-3-yl)-N-hydroxyacetamide | 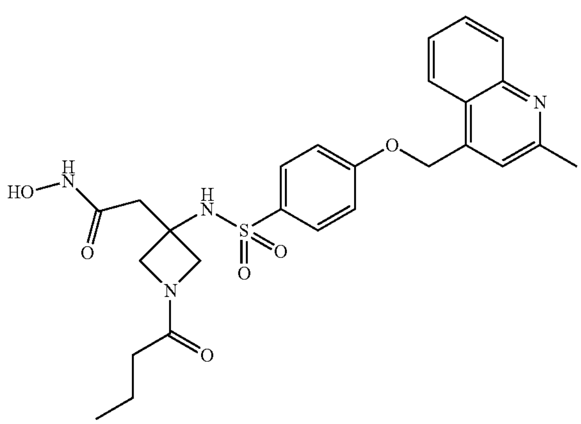 [SMILES: CCCC(=O)N1CC(CC(=O)NO)(NS(=O)(=O)c2ccc(OCc3cc(C)nc4ccccc34)cc2)C1] | ¹H NMR (400 MHz, CD₃OD): δ (ppm) 0.92 (m, 3H), 1.56 (m, 2H), 2.06 (m, 2H), 2.75 (d, J = 1.6 Hz, 2H), 3.02 (s, 3H), 3.98 (m, 2H), 4.29 (m, 2H), 5.99 (s, 2H), 7.37 (d, J = 2.3 Hz, 2H), 7.92 (d, J = 2.3 Hz, 2H), 7.97 (m, 1H), 8.16 (m, 3H), 8.45 (m, 1H) | 527 |

-continued

| Example number/ Name | Structure | NMR | MS(ES+) m/z |
|---|---|---|---|
| Example 4f: N-hydroxy-2-(1-(2-methoxyacetyl)-3-((4-((2-methylquinolin-4-yl)methoxy)phenyl)sulfonamido)azetidin-3-yl)acetamide | 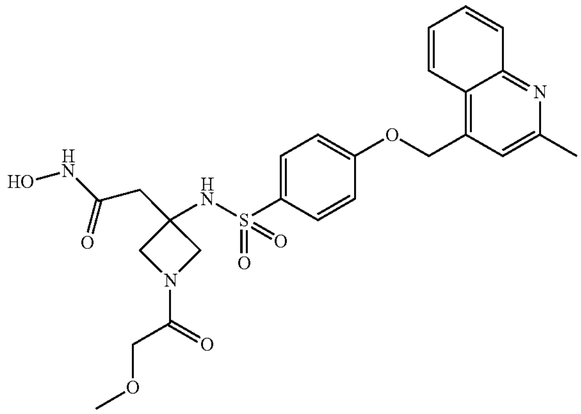 | $^1$H NMR (400 MHz, CD$_3$OD): δ (ppm) 2.75 (d, J = 1.0 Hz, 2H), 2.99 (s, 3H), 3.32 (s, 3H);, 3.91 (s, 2H), 4.04 (s, 2H), 4.38 (s, 2H), 5.98 (s, 2H), 7.36 (d, J = 2.1 Hz, 2H), 7.91 (d, J = 2.1 Hz, 2H), 7.96 (m, 1H), 8.14 (m, 3H), 8.43 (d, J = 2.1 Hz, 1H) | 529 |
| Example 4g: N-hydroxy-2-(3-((4-(2-methylquinolin-4-yl)methoxy)phenyl)sulfonamido)-1-(tetrahydro-2H-pyran-4-carbonyl)azetidin-3-yl)acetamide | 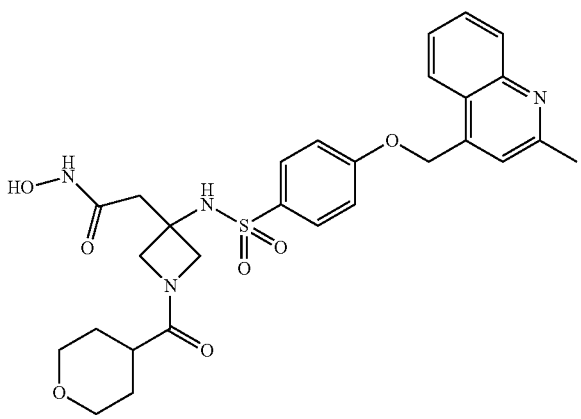 | $^1$H NMR (400 MHz, DMSO-d$_6$): δ (ppm) 1.35 (m, 4H), 2.30 (m, 1H), 2.58 (s, 2H), 2.84 (s, 3H), 3.26 (m, 2H), 3.78 (m, 4H), 4.14 (d, J = 2.3 Hz, 1H), 4.27 (d, J = 2.3 Hz, 1H), 5.88 (s, 2H), 7.37 (d, J = 2.2 Hz, 2H), 7.86 (m, 4H), 7.97 (m, 1H), 7.99 (m, 1H), 8.31 (m, 1H), 10.48 (s, 1H) | 569 |
| Example 4h: 2-(1-(cyclopentanecarbonyl)-3-((4-((2-methylquinolin-4-yl)methoxy)phenyl)sulfonamido)azetidin-3-yl)-N-hydroxyacetamide | 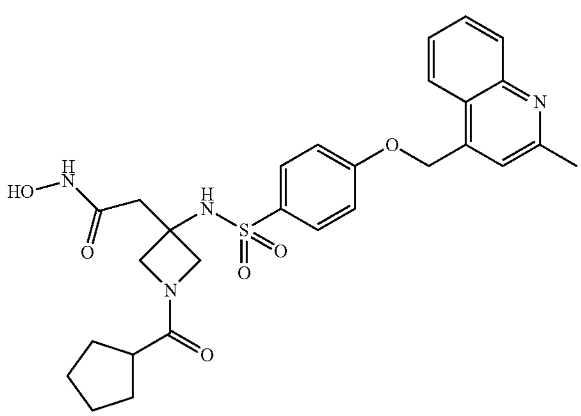 [SMILES: Cc1cc(COc2ccc(S(=O)(=O)NC3(CC(=O)NO)CN(C(=O)C4CCCC4)C3)cc2)c2ccccc2n1] | $^1$H NMR (300 MHz, CDCl$_3$): δ(ppm) 1.72 (brs, 8 H), 2.43-2.53 (m, 1 H), 2.78 (s, 3 H), 3.02 (s, 2 H), 3.62 (s, 3 H), 3.86 (d, J = 10.6 Hz, 1 H), 4.01 (d, J = 9.2 Hz, 1 H), 4.11 (d, J = 10.6 Hz, 1 H), 4.37 (d, J = 9.2 Hz, 1 H), 5.59 (s, 2 H), 5.72 (s, 1 H), 7.14 (d, J = 8.9 Hz, 2 H), 7.44 (s, 1 H), 7.55-7.60 (m, 1 H), 7.75 (ddd, J = 8.5, 6.9, 1.4 Hz, 1 H), 7.85 (d, J = 8.8 Hz, 2 H), 7.92 (d, J = 8.4 Hz, 1 H), 8.12 (d, J = 8.5 Hz, 1 H) | 553 |

| Example number/ Name | Structure | NMR | MS(ES+) m/z |
|---|---|---|---|
| Example 4i: 2-(1-(2-ethylbutanoyl)-3-((4-((2-methylquinolin-4-yl)methoxy)phenyl)sulfonamido)azetidin-3-yl)-N-hydroxyacetamide | 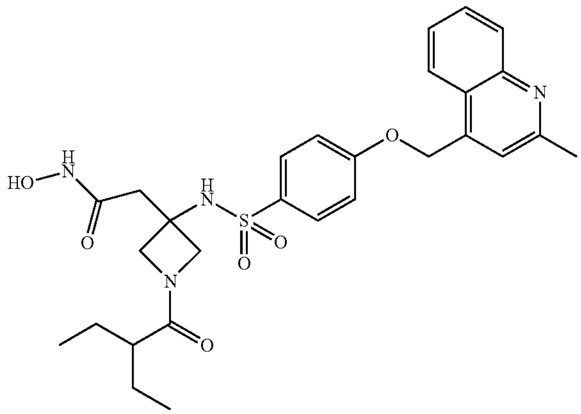 [SMILES: CCC(CC)C(=O)N1CC(CC(=O)NO)(NS(=O)(=O)c2ccc(OCc3cc(C)nc4ccccc34)cc2)C1] | $^1$H NMR (300 MHz, DMSO-d$_6$): δ (ppm) 0.67-0.76 (m, 6 H), 1.24-1.40 (m, 4 H), 1.89-1.96 (m, 1 H), 2.66 (s, 3 H), 2.91 (s, 2 H), 3.39 (s, 3H), 3.76-3.87 (m, 2 H), 4.05-4.15 (m, 2 H), 5.71 (s, 2 H), 7.32 (d, J = 8.8 Hz, 2 H), 7.56 (s, 1 H), 7.57-7.62 (m, 1 H), 7.73-7.78 (m, 3 H), 7.98 (d, J = 8.4 Hz, 1 H), 8.10 (d, J = 8.3 Hz, 1 H), 8.49 (s, 1 H) | 555 |
| Example 4j: 2-(1-(cyclohexanecarbonyl)-3-((4-((2-methylquinolin-4-yl)methoxy)phenyl)sulfonamido)azetidin-3-yl)-N-hydroxyacetamide | 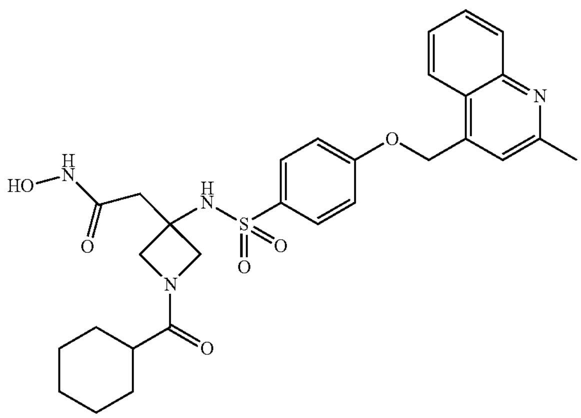 [SMILES: Cc1cc(COc2ccc(S(=O)(=O)NC3(CC(=O)NO)CN(C(=O)C4CCCCC4)C3)cc2)c2ccccc2n1] | $^1$H NMR (300 MHz, DMSO-d$_6$): δ(ppm) 1.14-1.22 (m, 6 H), 1.54-1.63 (m, 4 H), 2.03-2.07 (m, 1 H), 2.67 (s, 3 H), 2.92 (s, 2 H), 3.38 (s, 3 H), 3.71-3.82 (m, 2 H), 4.12 (s, 2 H), 5.71 (s, 2 H), 7.32 (d, J = 8.8 Hz, 2 H), 7.56-7.61 (m, 2 H), 7.74-7.78 (m, 3 H), 7.98 (d, J = 8.4 Hz, 1 H), 8.11 (d, J = 8.3 Hz, 1 H), 8.45 (s, 1 H) | 567 |

Example 5a

Ethyl 3-(2-(hydroxyamino)-2-oxoethyl)-3-((4-((2-methylquinolin-4-yl)methoxy) phenyl)sulfonamido) azetidine-1-carboxylate Example 5a was synthesized using the same protocol as Example 1 starting from ethyl 3-(2-methoxy-2-oxoethyl)-3-((4-((2-methylquinolin-4-yl)methoxy)phenyl)sulfonamido) azetidine-1-carboxylate. The final compound was purified by prep HPLC using the standard method.

1H NMR (400 MHz, DMSO-d6) δ: 1.10 (t, J=7.1 Hz, 3H), 2.56 (s, 2H), 2.68 (s, 3H), 3.91 (dd, J=20.8, 13.8 Hz, 6H), 5.72 (s, 2H), 7.27-7.37 (m, 2H), 7.51-7.66 (m, 2H), 7.73-7.85 (m, 3H), 7.99 (d, J=8.3 Hz, 1H), 8.11 (d, J=8.3 Hz, 1H), 8.22 (s, 1H), 8.81 (d, J=1.8 Hz, 1H), 10.46 (s, 1H)

MS(ES+) m/z 529 (MH+)

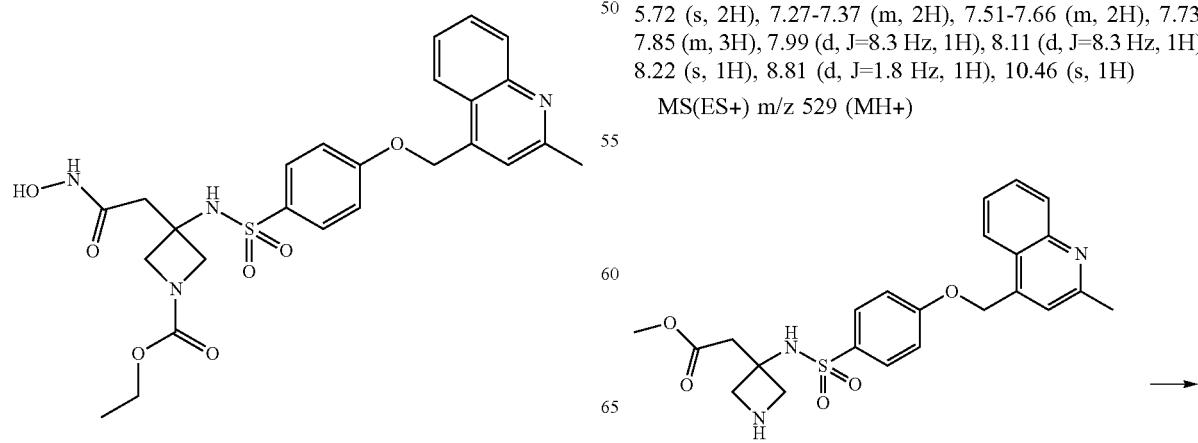

-continued

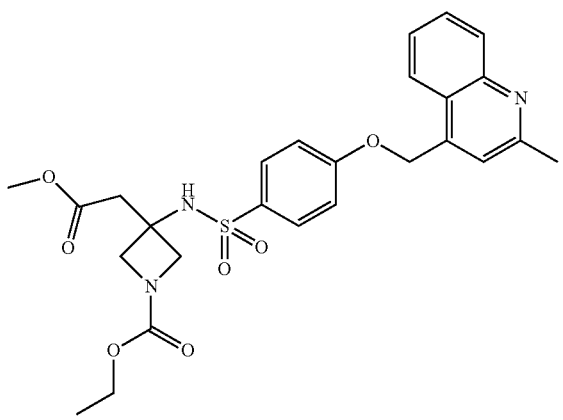

Triethylamine (0.30 ml; 2.19 mmol; 5.00 eq.) was added dropwise to a cooled down suspension of Intermediate B (250.00 mg; 0.44 mmol; 1.00 eq.) in tetrahydrofuran (2.50 ml) at 0° C., followed by ethyl chloroformate (41.97 µl; 0.44 mmol; 1.00 eq.). The reaction mixture was stirred at 0° C. for 30 minutes. The reaction mixture was quenched with water (15 mL) and extracted with ethyl acetate (2*15 mL). The combined organic layers were washed with brine, dried over magnesium sulfate, filtered and concentrated under vacuum. Ethyl 3-(2-methoxy-2-oxoethyl)-3-((4-((2-methylquinolin-4-yl)methoxy)phenyl) sulfonamido)azetidine-1-carboxylate (180.00 mg; 77.73%) was isolated as a white solid.

The examples shown in the following table were all synthesized using a similar protocol as Example 5a starting from the corresponding alkylchloroformate. When necessary, the final compounds were purified either by gel chromatography using dichloromethane/methanol (90/10) as eluent, or by the standard prep HPLC method described above.

| Example number/Name | Structure | NMR | MS(ES+) m/z |
|---|---|---|---|
| Example 5b: methyl 3-(2-(hydroxyamino)-2-oxoethyl)-3-((4-((2-methylquinolin-4-yl)methoxy)phenyl) sulfonamido)azetidine-1-carboxylate | 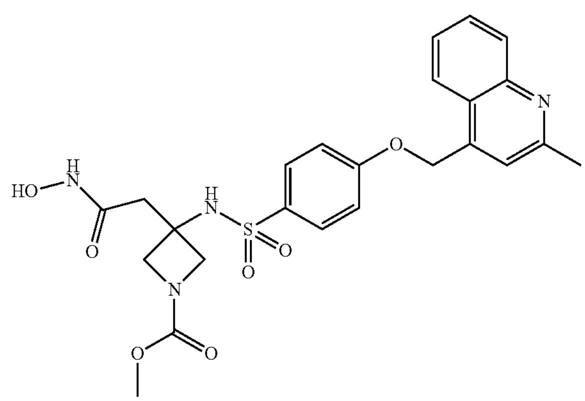 [SMILES: COC(=O)N1CC(CC(=O)NO)(NS(=O)(=O)c2ccc(OCc3cc(C)nc4ccccc34)cc2)C1] | $^1$H NMR (400 MHz, CD$_3$OD): δ (ppm) 2.73 (s, 2H), 3.01 (s, 3H), 3.62 (s, 3H), 4.02 (bs, 4H), 5.99 (s, 2H), 7.36 (d, J = 2.1 Hz, 2H), 7.91 (d, J = 2.1 Hz, 2H), 7.96 (m, 1H), 8.14 (m, 3H), 8.44 (d, J = 2.1 Hz, 1H) | 515 |
| Example 5c: allyl 3-(2-(hydroxyamino)-2-oxoethyl)-3-((4-((2-methylquinolin-4-yl)methoxy)phenyl) sulfonamido)azetidine-1-carboxylate | 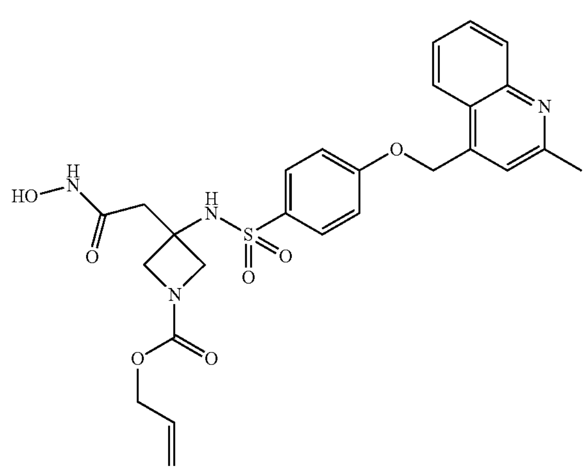 [SMILES: C=CCOC(=O)N1CC(CC(=O)NO)(NS(=O)(=O)c2ccc(OCc3cc(C)nc4ccccc34)cc2)C1] | 1H NMR (400 MHz, DMSO-d6) δ: 2.58 (s, 2H), 2.68 (s, 3H), 3.90 (s, 4H), 4.43 (d, J = 5.1 Hz, 2H), 5.10-5.21 (m, 1H), 5.72 (s, 2H), 5.85 (ddt, J = 17.3, 10.5, 5.3 Hz, 1H), 7.26-7.37 (m, 2H), 7.54-7.65 (m, 2H), 7.72-7.87 (m, 3H), 7.99 (dd, J = 8.5, 1.2 Hz, 1H), 8.11 (dd, J = 8.4, 1.3 Hz, 1H), 8.24 (s, 1H), 8.82 (s, 1H), 10.46 (s, 1H) | 541 |

| Example number/ Name | Structure | NMR | MS(ES+) m/z |
|---|---|---|---|
| Example 5d: isopropyl 3-(2-(hydroxyamino)-2-oxoethyl)-3-((4-((2-methylquinolin-4-yl)methoxy)phenyl)sulfonamido)azetidine-1-carboxylate | 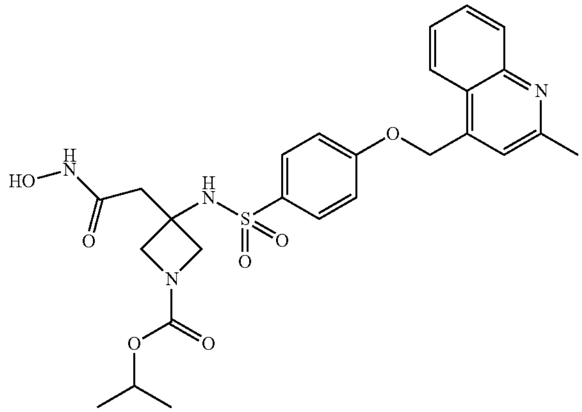 [SMILES: Cc1cc(COc2ccc(S(=O)(=O)NC3(CC(=O)NO)CN(C(=O)OC(C)C)C3)cc2)c2ccccc2n1] | $^1$H NMR (300 MHz, CDCl3): δ 1.21 (d, J = 6.2 Hz, 6H), 2.81 (s, 3H), 3.03 (s, 2H), 3.63 (s, 3H), 3.82 (d, J = 9.5 Hz, 2H), 4.16 (d, J = 9.5 Hz, 2H), 4.87 (septuplet, J = 6.2 Hz, 1H), 5.60 (s, 2H), 5.66 (s, 1H), 7.15 (d, J = 8.9 Hz, 2H), 7.47 (s, 1H), 7.60 (t, J = 8.3 Hz, 1H), 7.78 (t, J = 8.3 Hz, 1H), 7.87 (d, J = 8.9 Hz, 2H), 7.94 (d, J = 8.3 Hz, 1H), 8.17 (d, J = 8.3 Hz, 1H). | 543 |

Example 6

2-(1-acetyl-3-((4-((8-fluoro-2-methylquinolin-4-yl)methoxy)phenyl)sulfonamido) azetidin-3-yl)-N-hydroxyacetamide

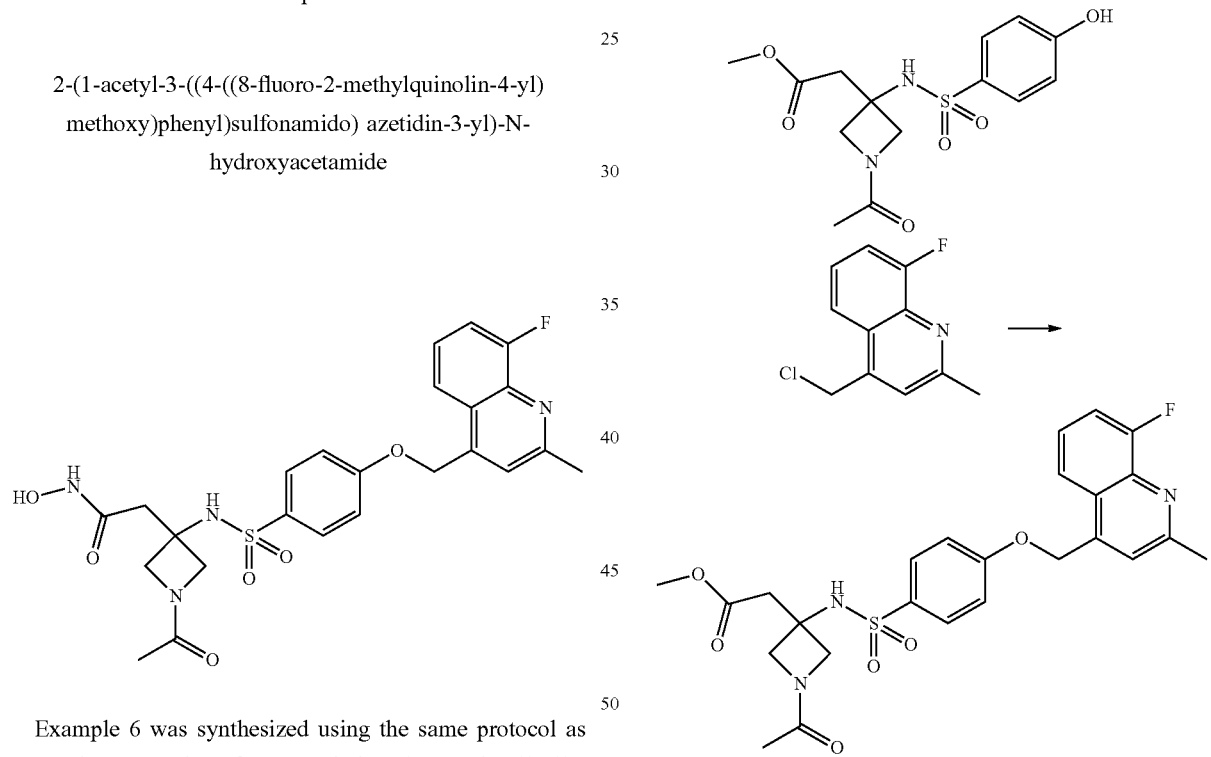

Example 6 was synthesized using the same protocol as Example 1 starting from methyl 2-(1-acetyl-3-((4-((8-fluoro-2-methylquinolin-4-yl)methoxy)phenyl)sulfonamido)azetidin-3-yl)acetate. The final compound was purified by prep HPLC using the standard method.

$^1$H NMR (400 MHz, DMSO-d$_6$) δ: 1.62 (s, 3H), 2.51-2.58 (br s, 2H), 2.70 (s, 3H), 3.75 (d, J=10.1 Hz, 1H), 3.80 (d, J=10.1 Hz, 1H), 4.02-4.11 (m, 2H), 4.17 (d, J=9.1 Hz, 1H), 5.72 (s, 2H), 7.29-7.37 (m, 2H), 7.54-7.64 (m, 2H), 7.66 (s, 1H), 7.77-7.85 (m, 2H), 7.88-7.98 (m, 1H), 8.79 (br s, 1H), 10.42 (br s, 1H)

MS(ES+) m/z 517 (MH+)

Cesium carbonate (157.02 mg; 0.48 mmol; 1.50 eq.) was added portion wise to a cooled down solution of [1-Acetyl-3-(4-hydroxy-benzenesulfonylamino)-azetidin-3-yl]-acetic acid methyl ester (110.00 mg; 0.32 mmol; 1.00 eq.) in N,N-dimethylformamide (1.00 ml) at 0° C. The mixture was stirred for 30 minutes and allowed to warm up to room temperature. 4-Chloromethyl-8-fluoro-2-methyl-quinoline (74.09 mg; 0.35 mmol; 1.10 eq.) was subsequently added followed by sodium iodide (4.82 mg; 0.03 mmol; 0.10 eq.). The reaction mixture is stirred for 12 h at 50° C. The reaction mixture was diluted in methanol and concentrated on silica gel. The mixture was purified by silica gel chromatography using ethanol/dichloromethane (5/95) as eluent. Methyl 2-(1-acetyl-3-((4-((8-fluoro-2-methylquinolin-4-yl)

methoxy)phenyl)sulfonamido)azetidin-3-yl)acetate (92.00 mg; 55.54%) was isolated as a white solid.

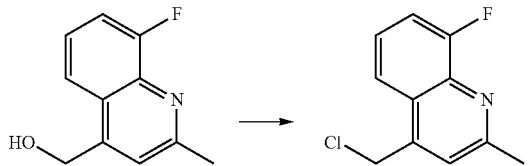

Thionyl Chloride (0.48 ml; 6.64 mmol; 1.50 eq.) was added dropwise to a cooled down solution of (8-fluoro-2-methylquinolin-4-yl)methanol (846.00 mg; 4.42 mmol; 1.00 eq.) in dichloromethane (6.00 ml) at 0° C. The reaction mixture was allowed to warm-up to room temperature slowly. The reaction mixture was concentrated on silica gel under vacuum and purified on silica gel chromatography. 4-Chloromethyl-8-fluoro-2-methyl-quinoline (325.00 mg; 35.04%) was isolated as a gum.

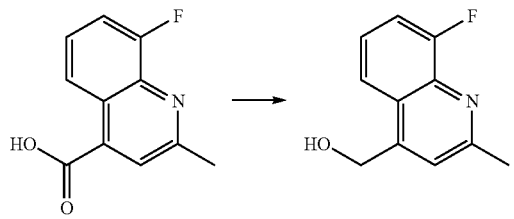

A solution of lithium aluminum hydride 2M in tetrahydrofuran (20.00 ml; 1.00 M; 20.00 mmol; 2.28 eq.) was added dropwise to a cooled down solution of 8-fluoro-2-methylquinoline-4-carboxylic acid (1.80 g; 8.77 mmol; 1.00 eq.) in tetrahydrofuran (30.00 ml) at 0° C. The reaction mixture was stirred at room temperature for 12 hours. Water (760 µL) was added at 0° C. The reaction mixture was diluted in ethyl acetate. A 1N sodium hydroxide solution (760 µL) followed by water (2.280 mL) were subsequently added. Magnesium sulfate was then added and the mixture was stirred 10 minutes at room temperature. The mixture was the filtered through celite and the filtrate concentrated under vacuum. (8-fluoro-2-methylquinolin-4-yl)methanol (846.00 mg; 50.44%) was isolated as a gum.

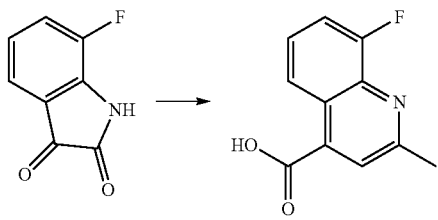

Potassium hydroxide (1.58 g; 28.16 mmol; 3.10 eq.) was added portion wise to a solution of 7-Fluoro-1H-indole-2, 3-dione (1.50 g; 9.08 mmol; 1.00 eq.) in acetone (1.00 ml; 13.63 mmol; 1.50 eq.), ethanol (4.50 ml) and water (1.50 ml) in a microwave tube. The reaction was placed in a microwave oven and heated at 100° C. for 20 min. The reaction mixture was concentrated under vacuum. Water was added followed by a 5N solution of hydrochloric acid until the pH of the solution reached 4. The suspension was then filtered and the solid obtained dried. 8-fluoro-2-methylquinoline-4-carboxylic acid (1.60 g; 85.84%) was isolated as a brown solid.

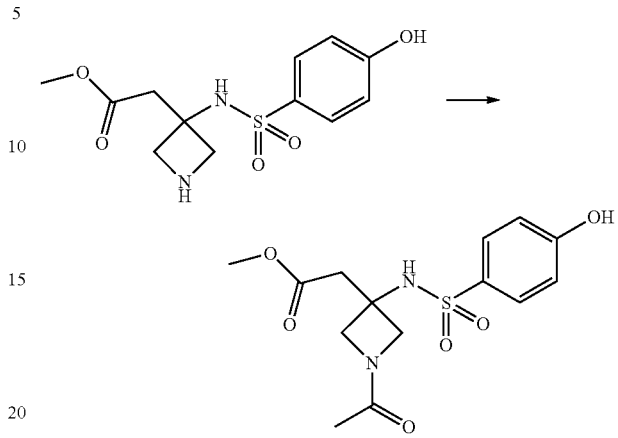

Acetic Anhydride (132.19 µl; 1.40 mmol; 1.05 eq.) was added dropwise to a cooled-down solution of [3-(4-Hydroxy-benzenesulfonylamino)-azetidin-3-yl]-acetic acid methyl ester (400.00 mg; 1.33 mmol; 1.00 eq.) in tetrahydrofuran (10.00 mL) at −15° C. After 5 minutes of stirring, the reaction mixture was quenched at −15° C. with water, followed by ethyl acetate. The aqueous layer was extracted with ethyl acetate and the combined organic layers were washed with brine, dried over magnesium sulfate, concentrated and purified by gel chromatography. [1-Acetyl-3-(4-hydroxy-benzenesulfonylamino)-azetidin-3-yl]-acetic acid methyl ester was isolated as a white solid (360 mg; 79%).

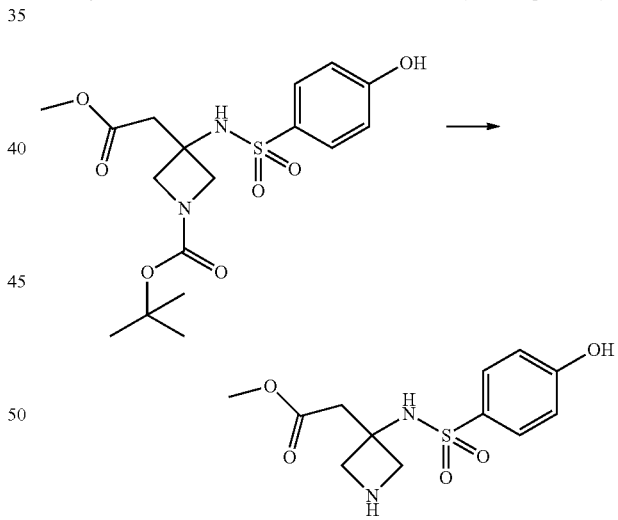

Trifluoroacetic Acid (1.34 ml; 17.48 mmol; 7.00 eq.) was added dropwise to a solution of 3-(4-Hydroxy-benzenesulfonylamino)-3-methoxycarbonyl methyl-azetidine-1-carboxylic acid tert-butyl ester (1.00 g; 2.50 mmol; 1.00 eq.) in dichloromethane (10 mL) at room temperature. After 6 hours, the reaction mixture was concentrated. Dichloromethane and a 1N solution of NaOH were added. The aqueous layer was extracted with dichloromethane and the combined organic layers were washed with brine, dried over Magnesium sulfate and concentrated to yield [3-(4-Hydroxy-benzenesulfonylamino)-azetidin-3-yl]acetic acid methyl ester as a gum (550.00 mg; 73.33%).

Example 7a

N-hydroxy-3-((4-((2-methylquinolin-4-yl)methoxy)phenyl)sulfonamido)-1-pivaloylazetidine-3-carboxamide

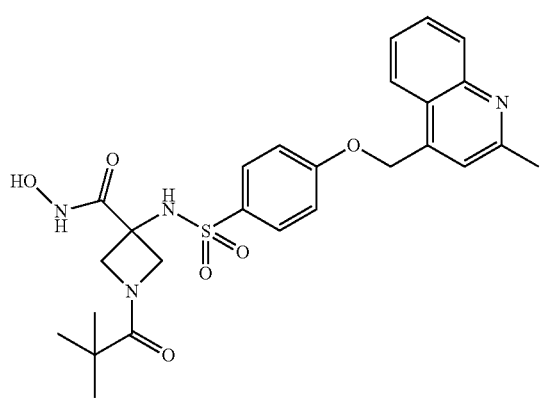 [SMILES: Cc1cc(COc2ccc(S(=O)(=O)NC3(C(=O)NO)CN(C(=O)C(C)(C)C)C3)cc2)c2ccccc2n1]

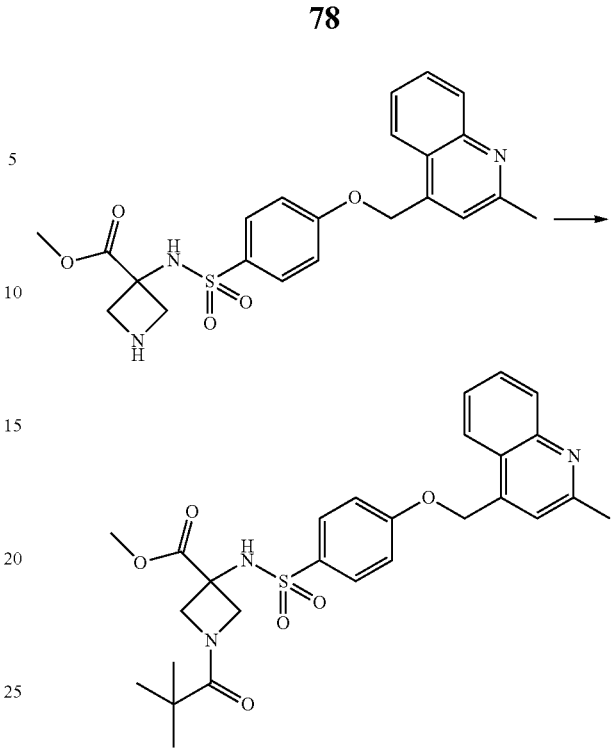

Hydroxylamine aqueous solution (50%) (0.30 ml; 4.95 mmol; 10.00 eq.) and 1,8-diazabicyclo[5.4.0]undec-7-ene (0.30 ml; 1.98 mmol; 4.00 eq.) were added dropwise to a solution of methyl 3-((4-((2-methylquinolin-4-yl)methoxy)phenyl)sulfonamido)-1-pivaloylazetidine-3-carboxylate (260.00 mg; 0.49 mmol; 1.00 eq.) in methanol (1.30 ml). The reaction mixture was stirred 2 hours at room temperature. The reaction mixture was purified by the standard prep HPLC method. N-hydroxy-3-((4-((2-methylquinolin-4-yl)methoxy)phenyl)sulfonamido)-1-pivaloylazetidine-3-carboxamide (160.00 mg; 61.42%) was isolated as white crystals.

$^1$H NMR (400 MHz, DMSO-$d_6$) δ: 0.97 (s, 9H), 2.68 (s, 3H), 3.81 (s, 1H), 3.94 (s, 1H), 4.15 (s, 1H), 4.59 (s, 1H), 5.73 (s, 2H), 7.29-7.41 (m, 2H), 7.54-7.67 (m, 2H), 7.71-7.84 (m, 3H), 7.99 (dd, J=8.4, 1.2 Hz, 1H), 8.11 (dd, J=8.4, 1.3 Hz, 1H), 8.94 (s, 1H)

MS(ES+) m/z 527 (MH+)

Triethylamine (0.41 ml; 2.99 mmol; 4.00 eq.) was added dropwise to a cooled-down suspension of Intermediate E (500.00 mg; 0.75 mmol; 1.00 eq.) in tetrahydrofuran (7.50 ml) at 5° C., followed by dropwise addition of pivaloyl chloride (90.04 mg; 0.75 mmol; 1.00 eq.). The reaction mixture was stirred at 0° C. for 60 minutes. 5 mL of water were added to the reaction mixture, followed by 10 mL of ethyl acetate. The organic layer was washed with brine, dried over magnesium sulfate, concentrated and purified by gel chromatography. Methyl 3-((4-((2-methylquinolin-4-yl)methoxy)phenyl)sulfonamido)-1-pivaloylazetidine-3-carboxylate (260.00 mg; 66.24%) was isolated as a white solid.

The examples shown in the following table were all synthesized using a similar protocol as Example 7a starting from the corresponding acyl chlorides.

| Example number/ Name | Structure | NMR | MS(ES+) m/z (MH+) |
|---|---|---|---|
| Example 7b: N-hydroxy-1-isobutyryl-3-((4-((2-methylquinolin-4-yl)methoxy)phenyl)sulfonamido)azetidine-3-carboxamide | 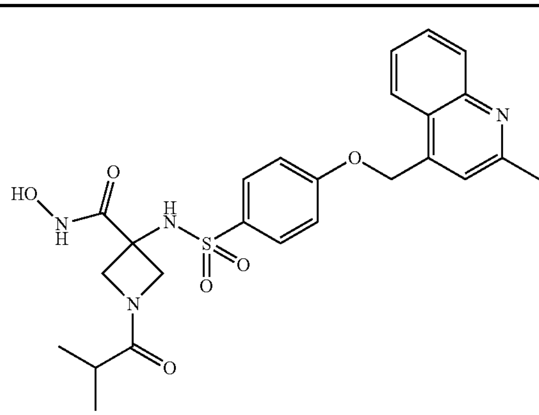 | $^1$H NMR (400 MHz, DMSO-$d_6$) δ: 2.19 (qt, J = 11.6, 7.3 Hz, 2H), 2.45-2.49 (m, 2H), 2.68 (s, 3H), 3.08 (d, J = 7.8 Hz, 2H), 3.44-3.51 (m, 2H), 5.71 (s, 2H), 7.21-7.32 (m, 2H), 7.54-7.66 (m, 2H), 7.69-7.83 (m, 3H), 7.99 (dd, J = 8.3, 1.2 Hz, 1H), 8.12 (dd, J = 8.4, 1.4 Hz, 1H), 9.10 (s, 1H) | 513 |

-continued

| Example number/ Name | Structure | NMR | MS(ES+) m/z (MH+) |
|---|---|---|---|
| Example 7c: N-hydroxy-1-(3-methylbutanoyl)-3-((4-((2-methylquinolin-4-yl)methoxy)phenyl)sulfonamido)azetidine-3-carboxamide | 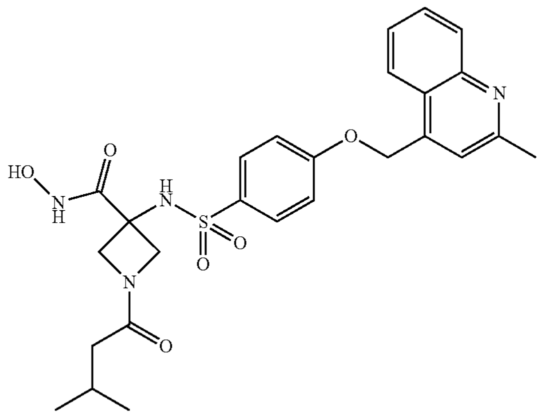 [SMILES: Cc1cc(COc2ccc(S(=O)(=O)NC3(C(=O)NO)CN(C(=O)CC(C)C)C3)cc2)c2ccccc2n1] | $^1$H NMR (400 MHz, DMSO-$d_6$) δ 0.81 (dd, J = 10.4, 6.1 Hz, 6H), 1.63-1.96 (m, 3H), 2.68 (s, 3H), 3.76 (d, J = 10.2 Hz, 1H), 4.00 (dd, J = 9.6, 4.3 Hz, 2H), 4.35 (d, J = 9.2 Hz, 1H), 5.73 (s, 2H), 7.22-7.45 (m, 2H), 7.47-7.66 (m, 2H), 7.68-7.89 (m, 3H), 7.99 (dd, J = 8.5, 1.2 Hz, 1H), 8.11 (dd, J = 8.2, 1.5 Hz, 1H | 527 |
| Example 7d: N-hydroxy-3-((4-((2-methylquinolin-4-yl)methoxy)phenyl)sulfonamido)-1-(tetrahydro-2H-pyran-4-carbonyl)azetidine-3-carboxamide | 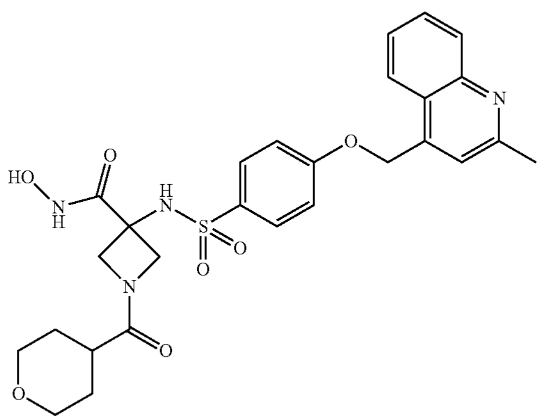 | $^1$H NMR (400 MHz, DMSO-$d_6$) δ: 1.31 (d, J = 13.1 Hz, 1H), 1.45 (tq, J = 9.0, 4.5, 4.1 Hz, 3H), 2.27-2.42 (m, 1H), 2.68 (s, 3H), 3.28 (td, J = 11.7, 2.6 Hz, 2H), 3.73-3.85 (m, 3H), 3.99 (d, J = 10.1 Hz, 1H), 4.09 (d, J = 9.3 Hz, 1H), 4.45 (d, J = 9.3 Hz, 1H), 5.73 (s, 2H), 7.28-7.42 (m, 2H), 7.51-7.67 (m, 2H), 7.71-7.84 (m, 3H), 7.99 (dd, J = 8.5, 1.2 Hz, 1H), 8.12 (dd, J = 8.4, 1.3 Hz, 1H), 8.94 (s, 1H) | 555 |
| Example 7e: 1-(cyclobutanecarbonyl)-N-hydroxy-3-((4-((2-methylquinolin-4-yl)methoxy)phenyl)sulfonamido)azetidine-3-carboxamide | 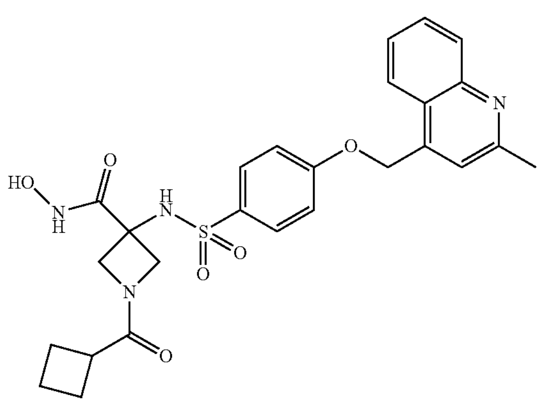 [SMILES: Cc1cc(COc2ccc(S(=O)(=O)NC3(C(=O)NO)CN(C(=O)C4CCC4)C3)cc2)c2ccccc2n1] | $^1$H NMR (400 MHz, DMSO-$d_6$) δ: 1.71 (tt, J = 9.6, 4.0 Hz, 1H), 1.77-2.12 (m, 5H), 2.68 (s, 3H), 3.76 (d, J = 10.2 Hz, 1H), 3.91 (d, J = 9.2 Hz, 1H), 3.99 (d, J = 10.0 Hz, 1H), 4.26 (d, J = 9.2 Hz, 1H), 5.73 (s, 2H), 7.27-7.41 (m, 2H), 7.51-7.68 (m, 2H), 7.71-7.84 (m, 3H), 7.99 (dd, J = 8.4, 1.2 Hz, 1H), 8.11 (dd, J = 8.6, 1.4 Hz, 1H), 8.92 (s, 1H), 10.69 (s, 1H) | 525 |

| Example number/ Name | Structure | NMR | MS(ES+) m/z (MH+) |
|---|---|---|---|
| Example 7f: 1-(2-ethylbutanoyl)-N-hydroxy-3-((4-((2-methylquinolin-4-yl)methoxy)phenyl)sulfonamido)azetidine-3-carboxamide | 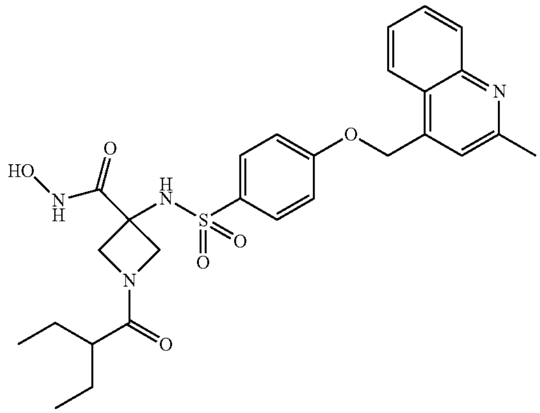 [SMILES: CCC(CC)C(=O)N1CC(NS(=O)(=O)c2ccc(OCc3cc(C)nc4ccccc34)cc2)(C(=O)NO)C1] | ¹H NMR (400 MHz, DMSO) δ: 0.63 (t, J = 7.4 Hz, 3H), 0.74 (t, J = 7.4 Hz, 3H), 1.30 (ddtd, J = 25.9, 19.6, 13.6, 6.7 Hz, 4H), 1.91 (td, J = 8.8, 4.4 Hz, 1H), 2.68 (s, 3H), 3.80 (d, J = 10.2 Hz, 1H), 3.99 (d, J = 9.8 Hz, 2H), 4.40 (d, J = 9.1 Hz, 1H), 5.72 (s, 2H), 7.27-7.38 (m, 2H), 7.52-7.66 (m, 2H), 7.70-7.87 (m, 3H), 7.99 (d, J = 8.4 Hz, 1H), 8.06-8.15 (m, 1H), 8.95 (s, 1H) | 541 |
| Example 7g: N-hydroxy-3-((4-((2-methylquinolin-4-yl)methoxy)phenyl)sulfonamido)-1-propionylazetidine-3-carboxamide | 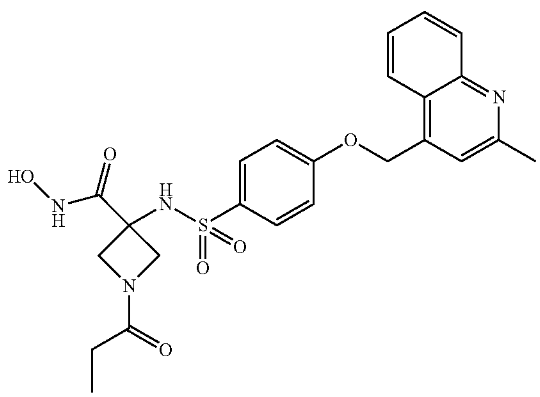 [SMILES: CCC(=O)N1CC(NS(=O)(=O)c2ccc(OCc3cc(C)nc4ccccc34)cc2)(C(=O)NO)C1] | ¹H NMR (400 MHz, DMSO-d₆) δ: 0.89 (t, J = 7.5 Hz, 3H), 1.94 (dd, J = 14.2, 7.5 Hz, 2H), 2.68 (s, 3H), 3.75 (d, J = 10.1 Hz, 1H), 4.00 (d, J = 9.5 Hz, 2H), 4.33 (d, J = 9.0 Hz, 1H), 5.73 (s, 2H), 7.25-7.39 (m, 2H), 7.53-7.65 (m, 2H), 7.70-7.84 (m, 3H), 7.99 (dd, J = 8.6, 1.2 Hz, 1H), 8.12 (dd, J = 8.3, 1.4 Hz, 1H) | 499 |
| Example 7h: 1-butyryl-N-hydroxy-3-((4-((2-methylquinolin-4-yl)methoxy)phenyl)sulfonamido)azetidine-3-carboxamide | 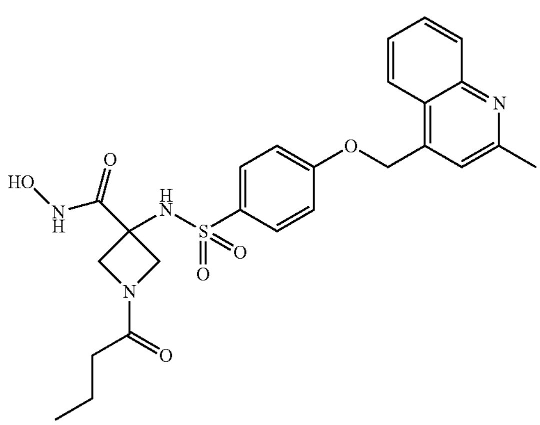 [SMILES: CCCC(=O)N1CC(NS(=O)(=O)c2ccc(OCc3cc(C)nc4ccccc34)cc2)(C(=O)NO)C1] | ¹H NMR (400 MHz, DMSO-d6) δ: 0.77-0.81 (t, J = 7.3 Hz, 3H), 1.35-1.44 (q, J = 7.4 Hz, 2H), 1.83-1.97 (m, 2H), 2.67 (s, 3H), 3.74-3.76 (d, J = 10.2 Hz, 1H), 3.98-4.01 (d, J = 9.9 Hz, 2H), 4.33-4.35 (d, J = 9.2 Hz, 1H), 5.72 (s, 2H), 7.33-7.35 (d, J = 8.9 Hz, 2H), 7.57 (s, 1H), 7.58-7.62 (td, J = 6.9-1.2 Hz, 1H), 7.74-7.79 (m, 3H), 7.97-8.00 (d, J = 8.4 Hz, 1H), 8.10-8.12 (d, J = 7.7 Hz, 1H), 8.55 (s, 1H), 8.93 (s, 1H), 10.71 (s, 1H) | (ES-) m/z 511 (MH-) |

| Example number/ Name | Structure | NMR | MS(ES+) m/z (MH+) |
|---|---|---|---|
| Example 7i: N-hydroxy-3-((4-((2-methylquinolin-4-yl)methoxy)phenyl)sulfonamido)-1-pentanoylazetidine-3-carboxamide | 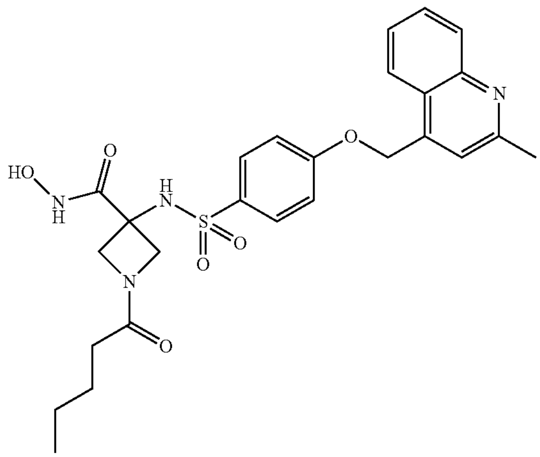 [SMILES: CCCCC(=O)N1CC(NS(=O)(=O)c2ccc(OCc3cc(C)nc4ccccc34)cc2)(C(=O)NO)C1] | $^1$H NMR (400 MHz, DMSO-$d_6$): δ (ppm) 10.73 (s, 1H), 8.94 (s, 1H), 8.55 (s, 1H), 8.12 (d, J = 8.4 Hz, 1H), 7.99 (d, J = 8.4 Hz, 1H), 7.83-7.71 (m, 3H), 7.66-7.52 (m, 2H), 7.35 (d, J = 8.7 Hz, 2H), 5.73 (s, 2H), 4.34 (d, J = 9.1 Hz, 1H), 3.99 (d, J = 9.9 Hz, 2H), 3.76 (d, J = 10.1 Hz, 1H), 2.68 (s, 3H), 2.02-1.79 (m, 2H), 1.35 (m, 2H), 1.21 (m, 2H), 0.81 (t, J = 7.3 Hz, 3H). | |

Example 8

1-acetyl-N-hydroxy-3-((4-((2-methylquinolin-4-yl)methoxy)phenyl)sulfonamido) azetidine-3-carboxamide

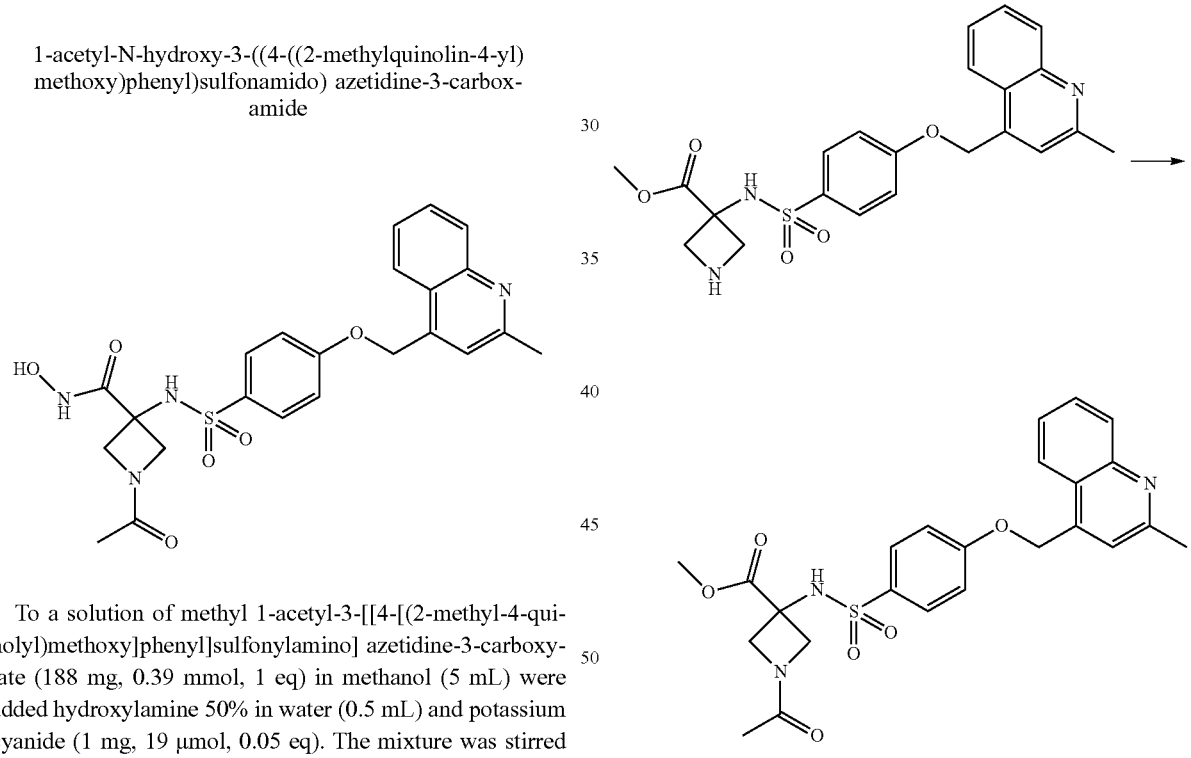

To a solution of methyl 1-acetyl-3-[[4-[(2-methyl-4-quinolyl)methoxy]phenyl]sulfonylamino] azetidine-3-carboxylate (188 mg, 0.39 mmol, 1 eq) in methanol (5 mL) were added hydroxylamine 50% in water (0.5 mL) and potassium cyanide (1 mg, 19 μmol, 0.05 eq). The mixture was stirred at room temperature overnight. The mixture was concentrated and purified by preparative chromatography to give 1-acetyl-3-[[4-[(2-methyl-4-quinolyl)methoxy]phenyl]sulfonylamino]azetidine-3-carbohydroxamic acid as a white solid (80 mg, 42.5%).

$^1$H NMR (300 MHz, DMSO-$d_6$): δ 1.65 (s, 3H), 2.66 (s, 3H), 3.71 (d, J=10.1 Hz, 1H), 3.93-4.06 (m, 2H), 4.32 (d, J=9.5 Hz, 1H), 5.72 (s, 2H), 7.33 (d, J=9.1 Hz, 2H), 7.54-7.63 (d, 2H), 7.70-7.81 (m, 3H), 7.97 (d, J=8.4 Hz, 1H), 8.10 (d, J=8.4 Hz, 1H), 8.13 (s, 1H), 8.54 (s, 1H), 10.72 (s, 1H).

MS(ES+) m/z 485 (MH+)

To a suspension of Intermediate E (200 mg, 0.39 mmol, 1 eq) in dichloromethane (5 mL) were added triethylamine (525 μL, 3.89 mmol, 10 eq) and acetic anhydride (39 μL, 0.41 mmol, 1.05 eq). The mixture was stirred at room temperature for 15 min then was washed with a saturated solution of NaHCO$_3$. The organic layer was dried over magnesium sulfate, filtered and the solvent was removed under reduced pressure to give methyl 1-acetyl-3-[[4-[(2-methyl-4-quinolyl)methoxy]phenyl]sulfonylamino]azetidine-3-carboxylate as a yellow oil (165 mg, 87.8%). The compound was used in the next step without further purification.

Example 9

N-hydroxy-2-(3-((4-((2-methylquinolin-4-yl)methoxy)phenyl)sulfonamido)-1-(piperidine-1-carbonyl)azetidin-3-yl)acetamide

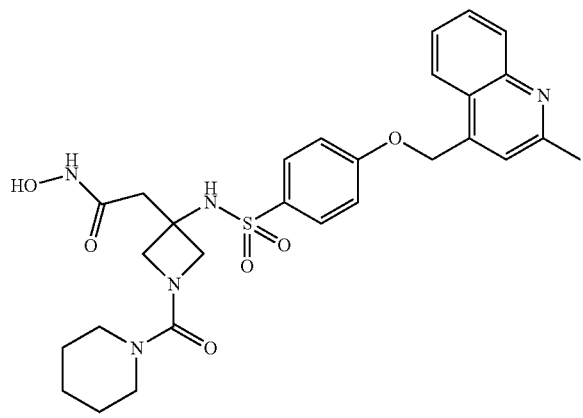

Example 9 was synthesized using the same protocol as Example 1 starting from methyl 2-(3-((4-((2-methylquinolin-4-yl)methoxy)phenyl)sulfonamido)-1-(piperidine-1-carbonyl)azetidin-3-yl)acetate. The final compound was purified by prep HPLC using the standard method.

$^1$H NMR (400 MHz, DMSO-d$_6$): δ (ppm) 8.78 (s, 1H), 8.18 (s, 1H), 8.10-8.12 (d, J=8.2 Hz, 1H), 7.97-7.99 (d, J=8.0 Hz, 1H), 7.81-7.83 (d, J=8.8 Hz, 2H), 7.74-7.78 (td, J=7.0-1.2 Hz, 1H), 7.57-7.61 (td, J=8.2-1.1 Hz, 1H), 7.57 (s, 1H), 7.31-7.34 (d, J=8.9 Hz, 2H), 5.70 (s, 2H), 3.78-3.84 (q, J=8.8 Hz, 4H), 2.98-3.00 (t, J=5.3 Hz, 4H), 2.67 (s, 3H), 2.53 (s, 2H), 1.42-1.45 (m, 2H), 1.31-1.33 (m, 4H)

MS(ES+) m/z 568 (MH+)

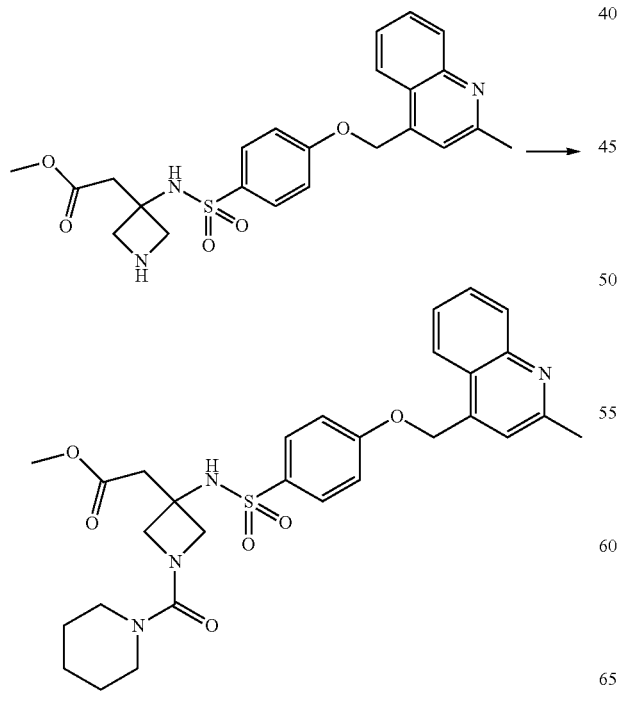

Triethylamine (219.05 μl; 1.58 mmol; 3.00 eq.) was added dropwise to a cooled-down solution of Intermediate B (300.00 mg; 0.53 mmol; 1.00 eq.) in tetrahydrofuran (6.00 ml) at 0° C., followed by 1-piperidinecarbonyl chloride (65.89 μl; 0.53 mmol; 1.00 eq.). The reaction mixture was stirred for 45 min and then quenched with water. Extraction was done with ethyl acetate. The combined organic layers were washed with brine, dried over magnesium sulfate and concentrated. [3-[4-(2-Methyl-quinolin-4-ylmethoxy)-benzenesulfonylamino]-1-(piperidine-1-carbonyl)-azetidin-3-yl]-acetic acid methyl ester (350.00 mg; 117.26%) was isolated as a white solid.

Example 10

N-hydroxy-2-(1-(4-methylpiperazine-1-carbonyl)-3-((4-((2-methylquinolin-4-yl)methoxy)phenyl)sulfonamido)azetidin-3-yl)acetamide

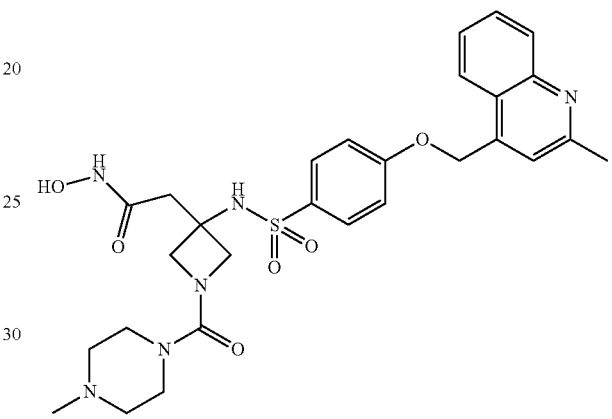

Example 10 was synthesized using the same protocol as Example 9 starting from 4-methylpiperazine-1-carbonyl chloride.

1H NMR (400 MHz, DMSO-d$_6$): δ (ppm) 10.45 (s, 1H), 8.79 (s, 1H), 8.17 (s, 1H), 8.10-8.12 (d, J=8.3 Hz, 1H), 7.97-7.99 (d, J=7.8 Hz, 1H), 7.81-7.84 (d, J=8.9 Hz, 2H), 7.74-7.78 (td, J=7.0-1.3 Hz, 1H), 7.58-7.62 (td, J=6.9-1.2 Hz, 1H), 7.57 (s, 1H), 7.32-7.34 (d, J=9.0 Hz, 1H), 5.71 (s, 2H), 3.80-3.87 (q, J=8.8 Hz, 4H), 3.02-3.04 (t, J=4.8 Hz, 4H), 2.67 (s, 3H), 2.55 (s, 2H), 2.12-2.15 (t, J=4.8 Hz, 4H), 2.09 (s, 3H).

MS(ES+) m/z 583 (MH+)

Example 11

2-(1-(3,3-dimethylbutanoyl)-3-((4-((2-methylquinolin-4-yl)methoxy)phenyl) sulfonamido)azetidin-3-yl)-N-hydroxyacetamide

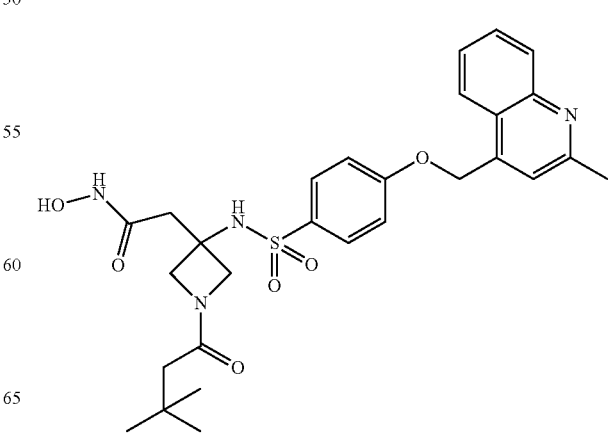

Example 11 was synthesized using the same protocol as Example 7a starting from Methyl-2-(1-(3,3-dimethylbutanoyl)-3-((4-((2-methylquinolin-4-yl)methoxy)phenyl) sulfonamido)azetidin-3-yl)acetate.

¹H NMR (400 MHz, DMSO-d₆): δ (ppm) 0.86 (s, 9H), 1.73-1.82 (q, J=13.6-8.8 Hz, 2H), 2.56 (s, 2H), 2.67 (s, 3H), 3.75-3.83 (q, J=10.0-10.3 Hz, 2H), 4.05-4.07 (d, J=9.1 Hz, 1H), 4.16-4.18 (d, J=9.0 Hz, 1H), 5.71 (s, 2H), 7.31-7.33 (d, J=8.8 Hz, 2H), 7.57 (s, 1H), 7.58-7.61 (t, J=7.6 Hz, 1H), 7.74-7.78 (t, J=7.6 Hz, 1H), 7.80-7.82 (d, J=8.8 Hz, 2H), 7.97-7.99 (d, J=8.4 Hz, 1H), 8.10-8.12 (d, J=8.3 Hz, 1H), 8.24 (s, 1H), 8.79 (s, 1H), 10.46 (s, 1H).

MS(ES+) m/z 555 (MH+)

Methyl 2-(1-(3,3-dimethylbutanoyl)-3-((4-((2-methylquinolin-4-yl)methoxy)phenyl) sulfonamido)azetidin-3-yl)acetate was synthesized using the same protocol described for Example 4a starting from Intermediate B and 3,3-dimethylbutanoyl chloride.

Example 12

N-hydroxy-2-(3-((4-((2-methylquinolin-4-yl)methoxy)phenyl)sulfonamido)-1-(2-(piperidin-1-yl)acetyl)azetidin-3-yl)acetamide

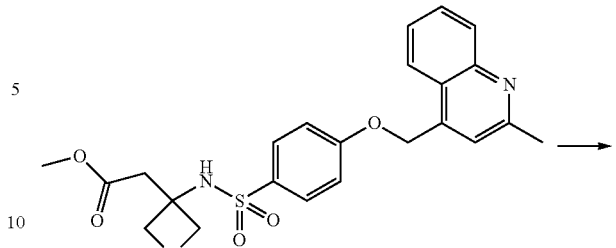

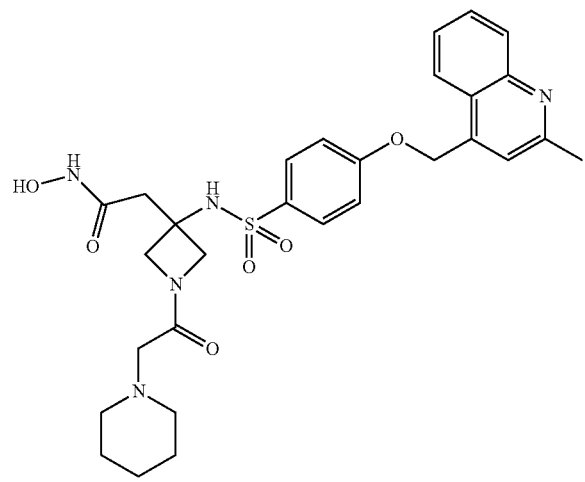 [SMILES: Cc1cc(COc2ccc(S(=O)(=O)NC3(CC(=O)NO)CN(C(=O)CN4CCCCC4)C3)cc2)c2ccccc2n1]

Example 12 was synthesized using the same protocol as Example 1 starting from methyl 2-(3-((4-((2-methylquinolin-4-yl)methoxy)phenyl)sulfonamido)-1-(2-(piperidin-1-yl)acetyl)azetidin-3-yl)acetate.

¹H NMR (400 MHz, DMSO-d₆): δ (ppm) 1.28-1.30 (m, 2H), 1.38-1.39 (m, 4H), 2.20 (m, 4H), 2.57 (s, 2H), 2.67 (s, 3H), 2.68-2.70 (d, 1H), 2.82-2.85 (d, 1H), 3.78-3.81 (d, 1H), 3.86-3.88 (d, 1H), 4.14-4.22 (q, 2H), 5.71 (s, 2H), 7.32-7.34 (d, 1H), 7.58 (s, 1H), 7.60-7.62 (t, 1H), 7.74-7.78 (t, 1H), 7.81-7.83 (d, 1H), 7.97-7.99 (d, 1H), 8.10-8.12 (d, 1H), 8.23 (s, 1H), 8.80 (s, 1H), 10.46 (s, 1H)

MS(ES-) m/z 581 (MH-)

1-Ethyl-3-(3-dimethylaminopropyl)carbodiimide hydrochloride (201.95 mg; 1.05 mmol; 1.20 eq.) and 1-Oxy-pyridin-2-ol (117.04 mg; 1.05 mmol; 1.20 eq.) were sequentially added dropwise to a solution of piperidin-1-yl-acetic acid (150.84 mg; 1.05 mmol; 1.20 eq.) in N,N-dimethylformamide (7.50 ml) at room temperature. The reaction mixture was stirred for 10 minutes. {3-[4-(2-methyl-quinolin-4-ylmethoxy)-benzenesulfonylamino]-azetidin-3-yl}-acetic acid methyl ester (500.00 mg; 0.88 mmol; 1.00 eq.) et N,N-diisopropylethylamine (453.25 µl; 2.63 mmol; 3.00 eq.) were then added to the reaction mixture. The reaction mixture was stirred for 10 minutes. Ethyl acetate and water were added to the reaction mixture. The aqueous layer was extracted with more ethyl acetate and the combined organic layers were washed with brine, dried over magnesium sulfate and concentrated. Purification by silica gel chromatography yielded methyl 2-(3-((4-((2-methylquinolin-4-yl)methoxy)phenyl)sulfonamido)-1-(2-(piperidin-1-yl)acetyl)azetidin-3-yl)acetate (242.00 mg; 47.47%) as a white solid.

Example 13

2-(1-(2-cyclobutylacetyl)-3-((4-((2-methylquinolin-4-yl)methoxy)phenyl)sulfonamido) azetidin-3-yl)-N-hydroxyacetamide

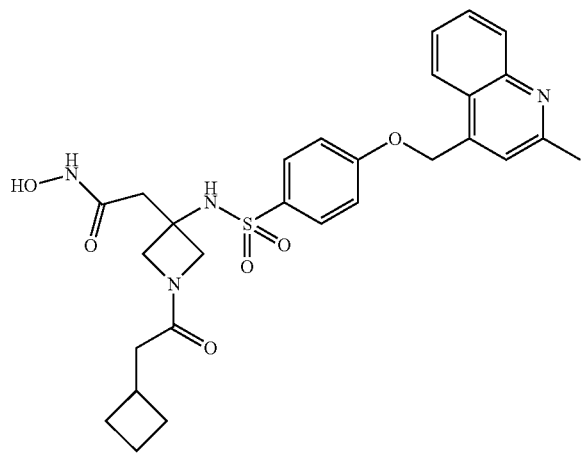 [SMILES: Cc1cc(COc2ccc(S(=O)(=O)NC3(CC(=O)NO)CN(C(=O)CC4CCC4)C3)cc2)c2ccccc2n1]

Example 13 was synthesized using the same protocol as Example 1 starting from methyl 2-[1-(2-cyclobutylacetyl)-3-[[4-[(2-methyl-4-quinolyl)methoxy]phenyl] sulfonylamino] azetidin-3-yl]acetate.

$^1$H NMR (300 MHz, DMSO-d$_6$) δ 1.43-1.64 (m, 2H), 1.64-1.81 (m, 2H), 1.85-2.05 (m, 4H), 2.34-2.58 (m, 3H), 2.66 (s, 3H), 3.70-3.84 (m, 2H), 4.03 (d, J=9.0 Hz, 1H), 4.16 (d, J=9.0 Hz, 1H), 5.70 (s, 2H), 7.32 (d, J=8.9 Hz, 2H), 7.52-7.63 (m, 2H), 7.70-7.85 (m, 3H), 7.97 (d, J=8.1 Hz, 1H), 8.09 (d, J=8.1 Hz, 1H), 8.16-8.34 (m, 2H), 10.46 (s, 1H).

MS(ES+) m/z 485 (MH+)

To a suspension of methyl 2-[3-[[4-[(2-methyl-4-quinolyl)methoxy]phenyl] sulfonylamino]azetidin-3-yl]acetate 2,2,2-trifluoroacetic acid (500 mg, 0.88 mmol, 1 eq) in dichloromethane (9 mL) were added diisobutylethymamine (328.44 µl, 1.9 mmol, 2.2 eq), 2-cyclobutylacetic acid (105.21 mg, 0.92 mmol, 1.05 eq), N-(3-dimethylaminopropyl)-N'-ethylcarbodiimide hydrochloride (176.71 mg, 0.92 mmol, 1.05 eq) and hydroxybenzotriazole (141.16 mg, 0.92 mmol, 1.05 eq). The mixture was stirred at room temperature overnight then water was added. The organic layer was extracted with ethylacetate, dried on magnesium sulfate, and concentrated under vacuo affording methyl 2-[1-(2-cyclobutylacetyl)-3-[[4-[(2-methyl-4-quinolyl)methoxy]phenyl]sulfonylamino] azetidin-3-yl]acetate as a white solid (484.3 mg, 78.5% yield).

Example 14

Tert-butyl 3-(hydroxycarbamoyl)-3-((4-((2-methylquinolin-4-yl)methoxy)phenyl) sulfonamido)azetidine-1-carboxylate

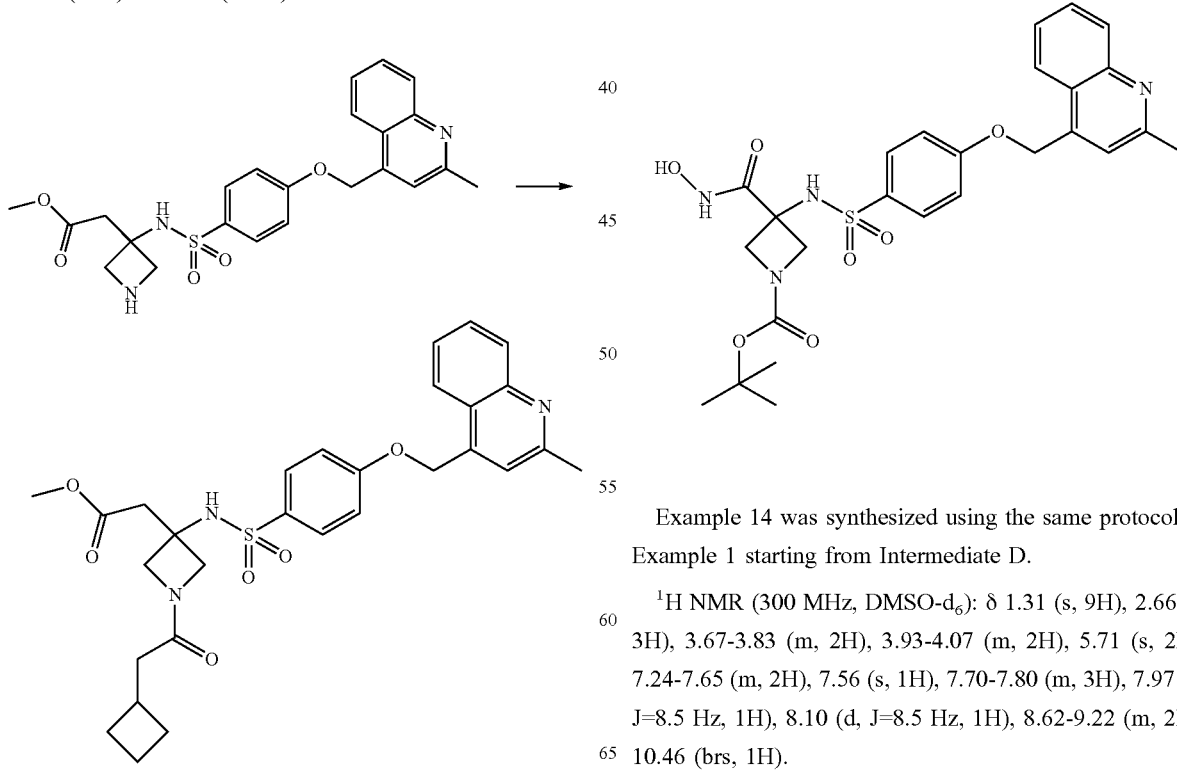

Example 14 was synthesized using the same protocol as Example 1 starting from Intermediate D.

$^1$H NMR (300 MHz, DMSO-d$_6$): δ 1.31 (s, 9H), 2.66 (s, 3H), 3.67-3.83 (m, 2H), 3.93-4.07 (m, 2H), 5.71 (s, 2H), 7.24-7.65 (m, 2H), 7.56 (s, 1H), 7.70-7.80 (m, 3H), 7.97 (d, J=8.5 Hz, 1H), 8.10 (d, J=8.5 Hz, 1H), 8.62-9.22 (m, 2H), 10.46 (brs, 1H).

MS(ES+) m/z 553 (MH+)

Example 15

1-(3,3-dimethylbutanoyl)-N-hydroxy-3-((4-((2-methylquinolin-4-yl)methoxy)phenyl) sulfonamido)azetidine-3-carboxamide

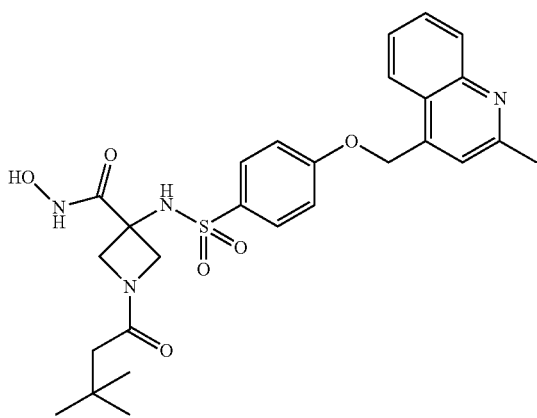

Example 15 was synthesized using the same protocol as Example 8 starting from methyl 1-(3,3-dimethylbutanoyl)-3-((4-((2-methylquinolin-4-yl)methoxy)phenyl)sulfonamido)azetidine-3-carboxylate.

$^1$H NMR (300 MHz, CD$_2$Cl$_2$): δ 0.98 (s, 9H), 1.93 (s, 2H), 2.76 (s, 3H), 3.61 (s, 3H), 4.07 (d, J=10.2 Hz, 1H), 4.15 (d, J=10.2 Hz, 1H), 4.38 (d, J=9.1 Hz, 1H), 4.49 (d, J=9.1 Hz, 1H), 5.61 (s, 2H), 5.65 (s, 1H), 7.16 (d, J=8.8 Hz, 2H), 7.48 (s, 1H), 7.58 (t, J=8.1 Hz, 1H), 7.70-7.85 (m, 3H), 7.96 (d, J=8.1 Hz, 1H), 8.12 (d, J=8.1 Hz, 1H).

MS(ES+) m/z 541 (MH+)

Methyl 1-(3,3-dimethylbutanoyl)-3-((4-((2-methylquinolin-4-yl)methoxy)phenyl)sulfonamido)azetidine-3-carboxylate was synthesized using the same protocol described for Example 7a using Intermediate E and 3,3-dimethylbutanoyl chloride.

Example 16a

N-hydroxy-3-((4-((2-methylquinolin-4-yl)methoxy)phenyl)sulfonamido)-1-(piperidine-1-carbonyl)azetidine-3-carboxamide

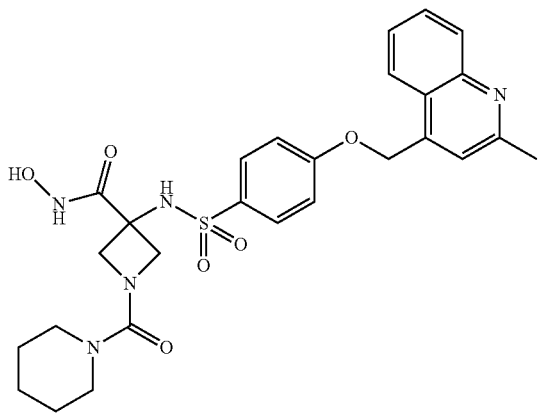

Example 16a was synthesized using the same protocol as Example 7a starting from methyl 3-((4-((2-methylquinolin-4-yl)methoxy)phenyl)sulfonamido)-1-(piperidine-1-carbonyl)azetidine-3-carboxylate.

$^1$H NMR (400 MHz, DMSO-d$_6$) δ: 1.31 (d, J=13.1 Hz, 1H), 1.45 (tq, J=9.0, 4.5, 4.1 Hz, 3H), 2.27-2.42 (m, 1H), 2.68 (s, 3H), 3.28 (td, J=11.7, 2.6 Hz, 2H), 3.73-3.85 (m, 3H), 3.99 (d, J=10.1 Hz, 1H), 4.09 (d, J=9.3 Hz, 1H), 4.45 (d, J=9.3 Hz, 1H), 5.73 (s, 2H), 7.28-7.42 (m, 2H), 7.51-7.67 (m, 2H), 7.71-7.84 (m, 3H), 7.99 (dd, J=8.5, 1.2 Hz, 1H), 8.12 (dd, J=8.4, 1.3 Hz, 1H), 8.94 (s, 1H)

MS(ES+) m/z 554 (MH+)

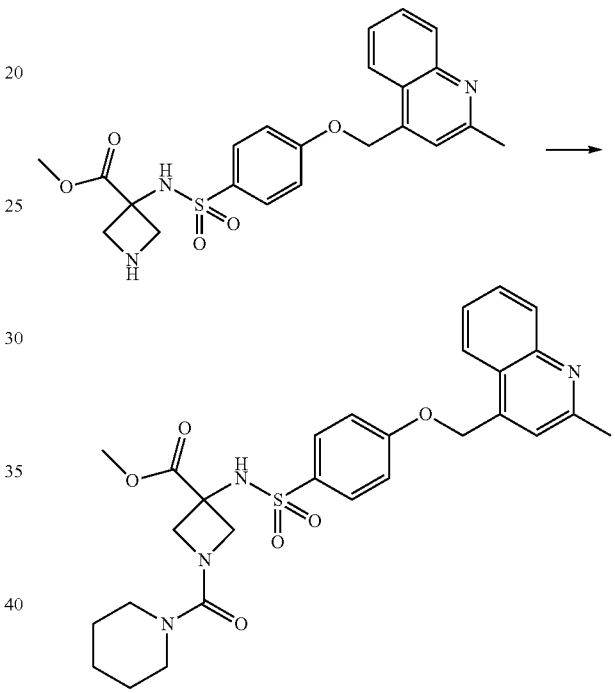

Triethylamine (0.33 ml; 2.39 mmol; 4.00 eq.) was added dropwise to a cooled down suspension of Intermediate E (400.00 mg; 0.60 mmol; 1.00 eq.) in tetrahydrofuran (6.00 ml) at 5° C., followed by a dropwise addition of 1-piperidinecarbonyl chloride (74.73 µl; 0.60 mmol; 1.00 eq.). The reaction mixture was stirred at 5° C. for 45 min. The reaction mixture was partitioned between water (5 mL) and ethyl acetate (10 mL). The aqueous layer was extracted with ethyl acetate. The combined organic layers were washed with a saturated solution of sodium bicarbonate, with brine, dried over magnesium sulfate, concentrated and purified over gel chromatography. Methyl 3-((4-((2-methylquinolin-4-yl)methoxy)phenyl)sulfonamido)-1-(piperidine-1-carbonyl)azetidine-3-carboxylate (240.00 mg; 72.69%) was isolated as a white solid.

The examples shown in the following table were all synthesized using a similar protocol as Example 16a starting from the corresponding acyl chlorides.

| Example number/Name | Structure | NMR | MS(ES+) m/z |
|---|---|---|---|
| Example 16b: N-hydroxy-3-((4-((2-methylquinolin-4-yl)methoxy)phenyl)sulfonamido)-1-(morpholine-4-carbonyl)azetidine-3-carboxamide | 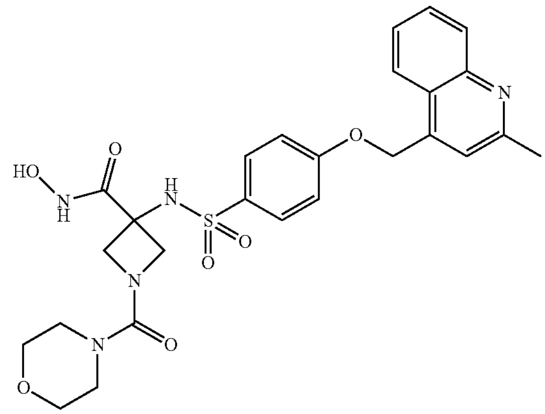 | ¹H NMR (300 MHz, DMSO-d₆): δ 2.67 (s, 3 H), 3.07 (t, J = 4.6 Hz, 4 H), 3.45 (t, J = 4.6 Hz, 4 H), 3.81 (d, J = 9.0 Hz, 2 H), 4.08 (d, J = 9.0 Hz, 2 H), 5.71 (s, 2 H), 7.33 (d, J = 8.6 Hz, 2 H), 7.56-7.61 (m, 2 H), 7.74-7.80 (m, 3 H), 7.98 (d, J = 8.3 Hz, 1 H), 8.10 (d, J = 8.3 Hz, 1 H), 8.51 (s, 1 H), 8.90 (s, 1 H), 10.67 (s, 1 H). | 556 |
| Example 16c: N-hydroxy-1-(4-methylpiperazine-1-carbonyl)-3-((4-((2-methylquinolin-4-yl)methoxy)phenyl)sulfonamido)azetidine-3-carboxamide | 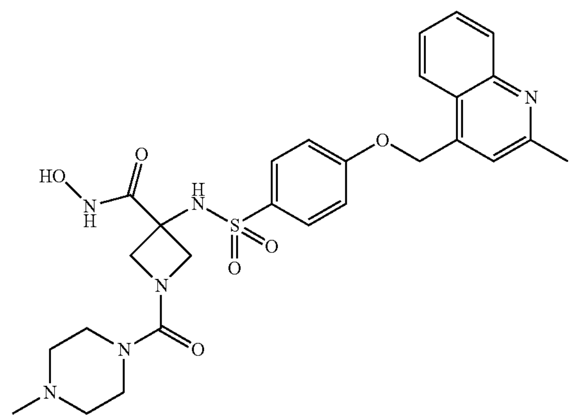 | 1H NMR (400 MHz, DMSO-d6) δ: 10.68 (s, 1H), 8.91 (s, 1H), 8.51 (s, 1H), 8.11-8.13 (d, J = 8.2 Hz, 1H), 7.98-8.00 (d, J = 8.4 Hz, 1H), 7.75-7.80 (m, 3H), 7.59-7.63 (t, J = 7.3 Hz, 1H), 7.58 (s, 1H), 7.33-7.35 (d, J = 8.7 Hz, 2H), 5.72 (s, 2H), 4.06-4.08 (d, J = 8.9 Hz, 2H), 3.78-3.80 (d, J = 8.8 Hz, 1H), 3.10 (s, 4H), 2.68 (s, 3H), 2.24 (m, 4H), 2.17 (s, 3H). | 569 |

Example 17

Allyl 3-(hydroxycarbamoyl)-3-((4-((2-methylquinolin-4-yl)methoxy)phenyl) sulfonamido)azetidine-1-carboxylate Example 17 was synthesized using the same protocol as Example 7a starting from 1-allyl 3-methyl 3-((4-((2-methylquinolin-4-yl)methoxy)phenyl)sulfonamido)azetidine-1,3-dicarboxylate.

1H NMR (400 MHz, DMSO-d₆): δ (ppm) 10.75 (s, 1H), 8.93 (s, 1H), 8.58 (s, 1H), 8.12 (d, J=8.1 Hz, 1H), 7.99 (d, J=8.5 Hz, 1H), 7.85-7.70 (m, 3H), 7.67-7.52 (m, 2H), 7.35 (d, J=9.0 Hz, 2H), 5.85 (m, 1H), 5.74 (s, 2H), 5.28-5.08 (m, 2H), 4.45 (d, J=5.1 Hz, 2H), 4.10 (s, 2H), 3.84 (s, 2H), 2.68 (s, 3H).

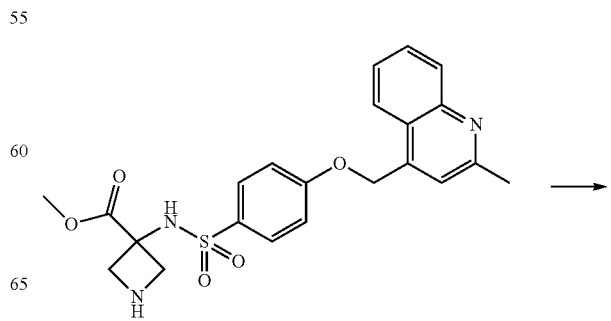

-continued

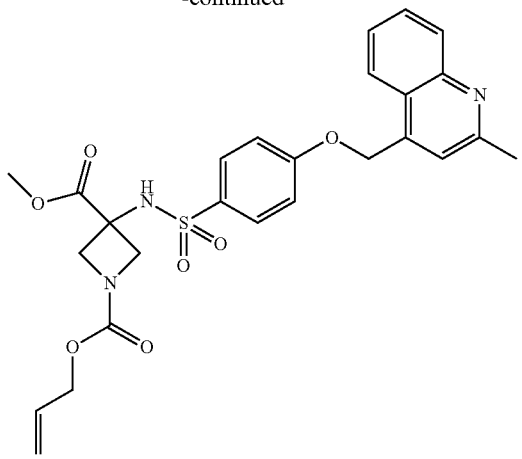

Triethylamine (0.41 ml; 2.99 mmol; 4.00 eq.) was added dropwise to a cooled-down solution of Intermediate E (500.00 mg; 0.75 mmol; 1.00 eq.) in tetrahydrofuran (7.00 ml), directly followed by allyl chloroformate (108.01 mg; 0.90 mmol; 1.20 eq.). The reaction mixture was stirred at 0° C. for 1 hour. The reaction mixture was partitioned between water and ethyl acetate. The aqueous layer was extracted with ethyl acetate. The combined organic layers were washed with a saturated solution of sodium bicarbonate, with brine, dried over magnesium sulfate, concentrated and purified over gel chromatography. 1-allyl 3-methyl 3-((4-((2-methylquinolin-4-yl)methoxy)phenyl)sulfonamido)azetidine-1,3-dicarboxylate (270.20 mg; 68.84%) was isolated as a white solid.

Example 18

2-(1-(2-(dimethylamino)-2-methyl propanoyl)-3-((4-((2-methylquinolin-4-yl)methoxy)phenyl)sulfonamido)azetidin-3-yl)-N-hydroxyacetamide

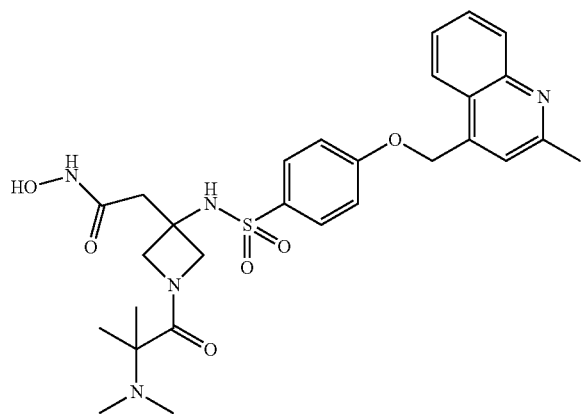 [SMILES: Cc1cc(COc2ccc(S(=O)(=O)NC3(CC(=O)NO)CN(C(=O)C(C)(C)N(C)C)C3)cc2)c2ccccc2n1]

Example 18 was synthesized using the same protocol as Example 7a starting from methyl 2-(1-(2-(dimethylamino)-2-methylpropanoyl)-3-((4-((2-methylquinolin-4-yl)methoxy)phenyl)sulfonamido)azetidin-3-yl)acetate.

1H NMR (400 MHz, DMSO-d$_6$): δ (ppm) 0.85 (s, 3H), 0.96 (s, 3H), 1.94 (s, 6H), 2.54 (s, 2H), 2.67 (s, 3H), 3.75-3.85 (q, J=18.4-10.3 Hz, 2H), 4.22-4.29 (q, J=10.8-4.8 Hz, 1H), 5.71 (s, 2H), 7.31-7.34 (d, J=8.8 Hz, 2H), 7.57 (s, 1H), 7.60-7.61 (d, J=7.3 Hz, 1H), 7.74-7.78 (t, J=7.1 Hz, 1H), 7.80-7.82 (d, J=8.8 Hz, 2H), 7.97-7.99 (d, J=8.4 Hz, 1H), 8.10-8.12 (d, J=8.3 Hz, 1H), 8.23 (s, 1H), 8.79 (s, 1H), 10.49 (s, 1H).

MS(ES+) m/z 570 (MH+)

Methyl 2-(1-(2-(dimethylamino)-2-methylpropanoyl)-3-((4-((2-methylquinolin-4-yl)methoxy)phenyl)sulfonamido) azetidin-3-yl)acetate was synthesized using the same protocol described for Example 12 starting from Intermediate B and 2-Dimethylamino-2-methyl-propionic acid.

Example 19a

N-hydroxy-1-isobutyryl-3-((N-methyl-4-((2-methylquinolin-4-yl)methoxy)phenyl) sulfonamido)azetidine-3-carboxamide

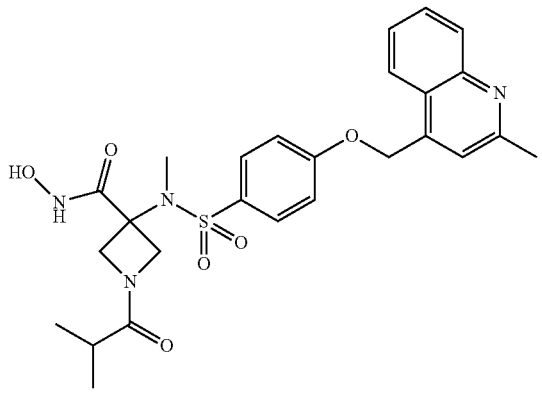

Example 19a was synthesized using the same protocol as Example 7a starting from methyl 1-isobutyryl-3-((N-methyl-4-((2-methylquinolin-4-yl)methoxy)phenyl)sulfonamido)azetidine-3-carboxylate.

$^1$H NMR (400 MHz, DMSO-d$_6$) δ: 0.97 (dd, J=12.4, 6.8 Hz, 6H), 2.45 (q, J=6.8 Hz, 1H), 2.68 (s, 3H), 3.18 (s, 3H), 3.35-3.50 (m, 4H), 4.05-4.21 (m, 2H), 4.46 (s, 2H), 5.74 (s, 2H), 7.26-7.41 (m, 2H), 7.53-7.67 (m, 2H), 7.70-7.87 (m, 3H), 7.99 (dd, J=8.5, 1.2 Hz, 1H), 8.12 (dd, J=8.4, 1.3 Hz, 1H), 9.09 (s, 1H), 10.77 (s, 1H)

MS(ES+) m/z 527 (MH+)

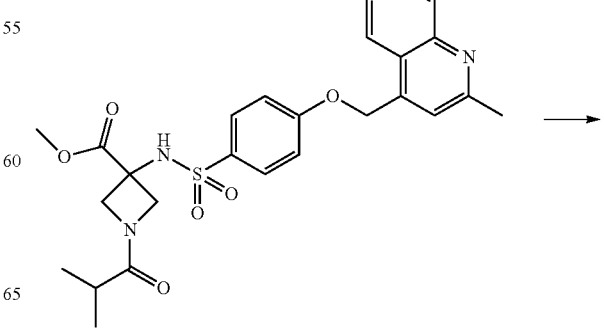

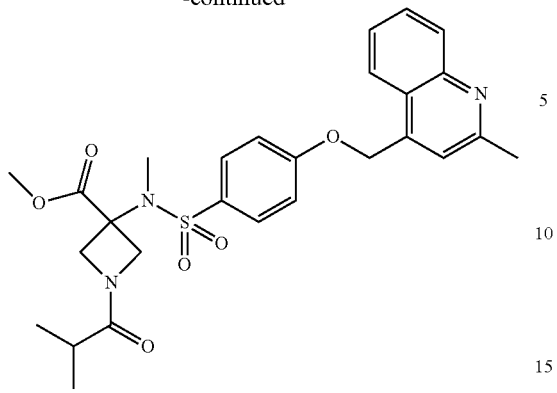
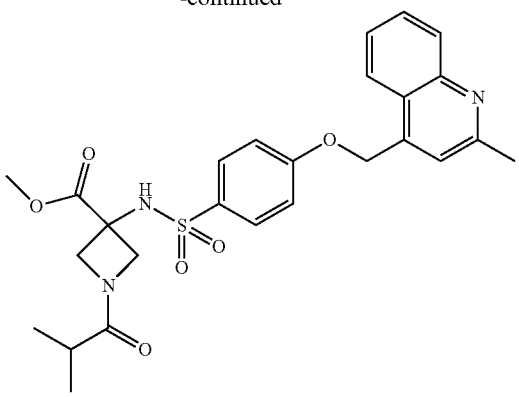

Dimethyl sulfate (0.21 ml; 2.21 mmol; 1.30 eq.) was added dropwise to a solution of 1-Isobutyryl-3-[4-(2-methyl-quinolin-4-ylmethoxy)-benzenesulfonylamino]-azetidine-3-carboxylic acid methyl ester (0.87 g; 1.70 mmol; 1.00 eq.) in N,N-dimethylformamide (10.44 ml) at room temperature, followed by a portion wise addition of potassium carbonate (0.31 g; 2.21 mmol; 1.30 eq.). The reaction mixture was stirred at room temperature for 2 hours. The reaction mixture was partitioned in water (15 mL) and ethyl acetate (100 mL). The organic layer was washed with a saturated solution of sodium bicarbonate, with brine, dried over magnesium sulfate, concentrated.

1-Isobutyryl-3-{methyl-[4-(2-methyl-quinolin-4-yl-methoxy)-benzenesulfonyl]-amino}-azetidine-3-carboxylic acid methyl ester (0.85 g; 95.09%) was isolated as a pale green foam.

Triethylamine (1.24 ml; 8.96 mmol; 4.00 eq.) was added dropwise to a cooled-down suspension of Intermediate E (1 500.00 mg; 2.24 mmol; 1.00 eq.) in tetrahydrofuran (22.50 ml) at 5° C., followed by dropwise addition of isobutyryl chloride (0.24 ml; 2.24 mmol; 1.00 eq.). The reaction mixture was stirred at 5° C. for 15 minutes. The reaction mixture was stirred at room temperature for 2 hours. The reaction mixture was partitioned in water (15 mL) and ethyl acetate (100 mL). The organic layer was washed with a saturated solution of sodium bicarbonate, with brine, dried over magnesium sulfate, concentrated and purified using gel chromatography. 1-Isobutyryl-3-[4-(2-methyl-quinolin-4-ylmethoxy)-benzenesulfonylamino]-azetidine-3-carboxylic acid methyl ester (870.00 mg; 75.91%) was isolated as a white solid.

The examples shown in the following table were all synthesized using a similar protocol as Example 19a starting from the corresponding acyl chlorides.

| Example number/Name | Structure | NMR | MS(ES+) m/z |
|---|---|---|---|
| Example 19b: 1-(2-ethylbutanoyl)-N-hydroxy-3-((N-methyl-4-((2-methylquinolin-4-yl)methoxy)phenyl)sulfonamido)azetidine-3-carboxamide | 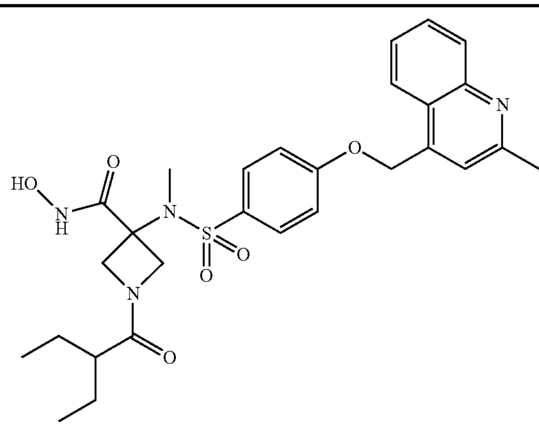 | $^1$H NMR (300 MHz, DMSO-$d_6$) δ 0.72 (t, J = 7.4 Hz, 3 H), 0.78 (t, J = 7.4 Hz, 3 H), 11.27-1.46 (m, 4 H), 2.00-2.09 (m, 1 H), 2.67 (s, 3 H), 2.83 (s, 3 H), 4.08-4.16 (m, 2 H), 4.37 (d, J = 9.7 Hz, 1 H), 4.48 (d, J = 9.7 Hz, 1 H), 5.72 (s, 2 H), 7.32 (d, J = 8.9 Hz, 2 H), 7.57-7.62 (m, 2 H), 7.72-7.80 (m, 3 H), 7.98 (d, J = 8.4 Hz, 1 H), 8.11 (d, J = 8.4 Hz, 1 H), 9.05 (brs, 1H), 10.63 (brs, 1H). | 555 |

| Example number/ Name | Structure | NMR | MS(ES+) m/z |
|---|---|---|---|
| Example 19c: N-hydroxy-3-((N-methyl-4-((2-methylquinolin-4-yl)methoxy)phenyl)sulfonamido)-1-(tetrahydro-2H-pyran-4-carbonyl)azetidine-3-carboxamide | 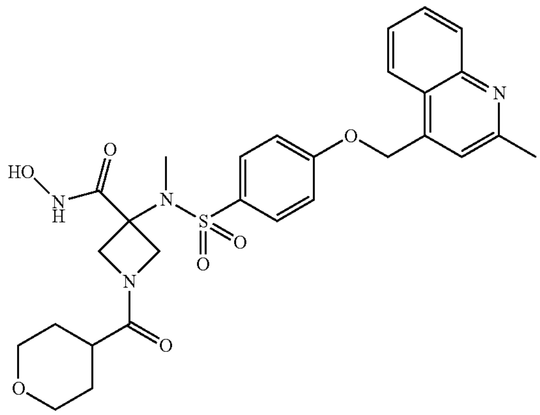 [SMILES: Cc1cc(COc2ccc(S(=O)(=O)N(C)C3(C(=O)NO)CN(C(=O)C4CCOCC4)C3)cc2)c2ccccc2n1] | ¹H NMR (400 MHz, DMSO-d₆) δ 1.42-1.61 (m, 4H), 2.42-2.49 (m, 1H), 2.68 (s, 3H), 2.82 (s, 3H), 3.3-3.4 (m, 2H), 3.83 (dd, J = 9.8, 5.7 Hz, 2H), 4.01-4.20 (m, 2H), 4.44-4.60 (m, 2H), 5.73 (s, 2H), 7.25-7.40 (m, 2H), 7.54-7.65 (m, 2H), 7.72-7.89 (m, 3H), 7.99 (dd, J = 8.5, 1.2 Hz, 1H), 8.12 (dd, J = 8.3, 1.3 Hz, 1H), 9.08 (s, 1H), 10.97 (s, 1H). | 569 |
| Example 19d: N-hydroxy-3-((N-methyl-4-((2-methylquinolin-4-yl)methoxy)phenyl)sulfonamido)-1-(3-methylbutanoyl)azetidine-3-carboxamide | 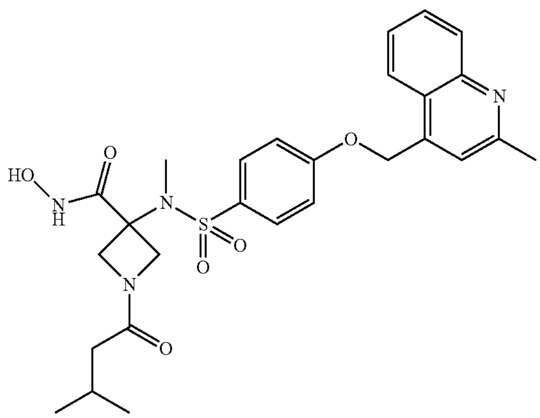 [SMILES: Cc1cc(COc2ccc(S(=O)(=O)N(C)C3(C(=O)NO)CN(C(=O)CC(C)C)C3)cc2)c2ccccc2n1] | ¹H NMR (400 MHz, DMSO-d₆) δ: 0.77-1.04 (m, 6H), 1.93 (t, J = 3.3 Hz, 3H), 2.68 (s, 3H), 2.82 (s, 3H), 3.94-4.20 (m, 2H), 4.40 (s, 2H), 5.73 (s, 2H), 7.24-7.44 (m, 2H), 7.54-7.68 (m, 2H), 7.73-7.87 (m, 3H), 7.99 (dd, J = 8.5, 1.2 Hz, 1H), 8.12 (dd, J = 8.3, 1.3 Hz, 1H), 9.06 (s, 1H), 10.94 (s, 1H) | 541 |

Example 20

Tert-butyl 3-(hydroxycarbamoyl)-3-((N-methyl-4-((2-methylquinolin-4-yl)methoxy) phenyl)sulfonamido)azetidine-1-carboxylate

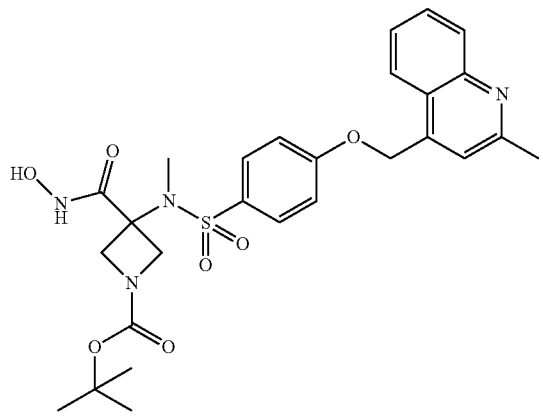 [SMILES: Cc1cc(COc2ccc(S(=O)(=O)N(C)C3(C(=O)NO)CN(C(=O)OC(C)(C)C)C3)cc2)c2ccccc2n1]

Example 20 was synthesized using the same protocol as Example 7a starting from Intermediate D.

¹HNMR (400 MHz, DMSO-d₆): 1.36 (s, 9H), 2.66 (s, 3H), 2.79 (s, 3H), 4.10 (m, 4H), 5.71 (s, 2H), 7.32 (d, 2H, J=9.0 Hz), 7.53-7.66 (m, 2H), 7.70-7.84 (m, 3H), 7.98 (d, 1H, J=7.7 Hz), 8.11 (d, 1H, J=7.4 Hz), 9.04 (s, 1H), 10.93 (s, 1H)

MS(ES+) m/z 557 (MH+)

Example 21a 3-((N-ethyl-4-((2-methylquinolin-4-yl)methoxy) phenyl)sulfonamido)-N-hydroxy-1-isobutyrylazetidine-3-carboxamide

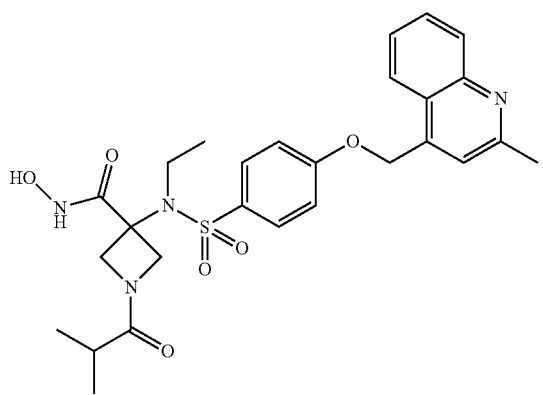 [SMILES: CCN(C1(C(=O)NO)CN(C(=O)C(C)C)C1)S(=O)(=O)c1ccc(OCc2cc(C)nc3ccccc23)cc1]

Example 21a was synthesized using the same protocol as Example 19a starting from diethyl sulfate.

¹H NMR (400 MHz, DMSO) δ 0.97 (dd, J=11.0, 6.7 Hz, 6H), 1.11 (t, J=7.0 Hz, 3H), 2.42-2.49 (m, 2H), 2.68 (s, 3H), 4.11 (s, 2H), 4.40 (d, J=9.6 Hz, 1H), 4.54 (d, J=9.7 Hz, 1H), 5.74 (s, 2H), 7.33 (d, J=8.7 Hz, 2H), 7.54-7.67 (m, 2H), 7.72-7.87 (m, 3H), 7.99 (d, J=8.2 Hz, 1H), 8.12 (d, J=8.3 Hz, 1H).

MS(ES+) m/z 541 (MH+)

Example 21b shown in the following table was synthesized using a similar protocol as Example 21a.

| Example number/ Name | Structure | NMR | MS(ES+) m/z |
|---|---|---|---|
| Example 21b: 3-((N-ethyl-4-((2-methylquinolin-4-yl)methoxy)phenyl)sulfonamido)-N-hydroxy-1-(tetrahydro-2H-pyran-4-carbonyl)azetidine-3-carboxamide | 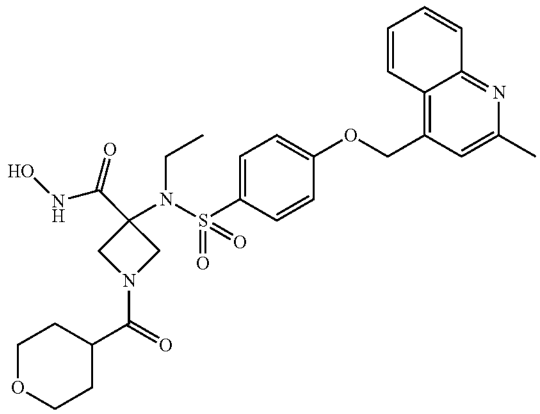 [SMILES: CCN(C1(C(=O)NO)CN(C(=O)C2CCOCC2)C1)S(=O)(=O)c1ccc(OCc2cc(C)nc3ccccc23)cc1] | ¹H NMR (400 MHz, DMSO-d₆) δ 1.10 (s, 3H), 1.55 (s, 4H), 2.45-2.5 (m, 1H), 2.67 (s, 3H), 3.25-3.37 (m, 4H), 3.84 (s, 2H), 4.11 (s, 2H), 4.46 (s, 1H), 4.57 (s, 1H), 5.73 (s, 2H), 7.33 (s, 2H), 7.61 (s, 2H), 7.82 (s, 3H), 7.98 (s, 1H), 8.12 (s, 1H), 9.07 (s, 1H), 10.84 (s, 1H). | 583 |

Example 22

N-hydroxy-1-isobutyryl-3-((N-(2-methoxyethyl)-4-((2-methylquinolin-4-yl)methoxy)phenyl)sulfonamido)azetidine-3-carboxamide

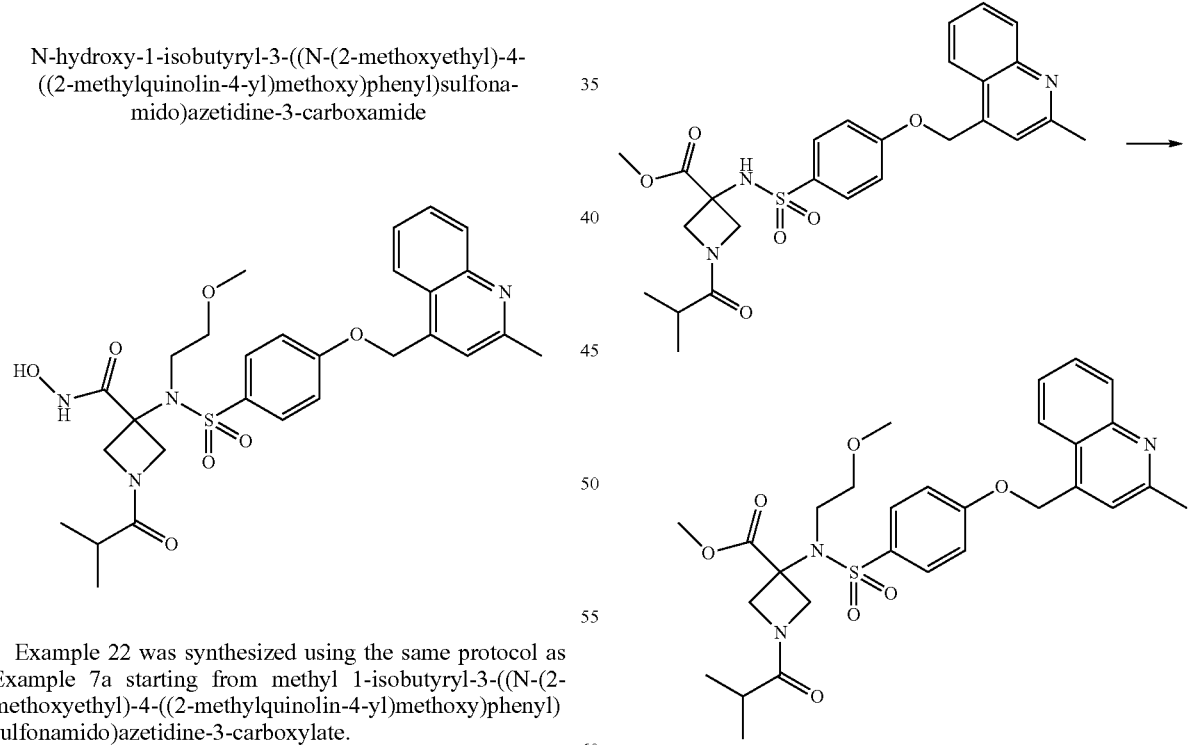

Example 22 was synthesized using the same protocol as Example 7a starting from methyl 1-isobutyryl-3-((N-(2-methoxyethyl)-4-((2-methylquinolin-4-yl)methoxy)phenyl)sulfonamido)azetidine-3-carboxylate.

¹H NMR (400 MHz, DMSO-d₆) δ: 0.97 (dd, J=12.4, 6.8 Hz, 6H), 2.45 (q, J=6.8 Hz, 1H), 2.68 (s, 3H), 3.18 (s, 3H), 3.35-3.50 (m, 4H), 4.05-4.21 (m, 2H), 4.46 (s, 2H), 5.74 (s, 2H), 7.26-7.41 (m, 2H), 7.53-7.67 (m, 2H), 7.70-7.87 (m, 3H), 7.99 (dd, J=8.5, 1.2 Hz, 1H), 8.12 (dd, J=8.4, 1.3 Hz, 1H), 9.09 (s, 1H), 10.77 (s, 1H)

MS(ES−) m/z 569 (MH−)

Potassium carbonate (357.80 mg; 2.59 mmol; 1.50 eq.) was added portion wise to a suspension of 1-Isobutyryl-3-[4-(2-methyl-quinolin-4-ylmethoxy)-benzenesulfonylamino]-azetidine-3-carboxylic acid methyl ester (883.00 mg; 1.73 mmol; 1.00 eq.) in N,N-dimethylformamide (4.42 ml) at room temperature, followed by addition of 2-bromoethyl methyl ether (243.81 µl; 2.59 mmol; 1.50 eq.) and potassium iodide (429.77 mg; 2.59 mmol; 1.50 eq.). The reaction mixture was stirred 24 hours at 50° C. and 24 hours at room temperature. The reaction mixture was partitioned in water (15 mL) and ethyl acetate (100 mL). The organic layer was washed with a saturated solution of sodium bicarbonate, with brine, dried over magnesium sulfate, concentrated and purified by silica gel chromatography. 1-Isobutyryl-3-{(2-methoxy-ethyl)-[4-(2-methyl-quinolin-4-ylmethoxy)-benzenesulfonyl]-amino}-azetidine-3-carboxylic acid methyl ester, (997.00 mg; 101.40%) was isolated as a white solid.

Example 23

N-hydroxy-1-isobutyryl-3-((N-isopropyl-4-((2-methylquinolin-4-yl)methoxy)phenyl) sulfonamido)azetidine-3-carboxamide

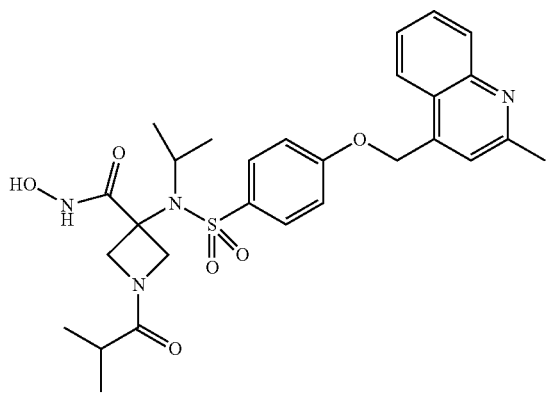 [SMILES: Cc1cc(COc2ccc(S(=O)(=O)N(C(C)C)C3(C(=O)NO)CN(C(=O)C(C)C)C3)cc2)c2ccccc2n1]

Example 23 was synthesized using the same protocol as Example 7a starting from methyl 1-isobutyryl-3-((N-isopropyl-4-((2-methylquinolin-4-yl)methoxy)phenyl) sulfonamido)azetidine-3-carboxylate.

$^1$H NMR (400 MHz, DMSO-d$_6$) δ 0.96 (d, J=, 6.6 Hz, 6H), 1.25 (d, J=6.8 Hz, 6H), 2.47 (m, 1H), 2.68 (s, 2H), 3.73 (p, J=6.9 Hz, 1H), 4.02-4.32 (m, 2H), 4.36-4.65 (m, 2H), 5.74 (d, J=1.0 Hz, 2H), 7.16-7.54 (m, 2H), 7.45-7.66 (m, 2H), 7.66-7.79 (m, 1H), 7.77-7.93 (m, 2H), 7.99 (dd, J=8.6, 1.2 Hz, 1H), 8.11 (d, J=8.6 Hz, 1H), 9.16 (s, 1H), 10.70 (s, 1H).

MS(ES+) m/z 555 (MH+)

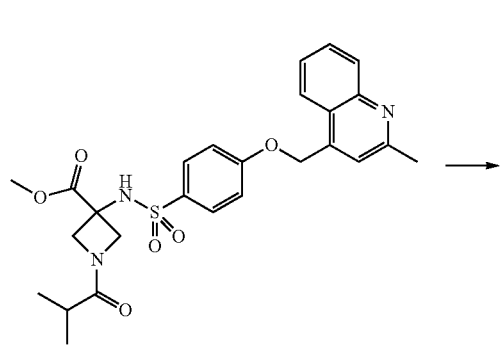

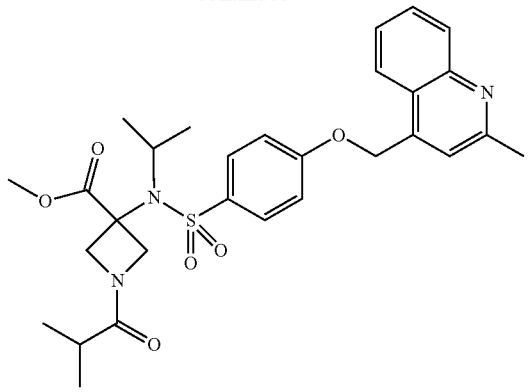

Di-tert-butyl azodicarboxylate (0.27 g; 1.17 mmol; 3.00 eq.) was added to a cooled-down solution of isopropanol (66.91 µl; 0.88 mmol; 3.00 eq.), triphenylphosphine (0.23 g; 0.88 mmol; 3.00 eq.) in dichloromethane (1.50 ml) at −5° C. The reaction mixture was stirred at −5° C. for 5 minutes. 1-Isobutyryl-3-[4-(2-methyl-quinolin-4-ylmethoxy)-benzenesulfonylamino]-azetidine-3-carboxylic acid methyl ester (150.00 mg; 0.29 mmol; 1.00 eq.) was added portion wise to the reaction mixture. The reaction mixture was stirred at room temperature for 24 hours.

Isopropanol (66.91 µl; 0.88 mmol; 3.00 eq.), triphenylphosphine (0.23 g; 0.88 mmol; 3.00 eq.) and di-tert-butyl azodicarboxylate (0.27 g; 1.17 mmol; 3.00 eq.) were added to the mixture which was stirred at room temperature for another 24 hours. Isopropanol (66.91 µl; 0.88 mmol; 3.00 eq.), triphenylphosphine (0.23 g; 0.88 mmol; 3.00 eq.) and di-tert-butyl azodicarboxylate (0.27 g; 1.17 mmol; 3.00 eq.) were added once again to the mixture which was stirred at room temperature for another 48 hours.

The reaction mixture was partitioned in water (15 mL) and ethyl acetate (100 mL). The organic layer was washed with a saturated solution of sodium bicarbonate, with brine, dried over magnesium sulfate, concentrated and purified by silica gel chromatography. Methyl 1-isobutyryl-3-((N-isopropyl-4-((2-methylquinolin-4-yl)methoxy)phenyl)sulfonamido) azetidine-3-carboxylate (101.00 mg; 46%) was isolated as a clear oil.

Example 24

2-(1-acetyl-3-((4-((2,8-dimethylquinolin-4-yl)methoxy)phenyl)sulfonamido)azetidin-3-yl)-N-hydroxyacetamide

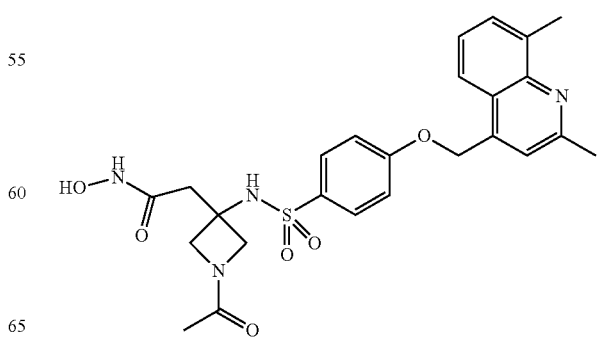

Example 24 was synthesized using the same protocol as Example 1 starting from Intermediate C.

1H NMR (300 MHz, DMSO-d$_6$) δ 1.68 (s, 3H), 2.68 (s, 3H), 2.71 (s, 3H), 2.92 (s, 2H), 3.36 (s, 3H), 3.73 (d, J=9.0 Hz, 1H), 3.81 (d, J=9.0 Hz, 1H), 4.06 (d, J=9.0 Hz, 1H), 4.12 (d, J=9.0 Hz, 1H), 5.70 (s, 2H), 7.31 (d, J=8.8 Hz, 2H), 7.47 (dd, J=8.1, 6.8 Hz, 1H), 7.55 (s, 1H), 7.61 (d, J=6.8 Hz, 1H), 7.74 (d, J=8.8 Hz, 2H), 7.93 (d, J=8.1 Hz, 1H), 8.44 (s, 1H).

MS(ES+) m/z 513 (MH+)

Example 25

N-hydroxy-2-(3-((4-((2-methylquinolin-4-yl)methoxy)phenyl)sulfonamido)-1-(morpholine-4-carbonyl)azetidin-3-yl)acetamide

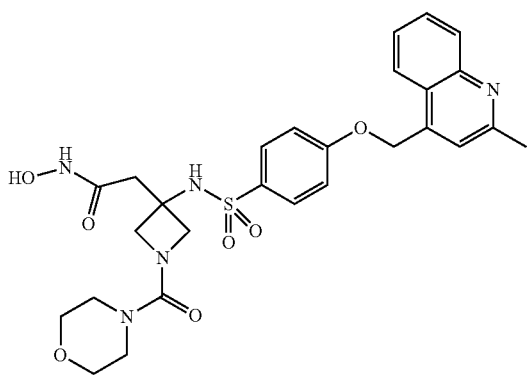 [SMILES: Cc1cc(COc2ccc(S(=O)(=O)NC3(CC(=O)NO)CN(C(=O)N4CCOCC4)C3)cc2)c2ccccc2n1]

Example 25 was synthesized using the same protocol as Example 7a starting from methyl 2-(3-((4-((2-methylquinolin-4-yl)methoxy)phenyl)sulfonamido)-1-(morpholine-4-carbonyl)azetidin-3-yl)acetate.

1H NMR (300 MHz, DMSO-d$_6$): δ(ppm) 2.53 (s, 2H), 2.67 (s, 3H), 3.04 (t, J=4.7 Hz, 4H), 3.44 (t, J=4.6 Hz, 4H), 3.82-3.89 (m, 4H), 5.71 (s, 2H), 7.32 (d, J=8.6 Hz, 2H), 7.56-7.61 (m, 2H), 7.73-7.78 (m, 1H), 7.82 (d, J=8.6 Hz, 2H), 7.98 (d, J=8.4 Hz, 1H), 8.10 (d, J=8.3 Hz, 1H), 8.77 (brs, 1H), 10.4 (brs, 1H).

MS(ES+) m/z 570 (MH+)

Methyl 2-(3-((4-((2-methylquinolin-4-yl)methoxy)phenyl)sulfonamido)-1-(morpholine-4-carbonyl)azetidin-3-yl)acetate was synthesized using the protocol described for Example 9 starting with morpholine-4-carbonyl chloride.

Example 26a

N-hydroxy-1-((1r,3r)-3-methoxycyclobutane-1-carbonyl)-3-((4-((2-methylquinolin-4-yl)methoxy)phenyl)sulfonamido)azetidine-3-carboxamide

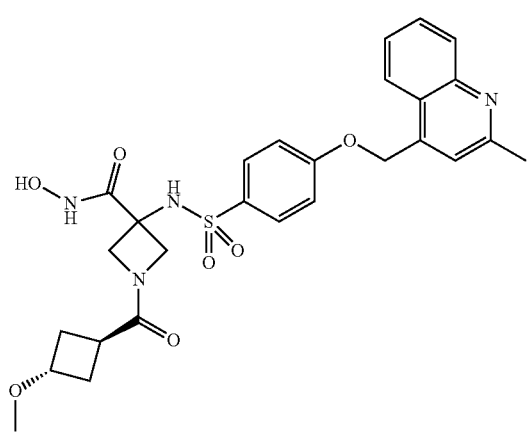 [SMILES: CO[C@H]1C[C@H](C(=O)N2CC(NS(=O)(=O)c3ccc(OCc4cc(C)nc5ccccc45)cc3)(C(=O)NO)C2)C1]

Example 26a was synthesized using the same protocol as Example 7a starting from methyl 1-((1r,3r)-3-methoxycyclobutane-1-carbonyl)-3-((4-((2-methylquinolin-4-yl)methoxy)phenyl)sulfonamido)azetidine-3-carboxylate $^1$H NMR (400 MHz, DMSO-d$_6$): δ (ppm) 1.91-2.02 (m, 2H), 2.12-2.13 (m, 1H), 2.20-2.23 (m, 1H), 2.68 (s, 3H), 2.79-2.84 (m, 1H), 3.07 (s, 3H), 3.77-3.79 (d, J=10.1 Hz, 1H), 3.82-3.88 (q, J=6.4 Hz, 1H), 3.91-3.93 (d, J=9.2 Hz, 1H), 3.99-4.02 (d, J=10.0 Hz, 1H), 4.25-4.27 (d, J=9.2 Hz, 1H), 5.72 (s, 2H), 7.33-7.35 (d, J=8.8 Hz, 2H), 7.57 (s, 1H), 7.58-7.62 (t, J=7.7 Hz, 1H), 7.74-7.79 (t, 3H), 7.98-8.00 (d, J=8.3 Hz, 1H), 8.10-8.12 (d, J=8.2 Hz, 1H)

MS(ES-) m/z 553 (MH-)

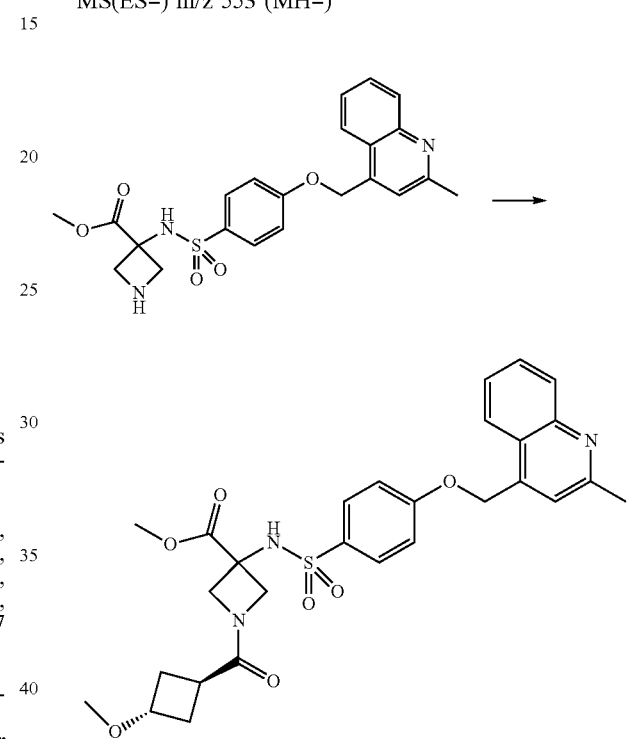

1-Ethyl-3-(3-dimethylaminopropyl)carbodiimide hydrochloride (171.79 mg; 0.90 mmol; 1.20 eq.) was added to a solution of trans-3-methoxycyclobutanecarboxylic acid (116.62 mg; 0.90 mmol; 1.20 eq.) in N,N-dimethylformamide (7.50 ml) at room temperature, followed by 1-Oxypyridin-2-ol (99.56 mg; 0.90 mmol; 1.20 eq.). The reaction mixture was stirred at room temperature for 10 minutes. Intermediate E (500.00 mg; 0.75 mmol; 1.00 eq.) and N,N-diisopropylethylamine (0.51 ml; 2.99 mmol; 4.00 eq.) were added to the mixture. The reaction mixture was stirred at room temperature for 24 hrs.

The reaction mixture was partitioned in water (15 mL) and ethyl acetate (100 mL). The organic layer was washed with a saturated solution of sodium bicarbonate, with brine, dried over magnesium sulfate, concentrated and purified by silica gel chromatography. Methyl 1-((1r,3r)-3-methoxycyclobutane-1-carbonyl)-3-((4-((2-methylquinolin-4-yl)methoxy)phenyl)sulfonamido)azetidine-3-carboxylate ester (178.00 mg; 43.05%) was isolated as a pale yellow solid.

The example shown in the following table was synthesized using a similar protocol as Example 26a starting from the corresponding carboxylic acids.

| Example number/ Name | Structure | NMR | MS |
|---|---|---|---|
| Example 26b: N-hydroxy-1-((1s,3s)-3-methoxycyclobutane-1-carbonyl)-3-((4-((2-methylquinolin-4-yl)methoxy)phenyl)sulfonamido)azetidine-3-carboxamide | 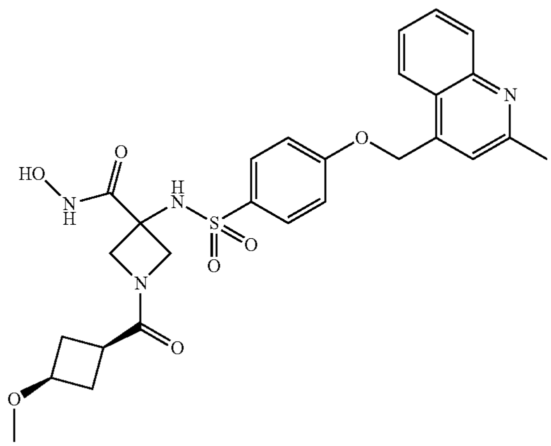 [SMILES: CO[C@H]1C[C@@H](C(=O)N2CC(NS(=O)(=O)c3ccc(OCc4cc(C)nc5ccccc45)cc3)(C(=O)NO)C2)C1] | $^1$H NMR (400 MHz, DMSO-d$_6$): δ (ppm) 1.72-1.87 (m, 2H), 2.17-2.26 (m, 2H), 2.41-2.45 (m, 1H), 2.68 (s, 3H), 3.06 (s, 3H), 3.65-3.72 (q, J = 7.3 Hz, 1H), 3.75-3.78 (d, J = 10.1 Hz, 1H), 3.93-4.00 (q, J = 10.2-7.6 Hz, 2H), 4.29-4.31 (d, J = 9.2 Hz, 1H), 5.72 (s, 2H), 7.33-7.35 (d, J = 8.8 Hz, 2H), 7.57 (s, 1H), 7.58-7.62 (t, J = 7.7 Hz, 1H), 7.74-7.79 (t, 3H), 7.98-8.00 (d, J = 8.3 Hz, 1H), 8.10-8.12 (d, J = 8.2 Hz, 1H) | (ES−) m/z 553 (MH−) |
| Example 26c: 1-(2-cyclopropylacetyl)-N-hydroxy-3-((4-((2-methylquinolin-4-yl)methoxy)phenyl)sulfonamido)azetidine-3-carboxamide | 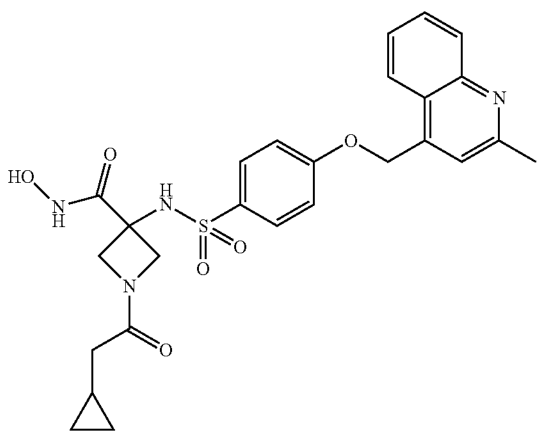 [SMILES: Cc1cc(COc2ccc(S(=O)(=O)NC3(C(=O)NO)CN(C(=O)CC4CC4)C3)cc2)c2ccccc2n1] | $^1$H NMR (400 MHz, DMSO) δ −0.00 (td, J = 4.9, 1.8 Hz, 2H), 0.35 (dd, J = 8.2, 1.5 Hz, 2H), 0.70-0.85 (m, 1H), 1.86 (dt, J = 6.8, 3.4 Hz, 2H), 2.65 (s, 3H), 3.73 (d, J = 10.2 Hz, 1H), 3.97 (d, J = 9.7 Hz, 2H), 4.30 (d, J = 9.1 Hz, 1H), 5.69 (s, 2H), 7.23-7.35 (m, 2H), 7.49-7.61 (m, 2H), 7.69-7.80 (m, 3H), 7.96 (dd, J = 8.5, 1.2 Hz, 1H), 8.08 (dd, J = 8.5, 1.3 Hz, 1H). | (ES+) m/z 525 (MH+) |
| Example 26d: (S)-N-hydroxy-1-(2-methylbutanoyl)-3-((4-((2-methylquinolin-4-yl)methoxy)phenyl)sulfonamido)azetidine-3-carboxamide | 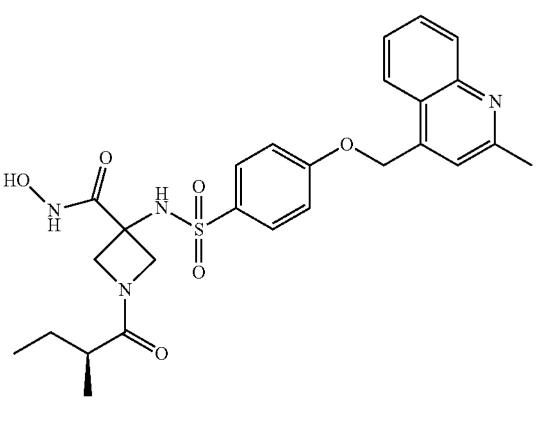 [SMILES: CC[C@H](C)C(=O)N1CC(NS(=O)(=O)c2ccc(OCc3cc(C)nc4ccccc34)cc2)(C(=O)NO)C1] | $^1$H NMR (400 MHz, DMSO-d$_6$) δ: 0.60-0.95 (m, 6H), 1.11-1.27 (m, 1H), 1.29-1.47 (m, 1H), 2.09 (p, J = 6.8 Hz, 1H), 2.68 (s, 3H), 3.78 (t, J = 10.3 Hz, 1H), 4.00 (q, J = 11.1, 10.1 Hz, 2H), 4.39 (d, J = 9.1 Hz, 1H), 5.73 (s, 2H), 7.28-7.40 (m, 2H), 7.54-7.65 (m, 2H), 7.73-7.84 (m, 3H), 7.99 (dd, J = 8.5, 1.2 Hz, 1H), 8.11 (dd, J = 8.3, 1.3 Hz, 1H) | (ES+) m/z 527 (MH+) |

| Example number/Name | Structure | NMR | MS |
|---|---|---|---|
| Example 26e:<br>1-(3,3-difluorocyclobutane-1-carbonyl)-N-hydroxy-3-((4-((2-methylquinolin-4-yl)methoxy)phenyl)sulfonamido)azetidine-3-carboxamide | | ¹H NMR (400 MHz, DMSO-d₆) δ: 10.75 (s, 1H), 8.95 (s, 1H), 8.57 (s, 1H), 8.10-8.12 (d, J = 7.8 Hz, 1H), 7.98-8.00 (d, J = 8.5 Hz, 1H), 7.74-7.80 (m, 3H), 7.58-7.62 (td, J = 7.0-1.2 Hz, 1H), 7.57 (s, 1H), 7.33-7.35 (d, J = 9.0 Hz, 2H), 5.72 (s, 2H), 4.35-4.37 (d, J = 9.4 Hz, 1H), 4.01-4.07 (m, 2H), 3.78-3.80 (d, J = 10.2 Hz, 1H), 2.82-2.89 (m, 1H), 2.68 (s, 3H), 2.55-2.73 (m, 4H). | (ES+) m/z 561 (MH+) |
| Example 26f:<br>1-(2-cyclobutylacetyl)-N-hydroxy-3-((4-((2-methylquinolin-4-yl)methoxy)phenyl)sulfonamido)azetidine-3-carboxamide | | ¹H NMR (400 MHz, DMSO-d₆): δ (ppm) 10.72 (s, 1H), 8.93 (s, 1H), 8.55 (s, 1H), 8.10-8.12 (d, J = 7.8 Hz, 1H), 7.98-7.99 (d, J = 7.8 Hz, 1H), 7.78-7.80 (d, J = 8.0 Hz, 2H), 7.74-7.77 (m, 1H), 7.58-7.62 (td, J = 7.0-1.2 Hz, 1H), 7.57 (s, 1H), 5.72 (s, 2H), 4.34-4.36 (d, J = 9.0 Hz, 1H), 3.96-4.01 (t, J = 10.7 Hz, 2H), 3.72-3.75 (d, J = 10.0 Hz, 1H), 2.68 (s, 3H), 2.40-2.45 (m, 1H), 2.03-2.06 (m, 2H), 1.91-1.98 (m, 2H), 1.71-1.77 (m, 2H), 1.51-1.61 (m, 2H) | (ES−) m/z 537 (MH−) |

Example 27
3-((4-((2,8-dimethylquinolin-4-yl)methoxy)phenyl)sulfonamido)-N-hydroxy-1-isobutyrylazetidine-3-carboxamide

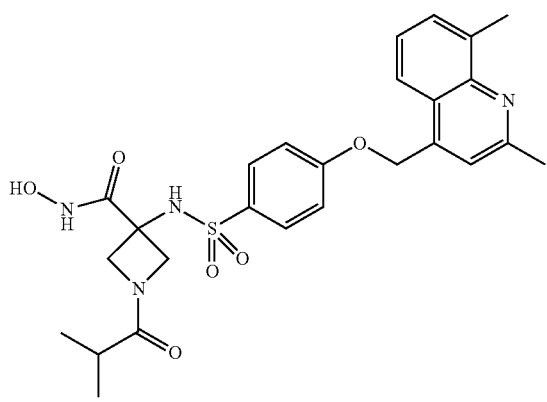 [SMILES: Cc1cc(COc2ccc(S(=O)(=O)NC3(C(=O)NO)CN(C(=O)C(C)C)C3)cc2)c2cccc(C)c2n1]

Example 27 was synthesized using the same protocol as Example 7a starting from Intermediate F.

%). ¹H NMR (300 MHz, DMSO-d₆) δ 0.82 (d, J=6.9 Hz, 3H), 0.88 (d, J=6.9 Hz, 3H), 2.23-2.35 (m, 1H), 2.68 (s, 3H), 2.71 (s, 3H), 3.75 (d, J=10.4 Hz, 1H), 3.97 (d, J=10.4 Hz, 1H), 4.01 (d, J=9.2 Hz, 1H), 4.38 (d, J=9.2 Hz, 1H), 5.69 (s, 2H), 7.32 (d, J=8.8 Hz, 2H), 7.47 (dd, J=8.5, 7.3 Hz, 1H), 7.56 (s, 1H), 7.61 (d, J=7.3 Hz, 1H), 7.77 (d, J=8.8 Hz, 2H), 7.93 (d, J=8.5 Hz, 1H), 8.24 (s, 1H), 8.93 (brs, 2H)

MS(ES+) m/z 527 (MH+)

Example 28a

N-hydroxy-2-(1-(4-isopropylpiperazine-1-carbonyl)-3-((4-((2-methylquinolin-4-yl)methoxy)phenyl)sulfonamido)azetidin-3-yl)acetamide

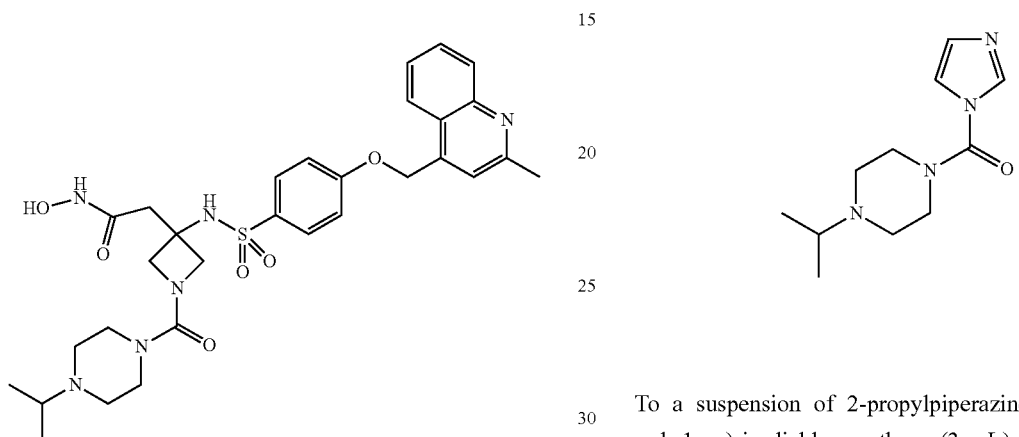

Example 28 was synthesized using the same protocol as Example 25 starting from imidazol-1-yl-(4-isopropylpiperazin-1-yl)methanone.

1H NMR (400 MHz, DMSO-d$_6$): δ (ppm) 10.45 (s, 1H), 8.16 (s, 1H), 8.14 (s, 1H), 8.10-8.12 (d, J=7.6 Hz, 1H), 7.97-7.99 (d, J=7.8 Hz, 1H), 7.82-7.84 (d, J=8.9 Hz, 2H), 7.74-7.78 (td, J=7.0-1.3 Hz, 1H), 7.58-7.62 (td, J=6.9-1.2 Hz, 1H), 7.57 (s, 1H), 7.33-7.36 (d, J=8.9 Hz, 1H), 5.71 (s, 2H), 3.80-3.87 (q, J=8.8 Hz, 4H), 3.00-3.03 (t, J=4.6 Hz, 4H), 2.68 (s, 3H), 2.55-2.60 (m, 1H), 2.53 (s, 2H), 2.26-2.28 (t, J=4.6 Hz, 4H), 0.87-0.88 (d, J=6.5 Hz, 6H)

MS(ES+) m/z 611 (MH+)

To a suspension of 2-propylpiperazine (279 μL, 1.95 mmol, 1 eq) in dichloromethane (3 mL) was added diisopropylethylamine (0,672 ml, 3.9 mmol, 2 eq) then carbonyldiimidazole (348 mg, 2.14 mmol, 1.1 eq). The reaction mixture was stirred at room temperature for 30 min. Solvent was removed under vacuo and the residue was used in the next step without further purification.

Example 28b shown in the following table was synthesized using a similar protocol as Example 28a starting from N-ethyl piperazine.

| Example number/Name | Structure | NMR | MS |
|---|---|---|---|
| Example 28b: 2-(1-(4-ethylpiperazine-1-carbonyl)-3-((4-((2-methylquinolin-4-yl)methoxy)phenyl)sulfonamido)azetidin-3-yl)-N-hydroxyacetamide | 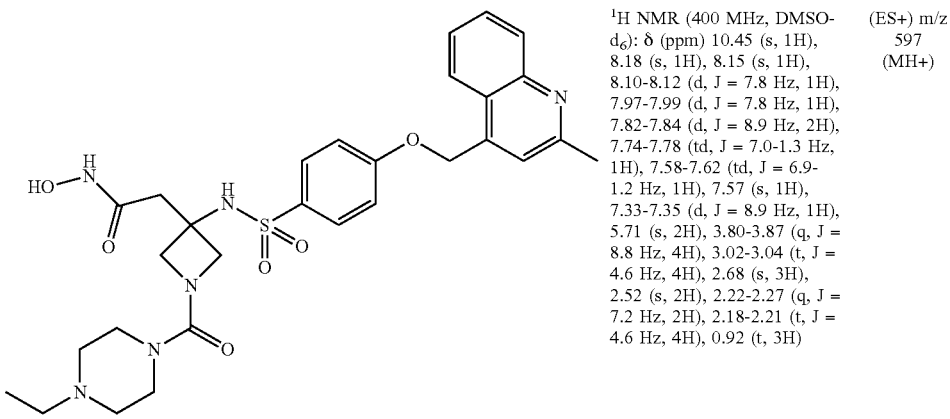 | 1H NMR (400 MHz, DMSO-d$_6$): δ (ppm) 10.45 (s, 1H), 8.18 (s, 1H), 8.15 (s, 1H), 8.10-8.12 (d, J = 7.8 Hz, 1H), 7.97-7.99 (d, J = 7.8 Hz, 1H), 7.82-7.84 (d, J = 8.9 Hz, 2H), 7.74-7.78 (td, J = 7.0-1.3 Hz, 1H), 7.58-7.62 (td, J = 6.9-1.2 Hz, 1H), 7.57 (s, 1H), 7.33-7.35 (d, J = 8.9 Hz, 1H), 5.71 (s, 2H), 3.80-3.87 (q, J = 8.8 Hz, 4H), 3.02-3.04 (t, J = 4.6 Hz, 4H), 2.68 (s, 3H), 2.52 (s, 2H), 2.22-2.27 (q, J = 7.2 Hz, 2H), 2.18-2.21 (t, J = 4.6 Hz, 4H), 0.92 (t, 3H) | (ES+) m/z 597 (MH+) |

Example 29

3-((4-((8-fluoro-2-methylquinolin-4-yl)methoxy)phenyl)sulfonamido)-N-hydroxy-1-(3-methylbutanoyl)azetidine-3-carboxamide

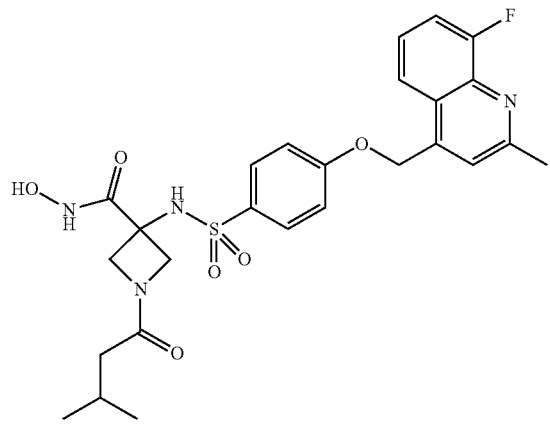 [SMILES: Cc1cc(COc2ccc(S(=O)(=O)NC3(C(=O)NO)CN(C(=O)CC(C)C)C3)cc2)c2cccc(F)c2n1]

Example 29 was synthesized using the same protocol as Example 7a starting from methyl 3-((4-((8-fluoro-2-methylquinolin-4-yl)methoxy)phenyl)sulfonamido)azetidine-3-carboxylate.

$^1$H NMR (400 MHz, DMSO-d$_6$) δ: 0.81 (dd, J=10.7, 6.1 Hz, 6H), 1.82 (tt, J=8.1, 3.9 Hz, 3H), 2.71 (s, 3H), 3.76 (d, J=10.3 Hz, 1H), 4.00 (dd, J=9.5, 5.5 Hz, 2H), 4.34 (d, J=9.1 Hz, 1H), 5.73 (s, 2H), 7.34 (d, J=8.9 Hz, 2H), 7.56-7.64 (m, 2H), 7.67 (s, 1H), 7.79 (d, J=8.9 Hz, 2H), 7.91-7.97 (m, 1H)

MS(ES+) m/z 545 (MH+)

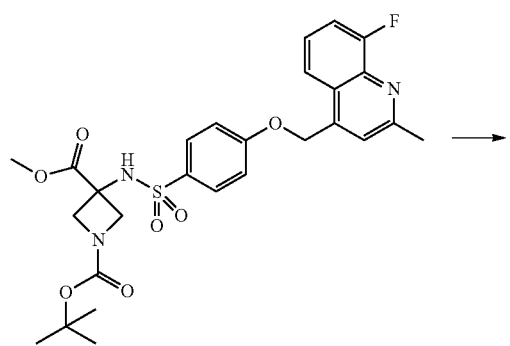

A 4M solution of hydrochloric acid in water (1.39 ml) was added dropwise to a suspension of O1-tert-butyl O3-methyl 3-[[4-[(8-fluoro-2-methyl-4-quinolyl)methoxy]phenyl]sulfonylamino]azetidine-1,3-dicarboxylate (519 mg, 0.93 mmol, 1 eq) in dichloromethane (5 mL). The reaction mixture was stirred at room temperature overnight. The solvent was removed under reduced pressure and the resulted solid was dried under vacuum to give the di hydrochloride salt of methyl 3-((4-((8-fluoro-2-methylquinolin-4-yl)methoxy)phenyl)sulfonamido)azetidine-3-carboxylate (493 mg, 100%) as a white solid (493 mg, 100%).

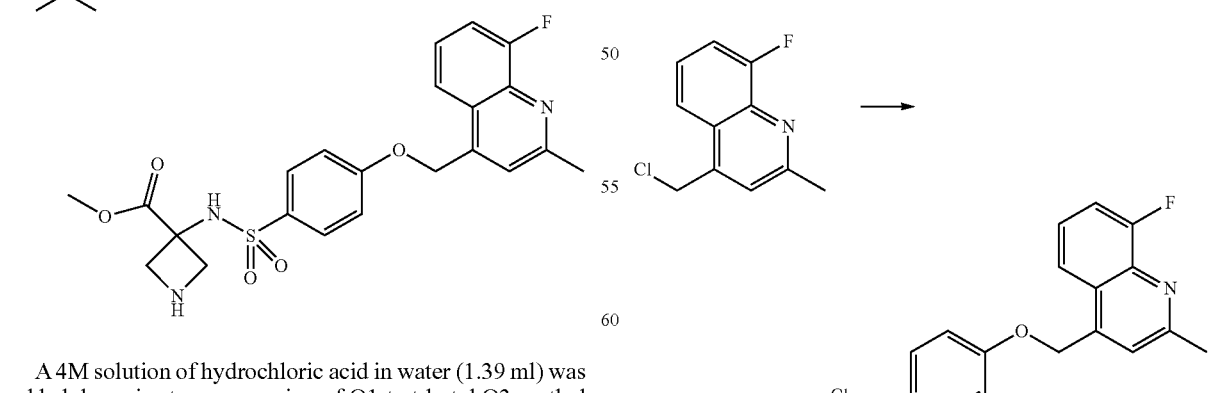

To a solution of O1-tert-butyl O3-methyl 3-aminoazetidine-1,3-dicarboxylate (975 mg, 4.23 mmol, 1 eq) in dichloromethane (9.8 mL) were added triethylamine (1715.07 μl, 12.7 mmol, 3 eq) and 4-[(8-fluoro-2-methyl-4-quinolyl)methoxy]benzenesulfonyl chloride (1954.11 mg, 5.34 mmol, 1.26 eq). The mixture was stirred at room temperature overnight. A sodium bicarbonate saturated solution was added to the reaction, the organic layer was extracted with ethyl acetate, dried over magnesium sulfate, filtered and evaporated. The residue was purified by flash chromatography to give of O1-tert-butyl O3-methyl 3-[[4-[(8-fluoro-2-methyl-4-quinolyl)methoxy]phenyl]sulfonylamino]azetidine-1,3-dicarboxylate (0.95 g, 40%) as a colorless solid.

Sodium 4-hydroxybenzene sulfinate (3.6 g, 18.2 mmole, 0.9 eq) and 4-(chloromethyl)-8-fluoro-2-methylquinoline (5 g, 20.3 mmole, 1 eq) were dissolved in a 1M solution of NaOH in water (60 mL) and isopropanol (35 mL). The reaction mixture was stirred at 80° C. for 3 hours. The i-PrOH was concentrated and aqueous phase was washed with ethyl acetate. The aqueous layer was acidified using a 3M solution of hydrochloric acid in water. Filtration of the precipitate yielded sodium 4-[(2,8-dimethyl-4-quinolyl)methoxy]benzenesulfonate (2.7 g) as an off-white solid.

To a suspension of sodium 4-[(2,8-dimethyl-4-quinolyl)methoxy]benzenesulfonate (2 g, 5.47 mmol, 1 eq) in DMF (0.3 mL) and dichloromethane (10 mL) at 0° C. was added dropwise oxalyl chloride (4.7 mL, 54.7 mmol, 10 eq). The mixture was stirred at room temperature for 1 hr. The resulting suspension was filtered off. The cake was washed with dichloromethane and dried under reduced pressure to give of the hydrochloride salt of 4-[(8-fluoro-2-methyl-4-quinolyl)methoxy]benzenesulfonyl chloride as white solid (1.85 g, 84.9%).

Example 30

3-((4-((8-fluoro-2-methylquinolin-4-yl)methoxy)-N-methylphenyl)sulfonamido)-N-hydroxy-1-isobutyrylazetidine-3-carboxamide

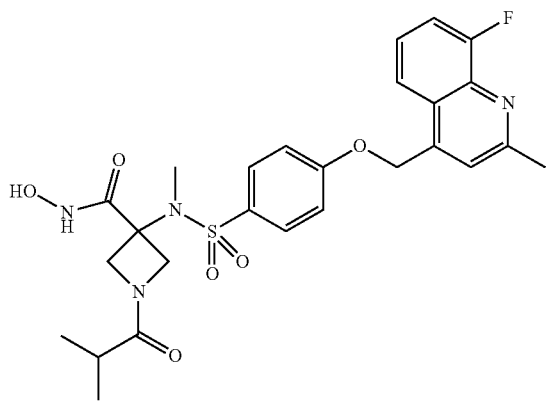 [SMILES: Cc1cc(COc2ccc(S(=O)(=O)N(C)C3(C(=O)NO)CN(C(=O)C(C)C)C3)cc2)c2cccc(F)c2n1]

Example 30 was synthesized using the same protocol as Example 19a starting from methyl 3-((4-((8-fluoro-2-methylquinolin-4-yl)methoxy)phenyl)sulfonamido)azetidine-3-carboxylate.

$^1$H NMR (400 MHz, DMSO-d$_6$) δ: 0.96 (dd, J=14.1, 6.8 Hz, 6H), 2.43 (d, J=6.9 Hz, 1H) 2.83 (s, 3H), 2.72 (s, 3H), 5.73 (d, J=1.0 Hz, 2H), 7.34 (d, J=9.0 Hz, 2H), 7.63-7.54 (m, 2H), 7.69 (s, 1H), 7.86-7.77 (m, 2H), 7.86-7.77 (m, 2H), 7.99-7.91 (m, 1H), 9.07 (s, 1H), 10.96 (s, 1H).

MS(ES+) m/z 545 (MH+)

Example 31

2-(3-((4-((2,8-dimethylquinolin-4-yl)methoxy)phenyl)sulfonamido)-1-(4-methylpiperazine-1-carbonyl)azetidin-3-yl)-N-hydroxyacetamide

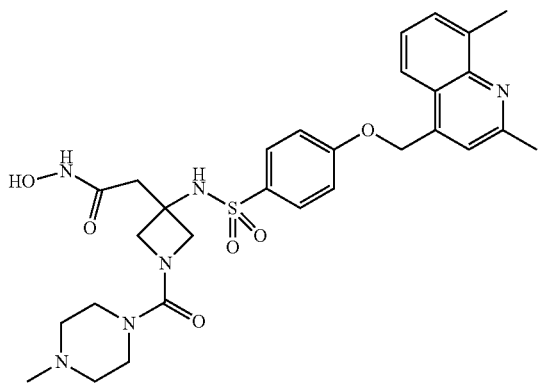

Example 31 was synthesized using the same protocol as Example 25 starting from methyl 2-(3-((4-((2,8-dimethylquinolin-4-yl)methoxy)phenyl)sulfonamido)-1-(4-methylpiperazine-1-carbonyl)azetidin-3-yl)acetate.

$^1$H NMR (400 MHz, DMSO-d$_6$): δ (ppm) 10.45 (s, 1H), 8.17 (s, 1H), 8.14 (s, 1H), 7.93-7.95 (d, J=8.2 Hz, 2H), 7.61-7.63 (d, J=7.0 Hz, 1H), 7.57 (s, 1H), 7.46-7.50 (t, J=8.2 Hz, 1H), 7.31-7.33 (d, J=8.9 Hz, 1H), 5.69 (s, 2H), 3.80-3.87 (q, J=8.8 Hz, 4H), 3.02-3.05 (t, J=4.5 Hz, 4H), 2.72 (s, 3H), 2.69 (s, 3H), 2.53 (s, 2H), 2.15-2.17 (t, J=4.5 Hz, 4H), 2.11 (s, 3H).

MS(ES+) m/z 597 (MH+)

Activity of the compounds was investigated using human peripheral blood mononuclear cells (hPBMC). This assay was designed to measure the inhibition of the TNFα secretion from LPS stimulated frozen Peripheral Blood Mononuclear Cells (PBMC) isolated from human blood. TNFα levels were measured using HTRF® Human TNFα kit (Cisbio #62TNFPEC) which is a rapid and quantitative sandwich immunoassay based on TR-FRET technology.

Frozen PBMC were quickly thawed, resuspended in culture medium (RPMI 10% inactivated FBS) and viable cells were seeded in 96-well plates (50,000 cells/well). Serial dilutions of tested inhibitors (from 10000 nM to 0.04 nM, 0.1% DMSO) and 1 µg/mL of LPS (Lipopolysaccharides from *Escherichia coli*, Sigma # L2630) were added to the cells. After overnight incubation at 37° C., 10 µL of cell supernatant were mixed with 5 µL of each tagged anti-TNFα specific antibody as recommended by the supplier. After 2 hours of incubation at room temperature, the HTRF® signals were measured using a microplate reader (wavelengths: excitation=337 nm, first emission=620 nm, second emission=665 nm). The ratios of the measured signals (665/620) were normalized using the average of positive controls (LPS-activated PBMC with no inhibitor) and negative controls (not activated PBMC). IC50 were calculated using a four-parameters logistic model.

Activity of the compounds was investigated using TACE (ADAM17) isolated enzyme. The screening of ADAM17 inhibitors was performed with a profluorescent peptidic substrate (Mca-Pro-Leu-Ala-Gln-Ala-Val-Dpa-Arg-Ser-Ser-Ser-Arg-NH2) which contains a highly fluorescent 7-methoxycoumarin (Mca) group that is efficiently quenched by resonance energy transfer to the 2,4-dinitrophenyl group (Dpa). Mca fluorescence was quenched by the Dpa group until cleavage by ADAM17 at the Ala-Val bond separates the two moieties.

The enzymatic reaction was performed in 384-well microplates with a final volume of 10 μL containing 1% DMSO. Recombinant Human ADAM17 catalytic domain (500 nM) was assayed with 40 μM of substrate and serial dilutions of tested inhibitors (from 10000 nM to 0.04 nM). After two hours of incubation at room temperature, the fluorescence was measured using a microplate reader (320/425 nm).

Data were normalized using the average of positive controls (enzyme with no inhibitor) and negative controls (no enzyme). IC50 were calculated using a four-parameters logistic model.

Activity of the compounds was investigated using MMP1 isolated enzyme. The inhibitors were evaluated on MMP1 inhibition using a profluorescent peptidic substrate (Mca-Pro-Leu-Gly-Leu-Dpa-Ala-Arg-NH2) which contains a highly fluorescent 7-methoxycoumarin (Mca) group that is efficiently quenched by resonance energy transfer to the 2,4-dinitrophenyl group (Dpa). Mca fluorescence was quenched by the Dpa group until cleavage by ADAM17 at the Gly-Leu bond separates the two moieties The enzymatic reaction was performed in 384-well microplates with a final volume of 10 μL containing 1% DMSO. Recombinant Human catalytic domains of MMP1 were assayed with the substrate according to supplier recommendation (ENZO life sciences) and after a preincubation with serial dilutions of tested inhibitors (from 10000 nM to 0.04 nM). After 10 minutes of incubation at room temperature, the fluorescence was measured using a microplate reader (320/425 nm). Data were normalized using the average of positive controls (enzyme with no inhibitor) and negative controls (no enzyme). IC50 were calculated using a four-parameters logistic model.

All publications, patents and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

The following compounds have an IC50 in the hPBMC assay<50 nM: 1, 2, 4a, 4b, 4c, 4d, 4e, 4f, 4g, 4h, 4i, 4j, 5a, 5b, 5c, 5d, 7b, 7c, 7d, 7e, 7g, 7h, 7i, 8, 9, 10, 11, 12, 13, 14, 16b, 16c, 17, 18, 19a, 19c, 19d, 20, 21a, 22, 24, 25, 26a, 26b, 26c, 26d, 26e, 26f, 28a, 28b, 30

The following compounds have an IC50 in the hPBMC assay less than 100 nM but higher than 50 nM: 6, 7a, 15, 16a, 7f, 19b, 21b, 31

The following compounds have an IC50 in the hPBMC assay less than 500 nM but higher than 100 nM: 27, 29

The following compounds have an IC50 in the hPBMC assay less than 1000 nM but higher than 500 nM: 3, 23

| Compound | TACE enz IC$_{50}$ (nM) | MMP1 enz IC$_{50}$ (nM) |
| --- | --- | --- |
| 7b | 5.2 | >10000 |
| 10 | 2.8 | >10000 |
| 11 | 8.2 | >10000 |
| 18 | 3.5 | >10000 |
| 19a | 3.7 | 4464.0 |
| 19d | 7.2 | 4625.0 |
| 22 | 11.0 | >10000 |
| 26f | 11.4 | >10000 |
| 28b | 5.6 | >10000 |

The invention claimed is:

1. A compound of formula (I), a salt thereof, or an enantiomer thereof,

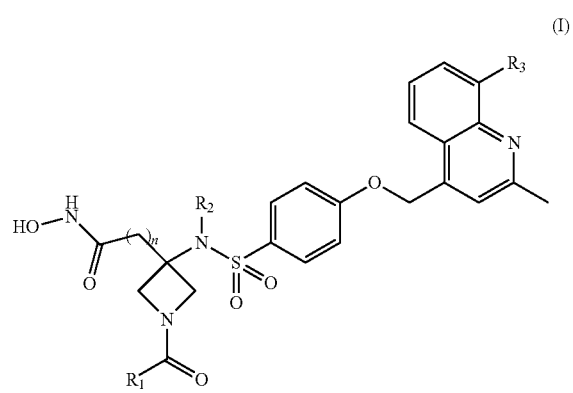

wherein:
  $R_1$ is a hydrogen atom, an alkyl radical, a substituted alkyl radical, an alkenyl radical, a substituted alkenyl radical, an alkynyl radical, a substituted alkynyl radical, an aralkyl radical, a substituted aralkyl radical, a heteroaralkyl radical, a substituted heteroaralkyl radical, a cycloalkyl radical, a substituted cycloalkyl radical, a heterocyclic radical, a substituted heterocyclic radical, an amine radical, a substituted amine radical, a cyclic amine radical, or a heterocyclic amine radical;
  $R_2$ is a hydrogen atom, an alkyl radical or a substituted alkyl radical,
  $R_3$ is a hydrogen atom, an alkyl radical, a substituted alkyl radical, an alkynyl radical, a substituted alkynyl radical, an alkoxy radical, a halogen radical, or a nitrite radical; and
  n is 0 or 1.

2. The compound as claimed in claim 1, wherein:
  $R_1$ is a lower alkyl radical, a substituted lower alkyl radical, an alkenyl radical, a substituted alkenyl radical, an alkynyl radical, a substituted alkynyl radical, a cycloalkyl radical, a substituted cycloalkyl radical, a heterocyclic radical, a substituted heterocyclic radical, an amine radical, a substituted amine radical, a cyclic amine radical, or a heterocyclic amine radical;
  $R_2$ is a hydrogen atom, a lower alkyl radical, a lower alkyl radical substituted with a halogen atom or a lower alkyl radical substituted with an alkoxy radical,
  $R_3$ is a hydrogen atom, a lower alkyl radical, a substituted lower alkyl radical, an alkynyl radical, a substituted alkynyl radical, an alkoxy radical, a halogen atom, or a nitrite radical; and
  n is 0 or 1.

3. The compound as claimed in claim 1, wherein:
  $R_1$ is a lower alkyl radical, a substituted lower alkyl radical, a cycloalkyl radical, a substituted cycloalkyl radical, a heterocyclic radical, a substituted heterocyclic radical, or a substituted amine radical comprising a lower alkyl radical;

$R_2$ is a hydrogen atom, a lower alkyl radical substituted with a fluorine atom, or a lower alkyl radical substituted with an alkoxy radical;

$R_3$ is a hydrogen atom, a lower alkyl radical containing 1 to 3 carbon atoms; a methoxy radical, or an ethoxy radical, a fluorine atom, or a nitrile radical; and n is 0 or 1.

4. The compound as claimed in claim 1, wherein n is 0.

5. The compound as claimed in claim 1, wherein n is 1.

6. A pharmaceutical composition comprising a compound as claimed in claim 1, and a pharmaceutically acceptable carrier.

7. The compound as claimed in claim 1, wherein $R_2$ is hydrogen atom, a methyl radical, an ethyl radical, an isopropyl radical, or a methoxyethane radical.

8. The compound as claimed in claim 1, wherein $R_3$ is a hydrogen atom, a methyl radical, or a halogen.

9. A compound of formula (I), a salt thereof, or an enantiomer thereof,

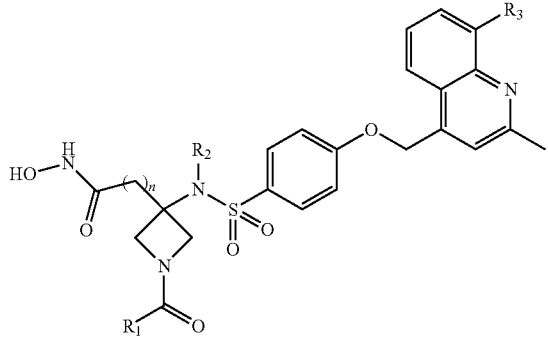

(I)

wherein the compound is selected from the group consisting of:

2-(1-acetyl-3-((4-((2-methylquinolin-4-yl)methoxy)phenyl)sulfonamido)azetidin-3-yl)-N-hydroxyacetamide;

tert-butyl 3-(2-(hydroxyamino)-2-oxoethyl)-3-((4-((2-methylquinolin-4-yl)methoxy)phenyl)sulfonamido)azetidine-1-carboxylate;

2-(1-acetyl-3-((N-methyl-4-((2-methylquinolin-4-yl)methoxy)phenyl)sulfonamido)azetidin-3-yl)-N-hydroxyacetamide;

N-hydroxy-2-(1-(3-methylbutanoyl)-3-((4-((2-methylquinolin-4-yl)methoxy)phenyl)sulfonamido)azetidin-3-yl)acetamide;

N-hydroxy-2-(1-isobutyryl-3-((4-((2-methylquinolin-4-yl)methoxy)phenyl)sulfonamido)azetidin-3-yl)acetamide;

2-(1-(cyclopropanecarbonyl)-3-((4-((2-methylquinolin-4-yl)methoxy)phenyl)sulfonamido)azetidin-3-yl)-N-hydroxyacetamide;

N-hydroxy-2-(3-((4-((2-methylquinolin-4-yl)methoxy)phenyl)sulfonamido)-1-pivaloylazetidin-3-yl)acetamide;

2-(1-butyryl-3-((4-((2-methylquinolin-4-yl)methoxy)phenyl)sulfonamido)azetidin-3-yl)-N-hydroxyacetamide;

N-hydroxy-2-(1-(2-methoxyacetyl)-3-((4-((2-methylquinolin-4-yl)methoxy)phenyl)sulfonamido)azetidin-3-yl)acetamide;

N-hydroxy-2-(3-((4-((2-methylquinolin-4-yl)methoxy)phenyl)sulfonamido)-1-(tetrahydro-2H-pyran-4-carbonyl)azetidin-3-yl)acetamide;

2-(1-(cyclopentanecarbonyl)-3-((4-((2-methylquinolin-4-yl)methoxy)phenyl)sulfonamido)azetidin-3-yl)-N-hydroxyacetamide;

2-(1-(2-ethylbutanoyl)-3-((4-((2-methylquinolin-4-yl)methoxy)phenyl)sulfonamido)azetidin-3-yl)-N-hydroxyacetamide;

2-(1-(cyclohexanecarbonyl)-3-((4-((2-methylquinolin-4-yl)methoxy)phenyl)sulfonamido)azetidin-3-yl)-N-hydroxyacetamide;

ethyl 3-(2-(hydroxyamino)-2-oxoethyl)-3-((4-((2-methylquinolin-4-yl)methoxy)phenyl)sulfonamido)azetidine-1-carboxylate;

methyl 3-(2-(hydroxyamino)-2-oxoethyl)-3-((4-((2-methylquinolin-4-yl)methoxy)phenyl)sulfonamido)azetidine-1-carboxylate;

allyl 3-(2-(hydroxyamino)-2-oxoethyl)-3-((4-((2-methylquinolin-4-yl)methoxy)phenyl)sulfonamido)azetidine-1-carboxylate;

isopropyl 3-(2-(hydroxyamino)-2-oxoethyl)-3-((4-((2-methylquinolin-4-yl)methoxy)phenyl)sulfonamido)azetidine-1-carboxylate;

2-(1-acetyl-3-((4-((8-fluoro-2-methylquinolin-4-yl)methoxy)phenyl)sulfonamido)azetidin-3-yl)-N-hydroxyacetamide;

N-hydroxy-3-((4-((2-methylquinolin-4-yl)methoxy)phenyl)sulfonamido)-1-pivaloylazetidine-3-carboxamide;

N-hydroxy-1-isobutyryl-3-((4-((2-methylquinolin-4-yl)methoxy)phenyl)sulfonamido)azetidine-3-carboxamide;

N-hydroxy-1-(3-methylbutanoyl)-3-((4-((2-methylquinolin-4-yl)methoxy)phenyl)sulfonamido)azetidine-3-carboxamide;

N-hydroxy-3-((4-((2-methylquinolin-4-yl)methoxy)phenyl)sulfonamido)-1-(tetrahydro-2H-pyran-4-carbonyl)azetidine-3-carboxamide;

1-(cyclobutanecarbonyl)-N-hydroxy-3-((4-((2-methylquinolin-4-yl)methoxy)phenyl)sulfonamido)azetidine-3-carboxamide;

1-(2-ethylbutanoyl)-N-hydroxy-3-((4-((2-methylquinolin-4-yl)methoxy)phenyl)sulfonamido)azetidine-3-carboxamide;

N-hydroxy-3-((4-((2-methylquinolin-4-yl)methoxy)phenyl)sulfonamido)-1-propionylazetidine-3-carboxamide;

1-butyryl-N-hydroxy-3-((4-((2-methylquinolin-4-yl)methoxy)phenyl)sulfonamido)azetidine-3-carboxamide;

N-hydroxy-3-((4-((2-methylquinolin-4-yl)methoxy)phenyl)sulfonamido)-1-pentanoylazetidine-3-carboxamide;

1-acetyl-N-hydroxy-3-((4-((2-methylquinolin-4-yl)methoxy)phenyl)sulfonamido)azetidine-3-carboxamide;

N-hydroxy-2-(3-((4-((2-methylquinolin-4-yl)methoxy)phenyl)sulfonamido)-1-(piperidine-1-carbonyl)azetidin-3-yl)acetamide;

N-hydroxy-2-(1-(4-methylpiperazine-1-carbonyl)-3-((4-((2-methylquinolin-4-yl)methoxy)phenyl)sulfonamido)azetidin-3-yl)acetamide;

2-(1-(3,3-dimethylbutanoyl)-3-((4-((2-methylquinolin-4-yl)methoxy)phenyl)sulfonamido)azetidin-3-yl)-N-hydroxyacetamide;
N-hydroxy-2-(3-((4-((2-methylquinolin-4-yl)methoxy)phenyl)sulfonamido)-1-(2-(piperidin-1-yl)acetyl)azetidin-3-yl)acetamide;
2-(1-(2-cyclobutylacetyl)-3-((4-((2-methylquinolin-4-yl)methoxy)phenyl)sulfonamido)azetidin-3-yl)-N-hydroxyacetamide;
tert-butyl 3-(hydroxycarbamoyl)-3-((4-((2-methylquinolin-4-yl)methoxy)phenyl)sulfonamido)azetidine-1-carboxylate;
1-(3,3-dimethylbutanoyl)-N-hydroxy-3-((4-((2-methylquinolin-4-yl)methoxy)phenyl)sulfonamido)azetidine-3-carboxamide;
N-hydroxy-3-((4-((2-methylquinolin-4-yl)methoxy)phenyl)sulfonamido)-1-(piperidine-1-carbonyl)azetidine-3-carboxamide;
N-hydroxy-3-((4-((2-methylquinolin-4-yl)methoxy)phenyl)sulfonamido)-1-(morpholine-4-carbonyl)azetidine-3-carboxamide;
N-hydroxy-1-(4-methylpiperazine-1-carbonyl)-3-((4-((2-methylquinolin-4-yl)methoxy)phenyl)sulfonamido)azetidine-3-carboxamide;
allyl 3-(hydroxycarbamoyl)-3-((4-((2-methylquinolin-4-yl)methoxy)phenyl)sulfonamido)azetidine-1-carboxylate;
2-(1-(2-(dimethylamino)-2-methylpropanoyl)-3-((4-((2-methylquinolin-4-yl)methoxy)phenyl)sulfonamido)azetidin-3-yl)-N-hydroxyacetamide;
N-hydroxy-1-isobutyryl-3-((N-methyl-4-((2-methylquinolin-4-yl)methoxy)phenyl)sulfonamido)azetidine-3-carboxamide;
1-(2-ethylbutanoyl)-N-hydroxy-3-((N-methyl-4-((2-methylquinolin-4-yl)methoxy)phenyl)sulfonamido)azetidine-3-carboxamide;
N-hydroxy-3-((N-methyl-4-((2-methylquinolin-4-yl)methoxy)phenyl)sulfonamido)-1-(tetrahydro-2H-pyran-4-carbonyl)azetidine-3-carboxamide;
N-hydroxy-3-((N-methyl-4-((2-methylquinolin-4-yl)methoxy)phenyl)sulfonamido)-1-(3-methylbutanoyl)azetidine-3-carboxamide;
tert-butyl 3-(hydroxycarbamoyl)-3-((N-methyl-4-((2-methylquinolin-4-yl)methoxy)phenyl)sulfonamido)azetidine-1-carboxylate;
3-((N-ethyl-4-((2-methylquinolin-4-yl)methoxy)phenyl)sulfonamido)-N-hydroxy-1-isobutyrylazetidine-3-carboxamide;
3-((N-ethyl-4-((2-methylquinolin-4-yl)methoxy)phenyl)sulfonamido)-N-hydroxy-1-(tetrahydro-2H-pyran-4-carbonyl)azetidine-3-carboxamide;
N-hydroxy-1-isobutyryl-3-((N-(2-methoxyethyl)-4-((2-methylquinolin-4-yl)methoxy)phenyl)sulfonamido)azetidine-3-carboxamide;
N-hydroxy-1-isobutyryl-3-((N-isopropyl-4-((2-methylquinolin-4-yl)methoxy)phenyl)sulfonamido)azetidine-3-carboxamide
2-(1-acetyl-3-((4-((2,8-dimethylquinolin-4-yl)methoxy)phenyl)sulfonamido)azetidin-3-yl)-N-hydroxyacetamide;
N-hydroxy-2-(3-((4-((2-methyl quinolin-4-yl)methoxy)phenyl)sulfonamido)-1-(morpholine-4-carbonyl)azetidin-3-yl)acetamide;
N-hydroxy-1-((1 r,3 r)-3-methoxycyclobutane-1-carbonyl)-3-((4-((2-methylquinolin-4-yl)methoxy)phenyl)sulfonamido)azetidine-3-carboxamide;
N-hydroxy-1-((1 s,3 s)-3-methoxycyclobutane-1-carbonyl)-3-((4-((2-methylquinolin-4-yl)methoxy)phenyl)sulfonamido)azetidine-3-carboxamide;
1-(2-cyclopropylacetyl)-N-hydroxy-3-((4-((2-methylquinolin-4-yl)methoxy)phenyl)sulfonamido)azetidine-3-carboxamide;
(S)—N-hydroxy-1-(2-methylbutanoyl)-3-((4-((2-methylquinolin-4-yl)methoxy)phenyl)sulfonamido)azetidine-3-carboxamide;
1-(3,3-difluorocyclobutane-1-carbonyl)-N-hydroxy-3-((4-((2-methylquinolin-4-yl)methoxy)phenyl)sulfonamido)azetidine-3-carboxamide;
1-(2-cyclobutylacetyl)-N-hydroxy-3-((4-((2-methylquinolin-4-yl)methoxy)phenyl)sulfonamido)azetidine-3-carboxamide;
3-((4-((2,8-dimethylquinolin-4-yl)methoxy)phenyl)sulfonamido)-N-hydroxy-1-isobutyrylazetidine-3-carboxamide;
N-hydroxy-2-(1-(4-isopropylpiperazine-1-carbonyl)-3-((4-((2-methylquinolin-4-yl)methoxy)phenyl)sulfonamido)azetidin-3-yl)acetamide;
2-(1-(4-ethylpiperazine-1-carbonyl)-3-((4-((2-methylquinolin-4-yl)methoxy)phenyl)sulfonamido)azetidin-3-yl)-N-hydroxyacetamide;
3-((4-(8-fluoro-2-methylquinolin-4-yl)methoxy)phenyl)sulfonamido)-N-hydroxy-1-(3-methylbutanoyl)azetidine-3-carboxamide;
3-((4-(8-fluoro-2-methylquinolin-4-yl)methoxy)-N-methylphenyl)sulfonamido)-N-hydroxy-1-isobutyrylazetidine-3-carboxamide; and
2-(3-((4-((2,8-dimethylquinolin-4-yl)methoxy)phenyl)sulfonamido)-1-(4-methylpiperazine-1-carbonyl)azetidin-3-yl)-N-hydroxyacetamide.

10. A method for the treatment of an inflammatory skin disease, the method comprising inhibiting TNFα production by administering to a subject in need thereof an effective amount of a compound as defined in claim 9;
wherein the inflammatory skin disease is selected from the group consisting of psoriasis, atopic dermatitis, psoriatic arthritis, acne, allergic contact dermatitis and actinic keratosis.

11. A method for the treatment of an inflammatory skin disease, the method comprising inhibiting the activity of TACE by administering to a subject in need thereof an effective amount of a compound as defined in claim 9;
wherein the inflammatory skin disease is selected from the group consisting of psoriasis, atopic dermatitis, psoriatic arthritis, acne, allergic contact dermatitis and actinic keratosis.

12. The compound as claimed in claim 9, wherein the compound is selected from the group consisting of:
2-(1-acetyl-3-((4-((2-methylquinolin-4-yl)methoxy)phenyl)sulfonamido)azetidin-3-yl)-N-hydroxyacetamide;
2-(1-acetyl-3-((N-methyl-4-((2-methylquinolin-4-yl)methoxy)phenyl)sulfonamido)azetidin-3-yl)-N-hydroxyacetamide;
N-hydroxy-2-(1-(3-methylbutanoyl)-3-((4-((2-methylquinolin-4-yl)methoxy)phenyl)sulfonamido)azetidin-3-yl)acetamide;
N-hydroxy-2-(1-isobutyryl-3-((4-((2-methylquinolin-4-yl)methoxy)phenyl)sulfonamido)azetidin-3-yl)acetamide;
2-(1-(cyclopropanecarbonyl)-3-((4-((2-methylquinolin-4-yl)methoxy)phenyl)sulfonamido)azetidin-3-yl)-N-hydroxyacetamide;

N-hydroxy-2-(3-((4-((2-methylquinolin-4-yl)methoxy)phenyl)sulfonamido)-1-pivaloylazetidin-3-yl)acetamide;
2-(1-butyryl-3-((4-((2-methylquinolin-4-yl)methoxy)phenyl)sulfonamido)azetidin-3-yl)-N-hydroxyacetamide;
N-hydroxy-2-(1-(2-methoxyacetyl)-3-((4-((2-methylquinolin-4-yl)methoxy)phenyl)sulfonamido)azetidin-3-yl)acetamide;
N-hydroxy-2-(3-((4-((2-methylquinolin-4-yl)methoxy)phenyl)sulfonamido)-1-(tetrahydro-2H-pyran-4-carbonyl)azetidin-3-yl)acetamide;
2-(1-(cyclopentanecarbonyl)-3-((4-((2-methylquinolin-4-yl)methoxy)phenyl)sulfonamido)azetidin-3-yl)-N-hydroxyacetamide;
2-(1-(2-ethylbutanoyl)-3-((4-((2-methylquinolin-4-yl)methoxy)phenyl)sulfonamido)azetidin-3-yl)-N-hydroxyacetamide;
2-(1-(cyclohexanecarbonyl)-3-((4-((2-methylquinolin-4-yl)methoxy)phenyl)sulfonamido)azetidin-3-yl)-N-hydroxyacetamide;
2-(1-acetyl-3-((4-((8-fluoro-2-methylquinolin-4-yl)methoxy)phenyl)sulfonamido)azetidin-3-yl)-N-hydroxyacetamide;
N-hydroxy-3-((4-((2-methylquinolin-4-yl)methoxy)phenyl)sulfonamido)-1-pivaloylazetidine-3-carboxamide;
N-hydroxy-1-isobutyryl-3-((4-((2-methylquinolin-4-yl)methoxy)phenyl)sulfonamido)azetidine-3-carboxamide;
N-hydroxy-1-(3-methylbutanoyl)-3-((4-((2-methylquinolin-4-yl)methoxy)phenyl)sulfonamido)azetidine-3-carboxamide;
N-hydroxy-3-((4-((2-methylquinolin-4-yl)methoxy)phenyl)sulfonamido)-1-(tetrahydro-2H-pyran-4-carbonyl)azetidine-3-carboxamide;
1-(cyclobutanecarbonyl)-N-hydroxy-3-((4-((2-methylquinolin-4-yl)methoxy)phenyl)sulfonamido)azetidine-3-carboxamide;
1-(2-ethylbutanoyl)-N-hydroxy-3-((4-((2-methylquinolin-4-yl)methoxy)phenyl)sulfonamido)azetidine-3-carboxamide;
N-hydroxy-3-((4-((2-methylquinolin-4-yl)methoxy)phenyl)sulfonamido)-1-propionylazetidine-3-carboxamide;
1-butyryl-N-hydroxy-3-((4-((2-methylquinolin-4-yl)methoxy)phenyl)sulfonamido)azetidine-3-carboxamide;
N-hydroxy-3-((4-((2-methylquinolin-4-yl)methoxy)phenyl)sulfonamido)-1-pentanoylazetidine-3-carboxamide;
1-acetyl-N-hydroxy-3-((4-((2-methylquinolin-4-yl)methoxy)phenyl)sulfonamido)azetidine-3-carboxamide;
N-hydroxy-2-(3-((4-((2-methylquinolin-4-yl)methoxy)phenyl)sulfonamido)-1-(piperidine-1-carbonyl)azetidin-3-yl)acetamide;
N-hydroxy-2-(1-(4-methylpiperazine-1-carbonyl)-3-((4-((2-methylquinolin-4-yl)methoxy)phenyl)sulfonamido)azetidin-3-yl)acetamide;
2-(1-(3,3-dimethylbutanoyl)-3-((4-((2-methylquinolin-4-yl)methoxy)phenyl)sulfonamido)azetidin-3-yl)-N-hydroxyacetamide;
N-hydroxy-2-(3-((4-((2-methylquinolin-4-yl)methoxy)phenyl)sulfonamido)-1-(2-(piperidin-1-yl)acetyl)azetidin-3-yl)acetamide;
2-(1-(2-cyclobutylacetyl)-3-((4-((2-methylquinolin-4-yl)methoxy)phenyl)sulfonamido)azetidin-3-yl)-N-hydroxyacetamide;
1-(3,3-dimethylbutanoyl)-N-hydroxy-3-((4-((2-methylquinolin-4-yl)methoxy)phenyl)sulfonamido)azetidine-3-carboxamide;
N-hydroxy-3-((4-((2-methylquinolin-4-yl)methoxy)phenyl)sulfonamido)-1-(piperidine-1-carbonyl)azetidine-3-carboxamide;
N-hydroxy-3-((4-((2-methylquinolin-4-yl)methoxy)phenyl)sulfonamido)-1-(morpholine-4-carbonyl)azetidine-3-carboxamide;
N-hydroxy-1-(4-methylpiperazine-1-carbonyl)-3-((4-((2-methylquinolin-4-yl)methoxy)phenyl)sulfonamido)azetidine-3-carboxamide;
2-(1-(2-(dimethylamino)-2-methylpropanoyl)-3-((4-((2-methylquinolin-4-yl)methoxy)phenyl)sulfonamido)azetidin-3-yl)-N-hydroxyacetamide;
N-hydroxy-1-isobutyryl-3-((N-methyl-4-((2-methylquinolin-4-yl)methoxy)phenyl)sulfonamido)azetidine-3-carboxamide;
1-(2-ethylbutanoyl)-N-hydroxy-3-((N-methyl-4-((2-methylquinolin-4-yl)methoxy)phenyl)sulfonamido)azetidine-3-carboxamide;
N-hydroxy-3-((N-methyl-4-((2-methylquinolin-4-yl)methoxy)phenyl)sulfonamido)-1-(tetrahydro-2H-pyran-4-carbonyl)azetidine-3-carboxamide;
N-hydroxy-3-((N-methyl-4-((2-methylquinolin-4-yl)methoxy)phenyl)sulfonamido)-1-(3-methylbutanoyl)azetidine-3-carboxamide;
3-((N-ethyl-4-((2-methylquinolin-4-yl)methoxy)phenyl)sulfonamido)-N-hydroxy-1-isobutyrylazetidine-3-carboxamide;
3-((N-ethyl-4-((2-methylquinolin-4-yl)methoxy)phenyl)sulfonamido)-N-hydroxy-1-(tetrahydro-2H-pyran-4-carbonyl)azetidine-3-carboxamide;
N-hydroxy-1-isobutyryl-3-((N-(2-methoxyethyl)-4-((2-methylquinolin-4-yl)methoxy)phenyl)sulfonamido)azetidine-3-carboxamide;
N-hydroxy-1-isobutyryl-3-((N-isopropyl-4-((2-methylquinolin-4-yl)methoxy)phenyl)sulfonamido)azetidine-3-carboxamide
2-(1-acetyl-3-((4-((2,8-dimethylquinolin-4-yl)methoxy)phenyl)sulfonamido)azetidin-3-yl)-N-hydroxyacetamide;
N-hydroxy-2-(3-((4-((2-methyl quinolin-4-yl)methoxy)phenyl)sulfonamido)-1-(morpholine-4-carbonyl)azetidin-3-yl)acetamide;
N-hydroxy-1-((1r,3r)-3-methoxycyclobutane-1-carbonyl)-3-((4-((2-methylquinolin-4-yl)methoxy)phenyl)sulfonamido)azetidine-3-carboxamide;
N-hydroxy-1-((1s,3 s)-3-methoxycyclobutane-1-carbonyl)-3-((4-((2-methylquinolin-4-yl)methoxy)phenyl)sulfonamido)azetidine-3-carboxamide;
1-(2-cyclopropylacetyl)-N-hydroxy-3-((4-((2-methylquinolin-4-yl)methoxy)phenyl)sulfonamido)azetidine-3-carboxamide;
(S)—N-hydroxy-1-(2-methylbutanoyl)-3-((4-((2-methylquinolin-4-yl)methoxy)phenyl)sulfonamido)azetidine-3-carboxamide;
1-(3,3-difluorocyclobutane-1-carbonyl)-N-hydroxy-3-((4-((2-methylquinolin-4-yl)methoxy)phenyl)sulfonamido)azetidine-3-carboxamide;
1-(2-cyclobutylacetyl)-N-hydroxy-3-((4-((2-methylquinolin-4-yl)methoxy)phenyl)sulfonamido)azetidine-3-carboxamide;

3-((4-((2,8-dimethylquinolin-4-yl)methoxy)phenyl)sulfonamido)-N-hydroxy-1-isobutyrylazetidine-3-carboxamide;

N-hydroxy-2-(1-(4-isopropylpiperazine-1-carbonyl)-3-((4-((2-methylquinolin-4-yl)methoxy)phenyl)sulfonamido)azetidin-3-yl)acetamide;

2-(1-(4-ethylpiperazine-1-carbonyl)-3-((4-((2-methylquinolin-4-yl)methoxy)phenyl)sulfonamido)azetidin-3-yl)-N-hydroxyacetamide;

3-((4-(8-fluoro-2-methylquinolin-4-yl)methoxy)phenyl)sulfonamido)-N-hydroxy-1-(3-methylbutanoyl)azetidine-3-carboxamide;

3-((4-(8-fluoro-2-methylquinolin-4-yl)methoxy)-N-methylphenyl)sulfonamido)-N-hydroxy-1-isobutyrylazetidine-3-carboxamide; and 2-(3-((4-((2,8-dimethylquinolin-4-yl)methoxy)phenyl)sulfonamido)-1-(4-methylpiperazine-1-carbonyl)azetidin-3-yl)-N-hydroxyacetamide.

\* \* \* \* \*